United States Patent
Holop et al.

(10) Patent No.: US 11,090,124 B2
(45) Date of Patent: *Aug. 17, 2021

(54) INSTRUMENT STERILE ADAPTER DRIVE INTERFACE

(71) Applicant: Intuitive Surgical Operations, Inc., Sunnyvale, CA (US)

(72) Inventors: Robert E. Holop, Santa Clara, CA (US); Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 16/426,367

(22) Filed: May 30, 2019

(65) Prior Publication Data
US 2019/0274766 A1 Sep. 12, 2019

Related U.S. Application Data

(63) Continuation of application No. 14/911,510, filed as application No. PCT/US2014/051050 on Aug. 14, 2014, now Pat. No. 10,307,213.
(Continued)

(51) Int. Cl.
*F16H 57/10* (2006.01)
*A61B 34/30* (2016.01)
(Continued)

(52) U.S. Cl.
CPC .............. *A61B 34/30* (2016.02); *A61B 46/10* (2016.02); *A61B 2017/00477* (2013.01); *A61B 2034/303* (2016.02)

(58) Field of Classification Search
CPC .............. A61B 34/30; A61B 2034/303; A61B 2017/00477
See application file for complete search history.

(56) References Cited

U.S. PATENT DOCUMENTS

| 793,510 A | 6/1905 | Cramer et al. |
| 3,596,498 A | 8/1971 | Bradlee |

(Continued)

FOREIGN PATENT DOCUMENTS

| CA | 2709634 A1 | 7/2009 |
| CN | 2573759 Y | 9/2003 |

(Continued)

OTHER PUBLICATIONS

Article 94(3) Communication in EP Application No. 14836696.6, dated Aug. 20, 2019.
(Continued)

*Primary Examiner* — Jake Cook

(57) ABSTRACT

A surgical system (200) includes a surgical instrument (260) that is sensitive to backlash that would adversely affect the transmission of controlled torque and position to the surgical instrument. The surgical instrument (260) is coupled to motors in a surgical instrument manipulator assembly (240) via a mechanical interface. The combination of the mechanical interface and surgical instrument manipulator assembly (240) have low backlash, e.g., less than 0.7 degrees. The backlash is controlled in the surgical instrument manipulator assembly (240). From the drive output disk (545) in the surgical instrument manipulator assembly to the driven disk (964) of the surgical instrument, the mechanical interface has zero backlash for torque levels used in surgical procedures.

20 Claims, 36 Drawing Sheets

Related U.S. Application Data

(60) Provisional application No. 61/866,124, filed on Aug. 15, 2013.

(51) Int. Cl.
*A61B 46/10* (2016.01)
*A61B 17/00* (2006.01)

(56) References Cited

U.S. PATENT DOCUMENTS

| | | |
|---|---|---|
| 4,117,359 A | 9/1978 | Wehde |
| 4,259,876 A | 4/1981 | Belyanin et al. |
| 4,281,447 A | 8/1981 | Miller et al. |
| 4,283,165 A | 8/1981 | Vertut |
| 4,696,524 A | 9/1987 | Cloyd |
| 4,724,713 A | 2/1988 | Olasz et al. |
| 4,899,608 A | 2/1990 | Knappe et al. |
| 4,911,399 A | 3/1990 | Green |
| 5,528,955 A | 6/1996 | Hannaford et al. |
| 5,674,024 A | 10/1997 | Daumal et al. |
| 5,816,769 A | 10/1998 | Bauer et al. |
| 6,007,550 A | 12/1999 | Wang et al. |
| 6,132,368 A | 10/2000 | Cooper |
| 6,139,245 A | 10/2000 | Hofmeister |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,459,926 B1 | 10/2002 | Nowlin et al. |
| 6,494,662 B1 | 12/2002 | De Montalembert |
| 6,817,974 B2 | 11/2004 | Cooper et al. |
| 6,994,708 B2 | 2/2006 | Manzo et al. |
| 6,997,079 B2 | 2/2006 | Nomura et al. |
| 7,261,726 B2 | 8/2007 | Jinno et al. |
| 7,524,320 B2 | 4/2009 | Tierney et al. |
| 7,666,191 B2 | 2/2010 | Orban, III et al. |
| 7,699,855 B2 | 4/2010 | Anderson |
| 7,727,244 B2 | 6/2010 | Orban, III et al. |
| 7,752,937 B1 | 7/2010 | Dornan |
| 7,823,330 B2 | 11/2010 | Ostrowski et al. |
| 7,886,743 B2 | 2/2011 | Cooper et al. |
| 7,935,130 B2 | 5/2011 | Williams et al. |
| 7,963,913 B2 | 6/2011 | Devengenzo et al. |
| 8,105,338 B2 | 1/2012 | Anderson et al. |
| 8,162,926 B2 | 4/2012 | Schena |
| 8,306,656 B1 | 11/2012 | Schaible et al. |
| 8,333,755 B2 | 12/2012 | Cooper et al. |
| 8,347,757 B2 | 1/2013 | Duval |
| 8,348,931 B2 | 1/2013 | Cooper et al. |
| 8,365,633 B2 | 2/2013 | Simaan et al. |
| 8,444,631 B2 | 5/2013 | Yeung et al. |
| 8,479,969 B2 | 7/2013 | Shelton, IV et al. |
| 8,506,555 B2 | 8/2013 | Ruiz et al. |
| 8,578,810 B2 | 11/2013 | Donhowe |
| 8,644,988 B2 | 2/2014 | Prisco et al. |
| 8,771,270 B2 | 7/2014 | Burbank et al. |
| 8,800,838 B2 | 8/2014 | Shelton, IV et al. |
| 8,887,595 B2 | 11/2014 | Williams et al. |
| 8,911,471 B2 | 12/2014 | Spivey et al. |
| 9,028,494 B2 | 5/2015 | Shelton, IV et al. |
| 9,078,684 B2 | 7/2015 | Williams et al. |
| 9,121,494 B2 | 9/2015 | Buchleitner et al. |
| 9,204,923 B2 | 12/2015 | Manzo et al. |
| 9,232,979 B2 | 1/2016 | Parihar et al. |
| 9,244,523 B2 | 1/2016 | Ogawa et al. |
| 9,244,524 B2 | 1/2016 | Inoue et al. |
| 9,259,274 B2 | 2/2016 | Prisco et al. |
| 9,291,793 B2 | 3/2016 | Cooper |
| 9,339,342 B2 | 5/2016 | Prisco et al. |
| 9,423,869 B2 | 8/2016 | Yanagihara |
| 9,477,301 B2 | 10/2016 | Kishi |
| 9,524,022 B2 | 12/2016 | Nakayama |
| 9,632,577 B2 | 4/2017 | Ogawa et al. |
| 9,671,860 B2 | 6/2017 | Ogawa et al. |
| 9,687,312 B2 | 6/2017 | Dachs, II et al. |
| 9,707,684 B2 | 7/2017 | Ruiz et al. |
| 9,757,149 B2 | 9/2017 | Cooper et al. |
| 10,016,244 B2 | 7/2018 | Cooper et al. |
| 10,022,193 B2 | 7/2018 | Cooper et al. |
| 10,045,828 B2 | 8/2018 | Dachs, II et al. |
| 10,130,366 B2 | 11/2018 | Shelton, IV et al. |
| 10,271,911 B2 | 4/2019 | Cooper et al. |
| 10,307,213 B2 | 6/2019 | Holop et al. |
| 10,478,163 B2 | 11/2019 | Prisco et al. |
| 10,595,836 B2 | 3/2020 | Smaby et al. |
| 10,595,887 B2 | 3/2020 | Shelton, IV et al. |
| 10,595,945 B2 | 3/2020 | Kapadia et al. |
| 10,603,125 B2 | 3/2020 | Komuro et al. |
| 10,631,949 B2 | 4/2020 | Schuh et al. |
| 10,653,489 B2 | 5/2020 | Kopp |
| 10,660,651 B2 | 5/2020 | Baril et al. |
| 10,667,877 B2 | 6/2020 | Kapadia |
| 10,675,104 B2 | 6/2020 | Kapadia |
| 10,695,138 B2 | 6/2020 | Cooper et al. |
| 10,710,246 B2 | 7/2020 | McGrogan et al. |
| 10,758,310 B2 | 9/2020 | Shelton, IV et al. |
| 10,779,898 B2 | 9/2020 | Hill et al. |
| 10,792,112 B2 | 10/2020 | Kokish et al. |
| 10,799,303 B2 | 10/2020 | Cooper et al. |
| 10,820,947 B2 | 11/2020 | Julian |
| 10,820,954 B2 | 11/2020 | Marsot et al. |
| 10,932,868 B2 | 3/2021 | Solomon et al. |
| 10,980,556 B2 | 4/2021 | Anderson et al. |
| 10,993,773 B2 | 5/2021 | Cooper et al. |
| 10,993,775 B2 | 5/2021 | Cooper et al. |
| 2002/0087048 A1 | 7/2002 | Brock et al. |
| 2002/0096885 A1 | 7/2002 | Gomez et al. |
| 2002/0111635 A1 | 8/2002 | Jensen et al. |
| 2002/0153221 A1 | 10/2002 | Schnepf |
| 2004/0035243 A1 | 2/2004 | Duval |
| 2004/0049205 A1 | 3/2004 | Lee et al. |
| 2005/0042943 A1 | 2/2005 | Mocivnik et al. |
| 2005/0089345 A1 | 4/2005 | Yasumoto et al. |
| 2005/0277875 A1 | 12/2005 | Selkee |
| 2006/0084945 A1 | 4/2006 | Moll et al. |
| 2007/0043338 A1 | 2/2007 | Moll et al. |
| 2007/0232858 A1 | 10/2007 | Macnamara et al. |
| 2008/0009838 A1 | 1/2008 | Schena et al. |
| 2008/0046122 A1 | 2/2008 | Manzo et al. |
| 2008/0058861 A1 | 3/2008 | Cooper et al. |
| 2008/0065102 A1 | 3/2008 | Cooper et al. |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0000899 A1 | 1/2009 | Paterra et al. |
| 2009/0088774 A1 | 4/2009 | Swarup et al. |
| 2010/0170519 A1 | 7/2010 | Romo et al. |
| 2010/0175701 A1 | 7/2010 | Reis et al. |
| 2010/0318101 A1 | 12/2010 | Choi et al. |
| 2011/0015650 A1 | 1/2011 | Choi et al. |
| 2011/0118754 A1 | 5/2011 | Dachs, II et al. |
| 2011/0160743 A1 | 6/2011 | Espinal |
| 2011/0277775 A1 | 11/2011 | Holop et al. |
| 2011/0282356 A1 | 11/2011 | Solomon et al. |
| 2011/0282357 A1 | 11/2011 | Rogers et al. |
| 2011/0295269 A1 | 12/2011 | Swensgard et al. |
| 2011/0295270 A1 | 12/2011 | Giordano et al. |
| 2012/0021867 A1 | 1/2012 | Rosmarin |
| 2012/0111136 A1 | 5/2012 | Kawakami |
| 2012/0118917 A1 | 5/2012 | Naughton et al. |
| 2012/0123441 A1 | 5/2012 | Au et al. |
| 2012/0239060 A1 | 9/2012 | Orban, III et al. |
| 2012/0245596 A1 | 9/2012 | Meenink et al. |
| 2012/0247489 A1 | 10/2012 | Orban, III et al. |
| 2012/0289974 A1 | 11/2012 | Rogers et al. |
| 2012/0297908 A1 | 11/2012 | Bourgoine et al. |
| 2012/0298719 A1 | 11/2012 | Shelton, IV et al. |
| 2013/0325031 A1 | 12/2013 | Schena et al. |
| 2014/0005678 A1 | 1/2014 | Shelton, IV et al. |
| 2014/0005708 A1 | 1/2014 | Shelton, IV |
| 2014/0100558 A1 | 4/2014 | Schmitz et al. |
| 2015/0008090 A1 | 1/2015 | Adamczak et al. |
| 2015/0150635 A1 | 6/2015 | Kilroy et al. |
| 2015/0157355 A1 | 6/2015 | Price et al. |

(56) References Cited

U.S. PATENT DOCUMENTS

| | | |
|---|---|---|
| 2015/0260220 A1 | 9/2015 | Owada et al. |
| 2015/0280384 A1 | 10/2015 | Leimbach et al. |
| 2016/0058443 A1 | 3/2016 | Yates et al. |
| 2016/0184034 A1 | 6/2016 | Holop et al. |
| 2016/0184036 A1 | 6/2016 | Solomon et al. |
| 2016/0184037 A1 | 6/2016 | Cooper et al. |
| 2016/0199138 A1 | 7/2016 | Cooper et al. |
| 2016/0361049 A1 | 12/2016 | Dachs, II et al. |
| 2017/0027656 A1 | 2/2017 | Robert et al. |
| 2017/0165017 A1 | 6/2017 | Chaplin et al. |
| 2018/0000472 A1 | 1/2018 | Beira |
| 2018/0168671 A1 | 6/2018 | Overmyer |
| 2018/0280097 A1 | 10/2018 | Cooper et al. |
| 2019/0125354 A1 | 5/2019 | Deck et al. |
| 2019/0159851 A1 | 5/2019 | Karguth et al. |
| 2019/0192137 A1 | 6/2019 | Shelton, IV et al. |
| 2019/0223966 A1 | 7/2019 | Holop et al. |
| 2019/0231455 A1 | 8/2019 | Cooper et al. |
| 2019/0290310 A1 | 9/2019 | Klein |
| 2019/0298471 A1 | 10/2019 | Holop |
| 2020/0000532 A1 | 1/2020 | Kreissig et al. |
| 2020/0093503 A1 | 3/2020 | Deville et al. |
| 2020/0222130 A1 | 7/2020 | Cooper et al. |
| 2020/0275928 A1 | 9/2020 | Shelton, IV et al. |
| 2020/0289214 A1 | 9/2020 | Cooper et al. |
| 2020/0305990 A1 | 10/2020 | Ago et al. |

FOREIGN PATENT DOCUMENTS

| | | |
|---|---|---|
| CN | 1843284 A | 10/2006 |
| CN | 1939228 A | 4/2007 |
| CN | 1973753 A | 6/2007 |
| CN | 101045015 A | 10/2007 |
| CN | 101443162 A | 5/2009 |
| CN | 101528151 A | 9/2009 |
| EP | 2298218 A2 | 3/2011 |
| JP | H06114000 A | 4/1994 |
| JP | H10249777 A | 9/1998 |
| JP | 2002200091 A | 7/2002 |
| JP | 2003024336 A | 1/2003 |
| JP | 2005288590 A | 10/2005 |
| JP | 2006061364 A | 3/2006 |
| JP | 2007229906 A | 9/2007 |
| JP | 2008528130 A | 7/2008 |
| JP | 2010220955 A | 10/2010 |
| JP | 2013011324 A | 1/2013 |
| KR | 20110032444 A | 3/2011 |
| WO | WO-9729690 A1 | 8/1997 |
| WO | WO-2005039835 A1 | 5/2005 |
| WO | WO-2006039092 A2 | 4/2006 |
| WO | WO-2007075864 A1 | 7/2007 |
| WO | WO-2007143859 A1 | 12/2007 |
| WO | WO-2010081050 A1 | 7/2010 |
| WO | WO-2011037394 A2 | 3/2011 |
| WO | WO-2011143022 A1 | 11/2011 |
| WO | WO-2011143024 A1 | 11/2011 |
| WO | WO-2012158449 A1 | 11/2012 |
| WO | WO-2012166806 A1 | 12/2012 |
| WO | WO-2015023730 A1 | 2/2015 |
| WO | WO-2015023834 A1 | 2/2015 |
| WO | WO-2015142290 A1 | 9/2015 |

OTHER PUBLICATIONS

Article 94(3) Communication in EP Application No. 14836832.7, dated Jul. 23, 2019.
Office Action for U.S. Appl. No. 14/911,529, dated Jul. 8, 2019, 8 pages.
Office Action for JP Application No. 2019-052645, dated Mar. 10, 2020.
Extended European Search Report for Application No. EP19195298.5 dated Nov. 12, 2019, 10 pages.
Office Action dated Jan. 26, 2021 for Japanese Application No. 20190074699 filed Apr. 10, 2019, 6 pages.
Office Action for JP Application No. 2019-074698, dated Jun. 23, 2020, 12 pages.
Office Action for JP Application No. 2019-074699, dated Jun. 23, 2020, 7 pages.
Office Action for CN Application No. 2018106271734, dated Jul. 15, 2020, 17 pages.
Extended European Search Report for EP Application No. 20179278. 5, dated Sep. 16, 2020, 9 pages.
Office Action for CN Application No. 2018115675563, dated Nov. 24, 2020, 15 pages.
Office Action for KR Application No. 10-2016-7006755, dated Jan. 6, 2021, 6 pages.
Office Action for KR Application No. 10-2016-7006762, dated Jan. 11, 2021, 8 pages.
International Search Report and Written Opinion for Application No. PCT/US14/050838, dated Nov. 25, 2014, 11 pages.
International Search Report and Written Opinion for Application No. PCT/US14/50957, dated Nov. 21, 2014, 11 pages.
International Search Report and Written Opinion for Application No. PCT/US14/51001, dated Nov. 20, 2014, 11 pages.
International Search Report and Written Opinion for Application No. PCT/US14/51074, dated Nov. 20, 2014, 13 pages.
International Search Report and Written Opinion for Application No. PCT/US2012/037269, dated Sep. 19, 2012, 10 pages.
International Search Report and Written Opinion for Application No. PCT/US2014/051033, dated Nov. 19, 2014, 9 pages.
International Search Report and Written Opinion for Application No. PCT/US2014/051050, dated Nov. 25, 2014, 14 pages.
Office Action for U.S. Appl. No. 14/911,514, dated Aug. 10, 2018, 8 pages.
Office Action dated Dec. 26, 2014 for Japanese Application No. 20140021913 filed Feb. 7, 2008, 10 pages.
Office Action dated Sep. 30, 2015 for Japanese Application No. 20140021913 filed Feb. 7, 2008, 7 pages.
Extended European Search Report for Application No. 14836283.3, dated Sep. 4, 2017, 11 pages.
Extended European Search Report for Application No. 14836336.9, dated Jun. 16, 2017, 9 pages.
Extended European Search Report for Application No. 14836512.5, dated Aug. 3, 2017, 13 pages.
Extended European Search Report for Application No. 14836696.6, dated Jun. 16, 2017, 9 pages.
Office Action dated Nov. 30, 2016 for Chinese Application No. 201510185999.6 filed Sep. 2, 2009, 24 pages.
Extended European Search Report for Application No. 14836832.7, dated Jun. 9, 2017, 8 pages.
Extended European Search Report for Application No. EP14836874. 9, dated Mar. 17, 2017, 10 pages.
Partial Supplementary European Search Report for Application No. EP14836283.3, dated May 17, 2017, 12 pages.
Office Action dated Jun. 22, 2017 for Japanese Application No. 2016177316 filed Sep. 12, 2016, 7 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action for CN Application No. 201810977726.9, dated Aug. 25, 2020, 19 pages.
Office Action for CN Application No. 201910034292.3, dated Nov. 4, 2020, 35 pages.
Office Action for U.S. Appl. No. 16/890,555, dated Nov. 10, 2020, 8 pages.
Office Action for JP Application No. 2020-103520, dated May 11, 2021, 10 pages.

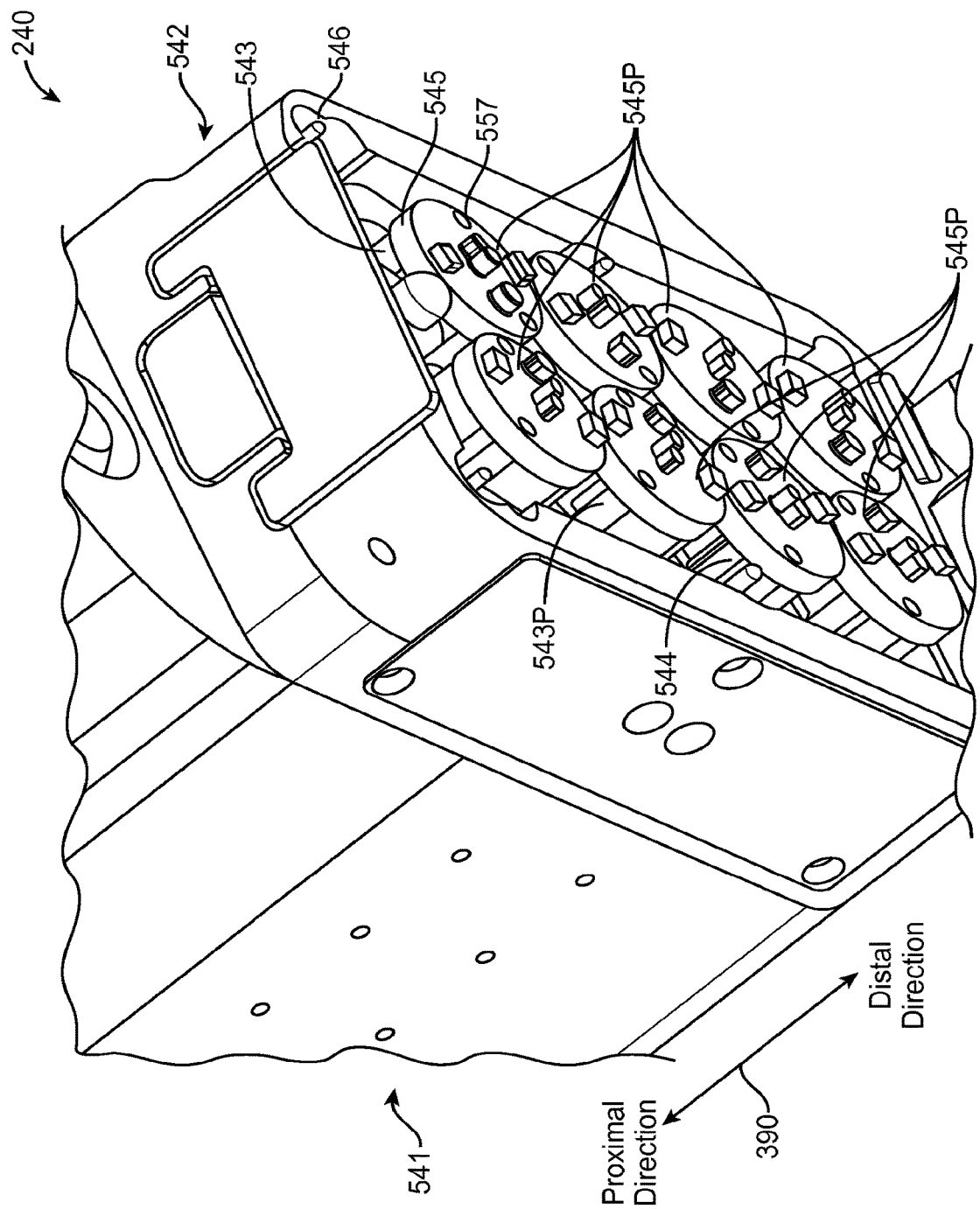

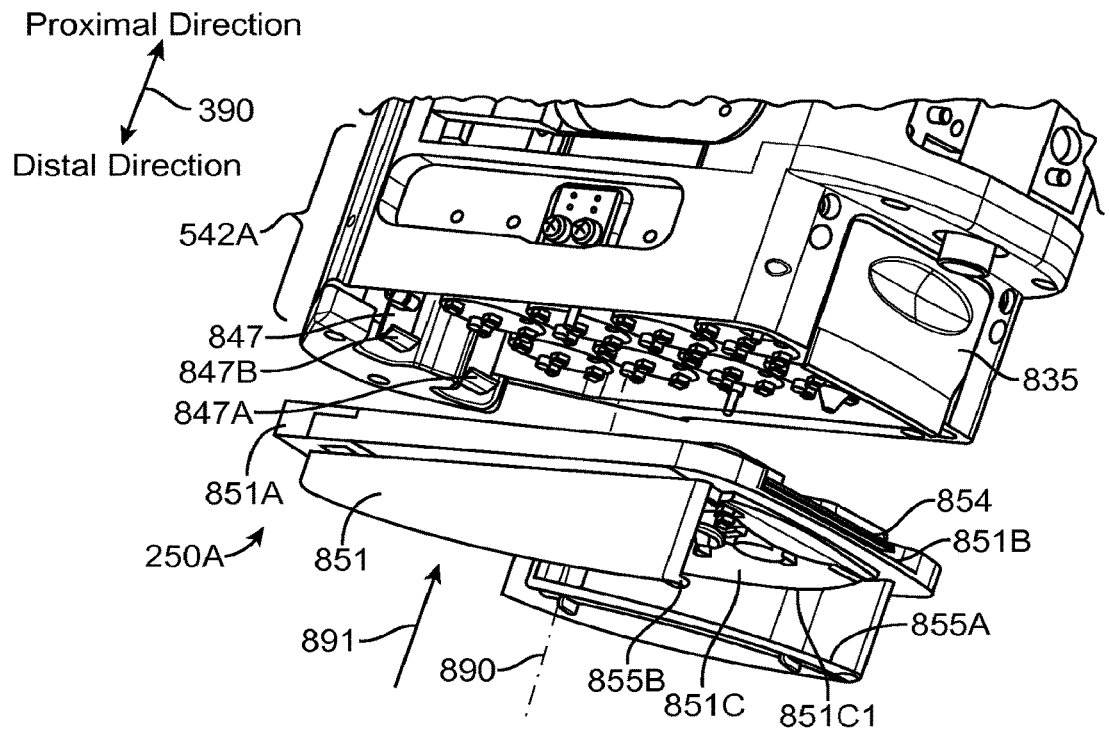
FIG. 8A
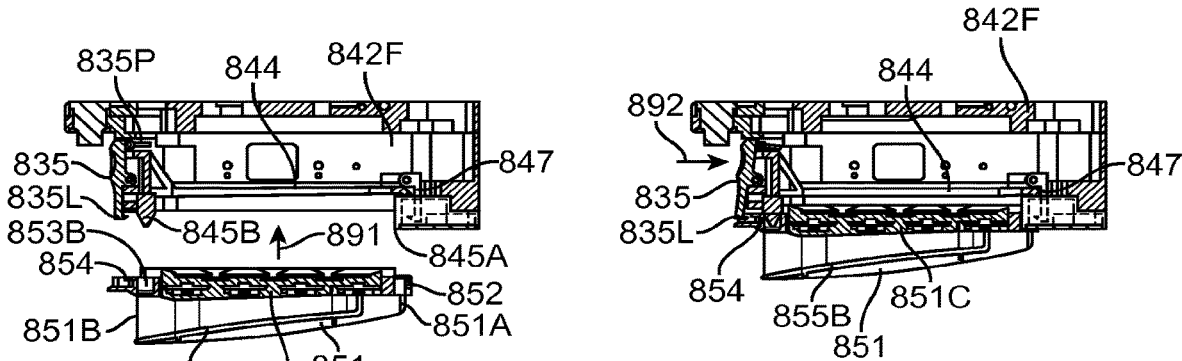
FIG. 8B
FIG. 8C
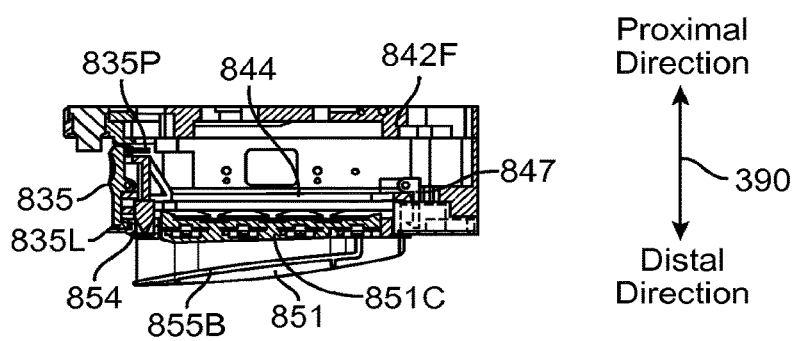
FIG. 8D

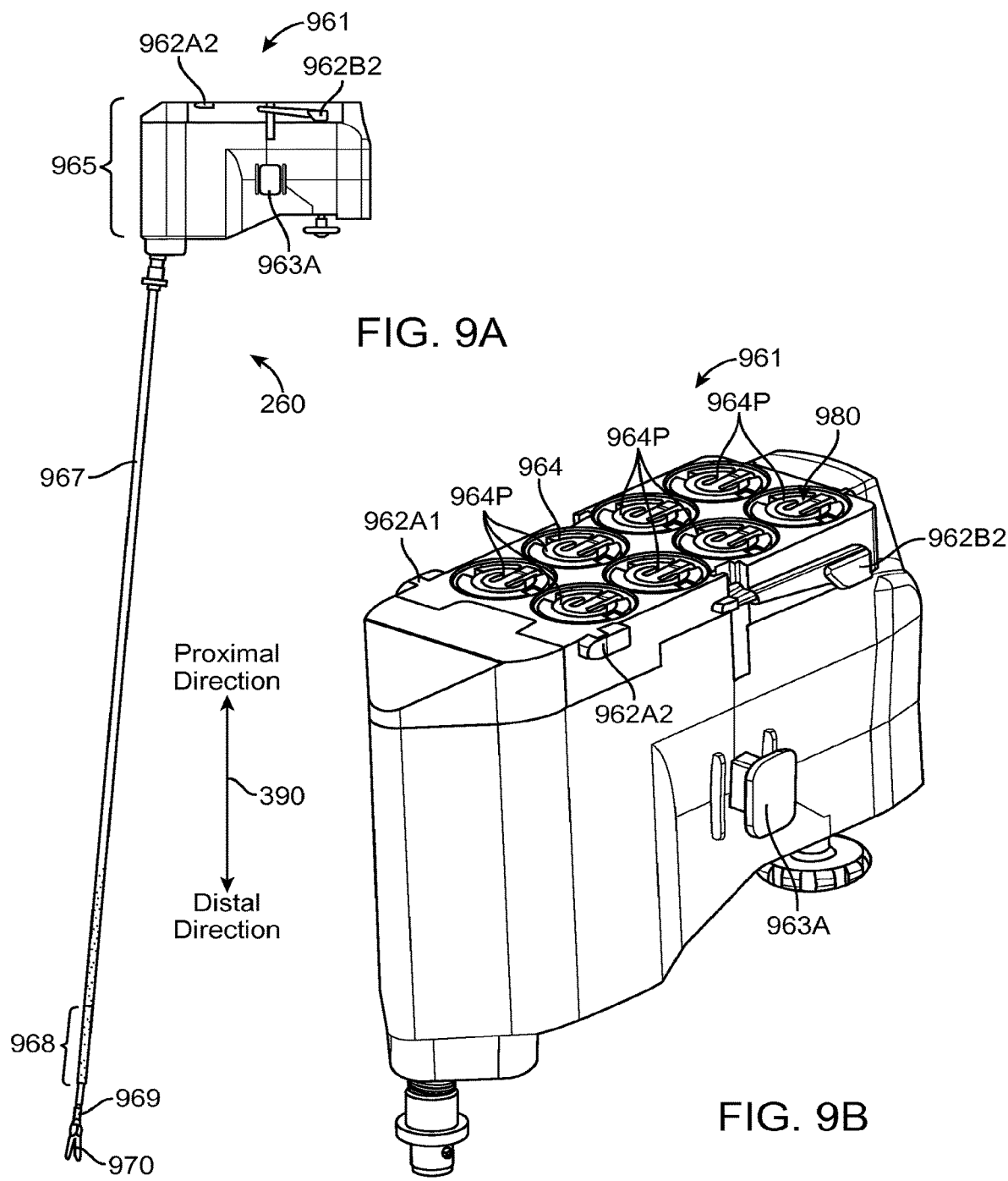

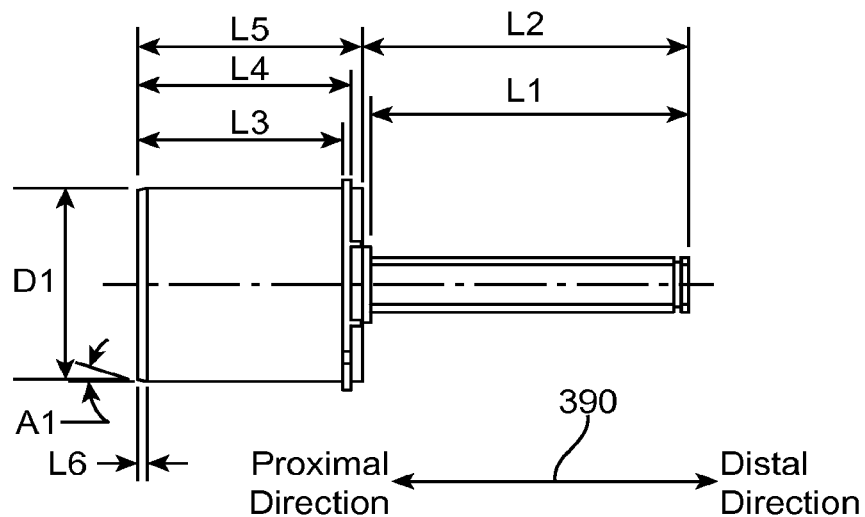
FIG. 15B
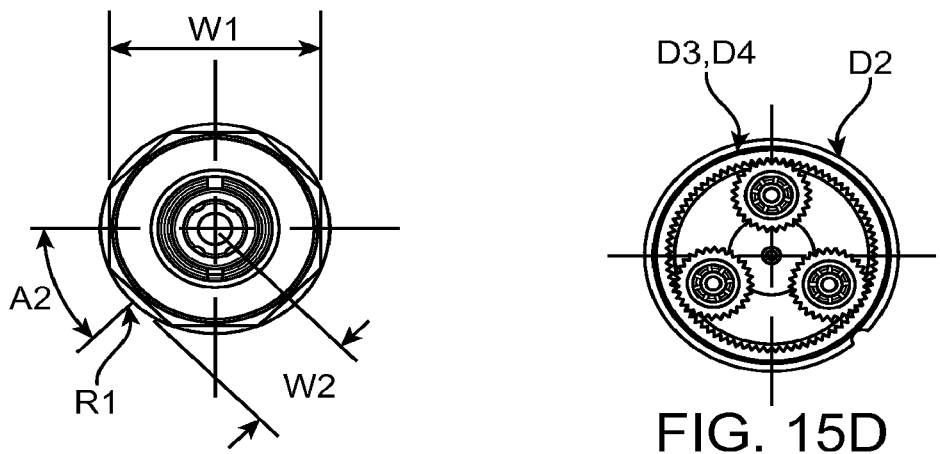
FIG. 15C
FIG. 15D
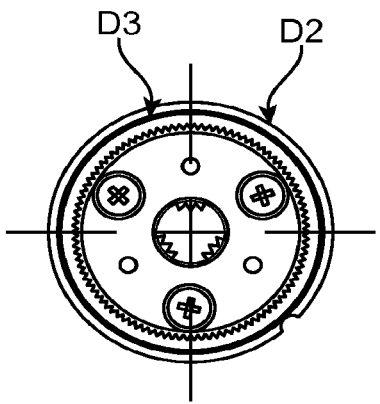
FIG. 15E

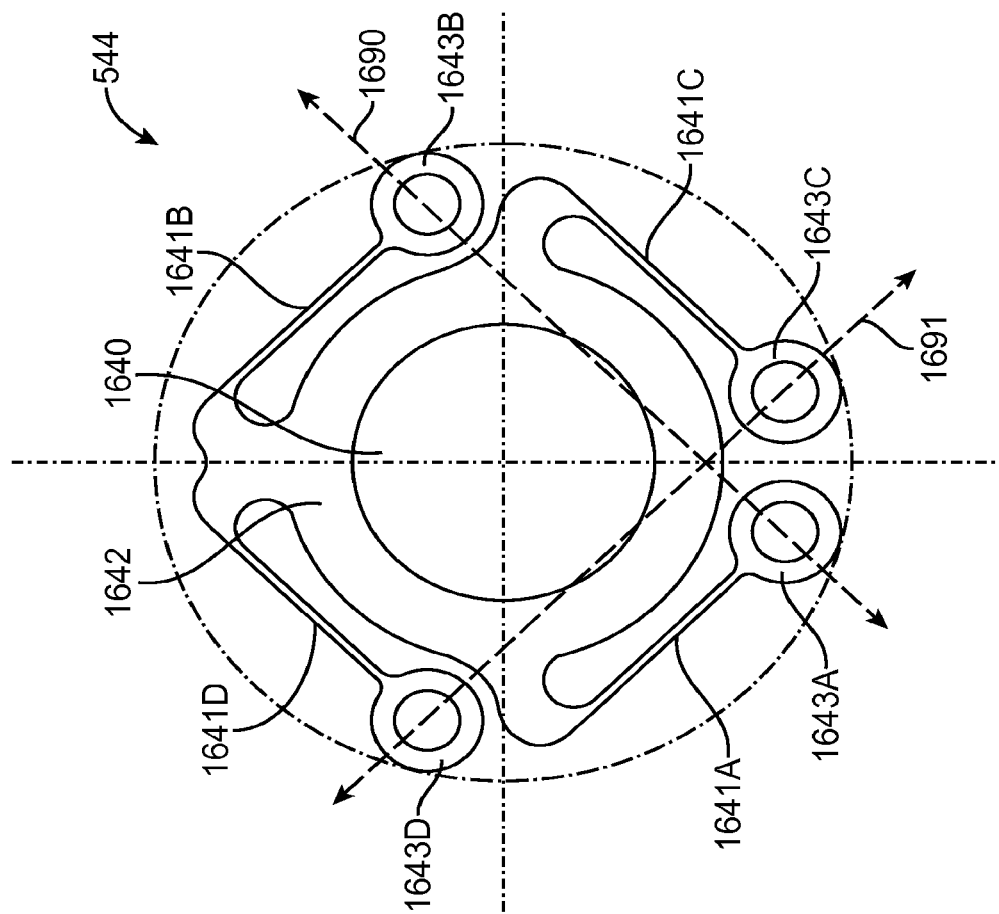
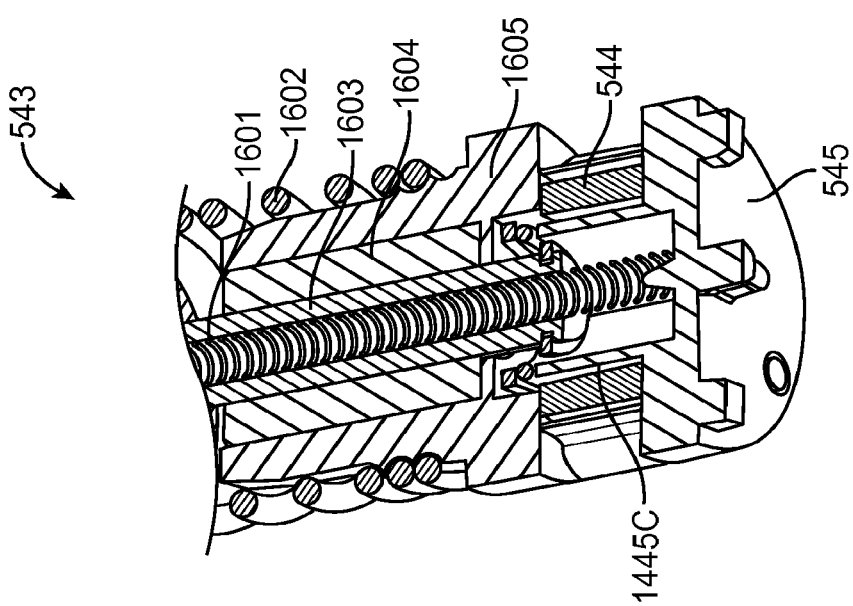
FIG. 16B
FIG. 16A

INSTRUMENT STERILE ADAPTER DRIVE INTERFACE

RELATED APPLICATIONS

This application is a continuation of U.S. patent application Ser. No. 14/911,510 (filed Feb. 11, 2016)(entitled "INSTRUMENT STERILE ADAPTER DRIVE FEATURES"), which is a U.S. national phase of International Application No. PCT/US2014/051050 (filed Aug. 14, 2014) (entitled "INSTRUMENT STERILE ADAPTER DRIVE FEATURES"), which designated the U.S. and which claims priority to and the benefit of U.S. Patent Application No. 61/866,124 (filed Aug. 15, 2013)(entitled "INSTRUMENT STERILE ADAPTER DRIVE FEATURES"), each of which is incorporated herein by reference in its entirety.

BACKGROUND

Field of the Invention

The present invention relates generally to surgical instruments and systems, and more particularly to surgical instruments with low backlash drive systems.

Description of Related Art

Robotically controlled systems such as employed for minimally invasive medical procedures can include large and complex equipment to precisely control and drive relatively small tools or instruments. (As used herein, the terms "robot" or "robotically" and the like include teleoperation or telerobotic aspects.) FIG. 1A illustrates an example of a known robotically controlled system 100. System 100, which may, for example, be part of a da Vinci® Surgical System commercialized by Intuitive Surgical, Inc., includes a patient-side cart 110 having multiple arms 130. Each arm 130 has a docking port 140 that generally includes a drive system with a mechanical interface for mounting and providing mechanical power for operation of an instrument 150. Arms 130 can be used during a medical procedure to move and position respective medical instruments 150 for the procedure.

FIG. 1B shows a bottom view of a known instrument 150. Instrument 150 generally includes a transmission or backend mechanism 152, a main tube 154 extending from the backend mechanism 152, and a functional tip 156 at the distal end of the main tube 154. Tip 156 generally includes a medical tool such as a scalpel, scissors, forceps, or a cauterizing instrument that can be used during a medical procedure. Drive cables or tendons 155 connected to tip 156 and extend through main tube 154 to backend mechanism 152. Backend mechanism 152 typically provides a mechanical coupling between the drive tendons of the instrument 150 and motorized axes of the mechanical interface of a drive system 140. In particular, gears or disks 153 have features such as projections or holes that are positioned, sized, and shaped to engage complementary features on the mechanical interface of a drive system 140. In a typical instrument, rotation of disks 153 pulls on respective tendons 155 and actuates corresponding mechanical links in tip 156. System 100 can thus control movement and tension in drive tendons 155 as needed to position, orient, and operate tip 156. Further details of known surgical systems are described, for example, in U.S. Pat. No. 7,048,745 (filed Aug. 13, 2001) to Tierney et al., entitled "Surgical Robotic Tools, Data Architecture, and Use," which is hereby incorporated by reference in its entirety.

Instruments 150 of system 100 can be interchanged by removing one instrument 150 from a drive system 140 and then installing another instrument 150 in place of the instrument removed. The installation process in general requires that the features on disks 153 properly engage complementary features of drive system 140. However, before installation, the orientations of disks 153 on instrument 150 are generally unknown to patient-side cart 110.

Further, equipment such as patient-side cart 110 is often covered for a medical procedure by a sterile barrier (e.g., a plastic sheet drape) because of the difficulty in cleaning and sterilizing complex equipment between medical procedures. This sterile barrier can include a sterile adaptor that is interposed between docking port 140 and instrument backend 152. See for example, U.S. Pat. Nos. 7,048,745 and 7,699,855 (filed Mar. 31, 2006) to Anderson et al., entitled "Sterile Surgical Adaptor", which is hereby incorporated by reference in its entirety, describe some exemplary sterile barrier and adaptor systems.

A typical installation process for an instrument 150 involves mounting backend mechanism 152 without regard for the orientations of disks 153 on a drive system 140, possibly with an intervening sterile adaptor. The drive motors in drive system 140 may be then be rotated back and forth multiple times during the installation procedure to ensure that the complementary features mesh with and securely engage each other for operation of the newly installed instrument 150. At some point during the installation process, the drive motors become securely engaged to rotate respective disks 153. However, the instrument 150 being installed may move in an unpredictable manner at times during the installation procedure because the drive motors positively engage respective disks 153 of instrument 150 at different and unpredictable times. For certain applications, such unpredictable motion is unacceptable. In general, clear or confined space is required around an instrument 150 to accommodate random movements of the instrument tip during an installation procedure.

SUMMARY

A surgical system includes a surgical instrument that is sensitive to backlash that would adversely affect the transmission of controlled torque and position to the surgical instrument. The surgical instrument is coupled to motors in a surgical instrument manipulator assembly via a mechanical interface. The combination of the mechanical interface and surgical instrument manipulator assembly has a low backlash, e.g. less than 0.7 degrees. The mechanical interface couples a drive interface in the surgical instrument manipulator assembly to a driven interface of the surgical instrument. The mechanical interface has zero backlash for torque levels used in surgical procedures, in one aspect.

Thus, an apparatus includes a surgical instrument manipulator assembly. The surgical instrument manipulator assembly includes a drive unit and a drive output assembly. The drive output assembly is coupled to the drive unit. The drive output assembly includes a low backlash coupler coupled to the drive unit. A drive output disk is coupled to the low backlash coupler. A portion of the surgical instrument manipulator assembly backlash is in the coupling of the drive unit and the drive output disk to the low backlash coupler.

In one aspect, the drive output disk is a cylindrical body with a distal end surface. A first alignment element extends from the distal end surface. A second alignment element also extends from the distal end surface. The first alignment element is separated from the second alignment element. The combination of the first and second alignment elements orients the drive output disk to a disk of another assembly in the apparatus when the drive output disk and the disk are mated. In one aspect, the first alignment element is a pin, and the second alignment element is a tab.

In this aspect, the distal end surface of the drive output disk has a center and a circumferential edge. A plurality of drive dogs extend from the distal end surface. Each drive dog includes a first edge surface positioned a first distance from the center, and a second edge surface positioned about adjacent to the circumferential edge. The second edge surface is opposite the first edge surface. Further, each drive dog includes a first portion that is a three-dimensional structure, e.g., a three-dimensional rectangle, which extends from the distal end surface and a second portion that extends from the first portion. The second portion has two opposing second portion side surfaces. Each of the second portion side surfaces is curved surface. In one aspect, the curved surface is a portion of a circular section, e.g., a portion of an outer surface of a cylinder.

The drive output assembly also includes a shaft. A first preload spring is coupled to the shaft. The first preload spring also is coupled to the drive output disk. The first preload spring is configured to apply a first preload force on the drive output disk when the first preload spring is compressed.

The drive output assembly also includes a second preload spring coupled to the shaft. The second preload spring in combination with the first preload spring is configured to apply a second preload force on the drive output disk when the first and second preload springs are compressed. The second preload force is larger than the first preload force.

The surgical instrument manipulator assembly includes a motor pack including a plurality of drive units. The plurality of drive units includes the drive unit described previously. The motor pack is moveably mounted in a housing of the surgical instrument manipulator assembly. The motor pack also includes a plurality of hard stops. The plurality of hard stops is configured to extend from a distal face of the motor pack.

The surgical instrument manipulator assembly also includes a release latch. The release latch is pivotally mounted in the housing of the surgical instrument manipulator assembly. A pin extends inside the housing from a proximal portion of the release latch. In one aspect, the pin is a spring-loaded pin.

The motor pack of the surgical instrument manipulator assembly also includes a release latch inhibit stop. If the motor pack is at a fully withdrawn position relative to the housing of the surgical instrument manipulator assembly, operation of the release latch is not inhibited, in one aspect. However, if the motor pack is at a first position relative to the housing, the pin contacts the release latch inhibit stop and prevents pivoting of the release latch if the release latch is pressed. In another aspect, the release latch inhibit stop prevents pivoting of the release latch when the motor pack is at the fully withdrawn position while a surgical instrument is mounted in the sterile adapter assembly.

In another aspect, the apparatus includes a surgical device assembly, a preload track, and a preload assembly riding on the preload track. The preload assembly is coupled to the surgical device assembly. An insertion assembly includes the preload track.

When the preload assembly is positioned at a first location on the preload track, the preload assembly applies a first force to the surgical device assembly. When the preload assembly is positioned at a second location on the preload track, the preload assembly applies a second force to the surgical device assembly. The second force is larger than the first force.

In one aspect, the preload assembly includes a cam follower assembly and an arm. The cam follower assembly rides on the preload track. The arm has a first end and a second end. The first end is coupled to the surgical device assembly. The second end of the arm is coupled to the cam follower assembly. If the cam follower assembly is positioned at the first location on the preload track, the arm is configured to transfer a force proportional to the first force from the cam follower assembly to the surgical device assembly. If the cam follower assembly is positioned at the second location on the preload track, the arm is configured to transfer a force proportional to the second force from the cam follower assembly to the surgical device assembly.

The surgical device assembly also includes a drive unit housing and a motor pack. The motor pack is movably mounted in the drive unit housing. The first end of the arm is coupled to the motor pack. If the cam follower assembly is positioned at the first location on the preload track, the arm is configured to transfer a force proportional to the first force from the cam follower assembly to the motor pack. If the cam follower assembly is positioned at the second location on the preload track, the arm is configured to transfer a force proportional to the second force from the cam follower assembly to the motor pack.

In another aspect, an apparatus includes a preload track and a preload assembly configured to ride on the preload track. The preload assembly is configured to couple to a surgical device assembly. The preload assembly also is configured to apply a first force to the surgical device assembly if the preload assembly is positioned at a first location on the preload track.

The preload assembly includes a preload reset mechanism. The preload reset mechanism is configured to automatically position the preload assembly at the first location on the preload track.

In yet another aspect, an apparatus includes a surgical instrument manipulator assembly, an insertion assembly, and a preload assembly. The surgical instrument manipulator assembly includes a housing and a motor pack. The motor pack is movably mounted in the housing. The insertion assembly is coupled to the surgical instrument manipulator assembly. The insertion assembly also includes a preload track. The preload assembly includes a cam follower assembly, an arm, and a preload rest assembly. The arm includes a first end and a second end. The first end of the arm is rotatably connected to the cam follower assembly. The second end of the arm is coupled to the motor pack. The cam follower assembly is configured to ride on the preload track. The preload reset assembly is configured to automatically position the preload assembly at a first location on the preload track. At the first location, the preload assembly applies a first force on the motor pack.

Another apparatus includes an insertion assembly, an instrument manipulator assembly, a surgical device interface, and a surgical instrument. Sometimes, the surgical device interface is referred to as a surgical device interface element. The insertion assembly includes a distal end and a preload track. The instrument manipulator assembly is coupled to the distal end of the insertion assembly. The instrument manipulator assembly includes a drive output disk. The drive output disk has a drive output interface.

The surgical device interface is mounted on the instrument manipulator assembly. The surgical device interface includes an intermediate disk. The intermediate disk has an intermediate driven interface and an intermediate drive interface. The intermediate driven interface is coupled to the drive output interface.

The surgical instrument is mounted on the surgical device interface. The surgical instrument includes a driven disk. The driven disk has a driven interface. The driven interface is coupled to the intermediate drive interface.

If a first force is applied to the coupling between the drive output disk and the intermediate disk, the coupling between the drive output disk and the intermediate disk has non-zero backlash for torque levels used to bring the two disks into alignment. If a second force is applied to the coupling between the drive output disk and the intermediate disk, the coupling between the drive output disk and the intermediate disk has zero backlash for torque levels used in surgical procedures. The second force is larger than the first force.

Thus, the apparatus includes a drive output disk and an intermediate disk. The drive output disk includes a distal end surface and a plurality of drive dogs extending from the distal end surface. Each drive dog of the plurality of drive dogs includes a first portion that is a three-dimensional structure, e.g., a three-dimensional rectangle, which extends from the distal end surface, and a second portion extending from the first portion. The second portion includes two opposing second portion side surfaces. Each of the second portion side surfaces is a curved surface. In one aspect, the curved surface is a portion of a circular section, e.g., a portion of an outer surface of a cylinder. The intermediate disk includes a proximal end surface, and a plurality of drive dog receptacles extending from the proximal end surface into the intermediate disk. Each drive dog receptacle of the plurality of drive dog receptacles is configured to receive one of the plurality of drive dogs. Each drive dog receptacle of the plurality includes a first portion that includes opposed sidewalls extending from the outer surface into the intermediate disk, a second portion is a bottom surface of the drive dog receptacle, and a third portion extending from the first portion to the second portion. The third portion has two opposing third portion sloped side surfaces.

The apparatus has a first preload spring coupled to the drive output disk. The first preload spring is compressed when the drive output disk is coupled to the intermediate disk. The compression of the first preload spring applies a preload force to the drive output disk. When the preload force is applied to the drive output disk, the coupling between the drive output disk and the intermediate disk has non-zero backlash for torque levels necessary to bring the disks into alignment.

The apparatus also includes a second preload spring coupled to the drive output disk. A preload assembly is coupled to the first and second preload springs. When the preload assembly compresses the first and second preload springs, the compressed second spring in combination with the compressed first spring applies a second preload force to a coupling between the drive output disk and the intermediate disk. When the second preload force is applied to the coupling, the coupling between the drive output disk and the intermediate disk has zero backlash for torque levels used in surgical procedures.

In still another aspect, the apparatus includes a surgical device interface element. The surgical device interface element includes a plurality of intermediate disks and a first body structure having rotatably mounted therein the plurality of intermediate disks.

Each intermediate disk includes an intermediate driven interface and an intermediate drive interface. The intermediate drive interface is opposite from the intermediate driven interface.

The intermediate driven interface includes a first alignment receptacle and drive dog receptacles. The intermediate drive interface includes drive dogs and an engagement structure.

The first alignment receptacle is configured to mate with a first alignment element extending from a drive output disk of a surgical instrument manipulator assembly. The intermediate driven interface also includes a second alignment receptacle. The second alignment receptacle is configured to mate with a second alignment element extending from the drive output disk. The first alignment receptacle is separated from the second alignment receptacle. The combination of the first and second alignment receptacles orients the drive output disk to the intermediate disk when the drive output disk and the intermediate disk are coupled, e.g., mated.

The first body structure includes a plurality of hard stops. Each intermediate disk is associated with one of the hard stops. Each intermediate disk has a hard stop tab extending from an outer side surface of that disk. In a first axial position of the intermediate disk, the hard stop tab contacts the hard stop associated with the intermediate disk when the intermediate disk is rotated. In a second axial position of the intermediate disk, the intermediate disk rotates freely without the hard stop tab contacting the hard stop associated with the intermediate disk.

Each of the drive dog receptacles includes a first portion having opposed sidewalls extending from an outer surface of the intermediate disk into the intermediate disk. A second portion of the drive dog receptacle is a bottom surface of the drive dog receptacle. A third portion of the drive dog receptacle extends from the first portion to the second portion. The third portion includes two opposing third portion side surfaces. Each of the third portion side surfaces is a sloped surface. In one aspect, the sloped surface is a portion of a side surface of a wedge.

Each of the drive dogs of the intermediate disk has a first portion that is a three-dimensional structure, e.g., a three-dimensional rectangle. A second portion of the drive dog extends from the first portion. The second portion has two opposing second portion side surfaces. Each of the second portion side surfaces is a portion of curved surface. In one aspect, the curved surface is a portion of a circular section, e.g., a portion of an outer surface of a cylinder.

Each of the drive dog receptacles of the intermediate disk is positioned so that each of the drive dog receptacles is bisected by a first plane. Each of the drive dogs of the intermediate disk is positioned so that each of the drive dogs is bisected by a second plane. The first plane is perpendicular to the second plane.

The surgical device interface element also includes a second body structure. The first body structure is movably mounted in the second body structure. The second body structure includes a skid plate.

The intermediate disk also has a distal surface. The engagement structure, in one aspect, is an open three-dimensional structure extending in a distal direction from the distal surface. The open three-dimensional structure is a generally C-shaped structure. The C-shaped structure has a height, a first end, and a second end. The first and second ends bound an opening of the C-shaped structure. A centerline extends through a center of the C-shaped structure. The centerline is equidistance from the first and second ends.

The open three-dimensional structure also includes a wall extending from one of the first and second ends. The wall extends in a direction substantially parallel to the centerline of the C-shaped structure. The wall also extends towards an outer edge of the distal surface of the intermediate disk. The wall has a height that is smaller than the height of the C-shaped structure.

In another aspect, the open three-dimensional structure is a circular track. The circular track includes a first circumferential section having a first height, a first end, and a second end. The circular track also includes a second circumferential section extending between the first and second ends of the first circumferential section. The second circumferential section has a second height. The second height is less than the first height. A centerline of the circular tracks extends through a center of the circular track and is equidistance from the first and second ends. The C-shaped structure is an example of the circular track. In this aspect, the open three-dimensional structure also includes a wall extending in a direction substantially parallel to the centerline of the circular section from one of the first and second ends of the first circumferential section. The wall extends towards an outer edge of the distal surface of the intermediate disk of the plurality of intermediate disks. The wall has a height. The height of the wall is smaller than the first height of the first circumferential section.

In one aspect, the surgical device interface element is mounted on a surgical instrument manipulator assembly. The surgical instrument manipulator assembly includes a drive output disk having a drive interface. The drive interface is coupled with the intermediate driven interface of the intermediate disk. Upon applying a predetermined preload force to the drive output disk, the coupling between the intermediate disk and the drive output disk has zero backlash for torque levels used in surgical procedures.

In another aspect, a surgical instrument is mounted on the surgical device interface element. The surgical instrument further has a driven disk with a driven interface. The driven interface is coupled to the intermediate drive interface of the intermediate disk. Upon applying a predetermined preload force to the intermediate disk, the coupling between the intermediate disk and the driven disk has zero backlash for torque levels used in surgical procedures.

Thus, in one aspect, the apparatus includes an intermediate disk and a driven disk. The intermediate disk includes an intermediate driven interface and an intermediate drive interface. The intermediate drive interface is opposite from the intermediate driven interface.

The intermediate driven interface includes an alignment receptacle and drive dog receptacles. The intermediate drive interface includes drive dogs and an engagement structure.

The driven disk includes a driven interface configured to mate with the intermediate drive interface. The driven interface includes an engagement receptacle, drive dog receptacles, and a rotation disable element. The rotation disable element includes a rotation locking mechanism that prevents rotation of the driven disk. The engagement receptacle is configured to receive the engagement structure if the engagement structure is aligned with the engagement receptacle.

In still yet a further aspect, the apparatus includes a surgical instrument. The surgical instrument includes a body that has a driven disk receptacle. A proximal end of a shaft, which is in the surgical instrument, extends into the driven disk receptacle. A driven disk is mounted on the proximal end of the shaft so that the driven disk is positioned in the driven disk receptacle.

The driven disk includes a driven interface. The driven interface includes an engagement receptacle, drive dog receptacles, and a rotation disable element. The rotation disable element has a rotation locking mechanism. Upon engagement of the rotation disable element, the rotation locking mechanism engages the driven disk receptacle and prevents rotation of the driven disk.

Each of the drive dog receptacles includes a first portion, a second portion, and a third portion. The first portion includes opposed sidewalls extending from a proximal surface of the driven disk into the driven disk. The second portion is a bottom surface of the drive dog receptacle. The third portion extends from the first portion to the second portion. The third portion has two opposing third portion side surfaces. Each of the third portion side surfaces includes a sloped surface. In one aspect, the sloped surface is a portion of a side surface of a wedge. In one aspect, each drive dog receptacle includes a first edge surface positioned a first distance from a longitudinal axis of the driven disk, and a second open edge opposite the first edge.

The engagement receptacle includes a groove extending from a proximal surface of the driven disk into the driven disk. The groove extends from a first end to a second end. The groove has a width and a depth. The first end of the groove is separated from the rotation disable element by a first gap. The second end of the groove is separated from the rotation disable element by a second gap. The width and depth of the groove is sized to accept an engagement structure of an intermediate drive interface on an intermediate disk.

In one aspect, the rotation disable element is a flexure. The rotation locking mechanism extends from the flexure. In this aspect, the rotation locking mechanism includes a tang.

The driven disk receptacle has a bottom surface. A plurality of teeth extends in a proximal direction from the bottom surface.

The apparatus also includes a sterile adapter assembly. The surgical instrument is mounted on the sterile adapter assembly. The sterile adapter assembly includes an intermediate disk having an intermediate drive interface coupled with the driven interface of the driven disk. Upon applying a predetermined preload force to the intermediate disk, the coupling between the intermediate disk and the driven disk has zero backlash.

The apparatus also includes a surgical instrument manipulator assembly. The sterile adaptor assembly is mounted on the surgical instrument manipulator assembly. The surgical instrument manipulator assembly further includes a drive output disk having a drive interface coupled with the driven interface of the intermediate disk. Upon applying the predetermined preload force to the drive output disk, the coupling between the intermediate disk and the drive output disk has zero backlash for torque levels used in surgical procedures.

BRIEF DESCRIPTION OF THE DRAWINGS

FIG. 5 illustrates a distal end of the surgical instrument manipulator assembly of FIG. 2.

FIG. 8A illustrates another aspect of a drive output unit and a sterile adapter assembly.

FIGS. 8B to 8D are cut-away drawings illustrating the coupling of the sterile adapter assembly of FIG. 8A to the drive output unit.

FIGS. 9A and 9B are more detailed illustrations of the surgical instrument of FIG. 2.

FIG. 15B is a side view of a planetary gearhead.

FIG. 15C is a distal view of the planetary gearhead.

FIG. 15D is a proximal view of a 28:1 planetary gearhead.

FIG. 15E is a proximal view of a 9:1 planetary gearhead.

FIG. 16A is a more detailed illustration of the drive output assembly.

FIG. 16B is an end view of the low backlash coupler.

Figure 1A:
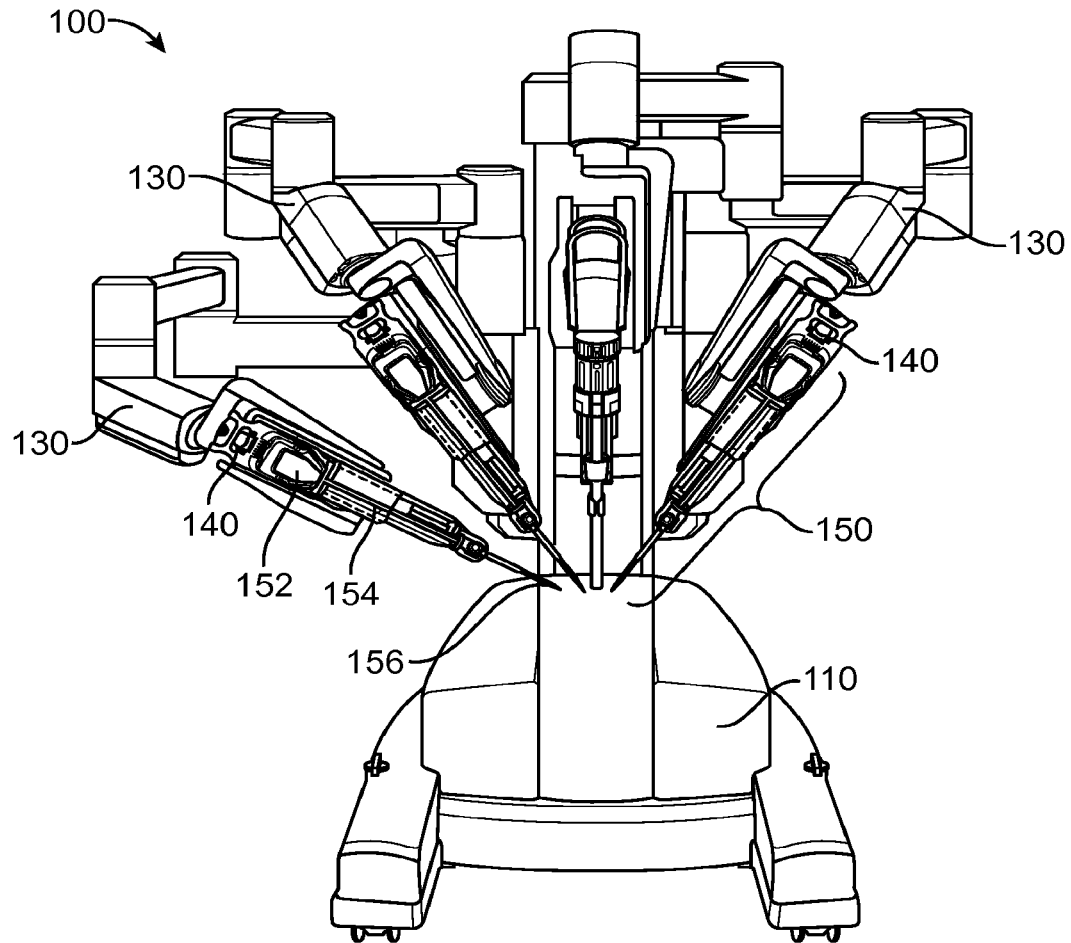
FIG. 1A is an illustration of a prior art teleoperated minimally invasive surgical system.
Figure 1B:
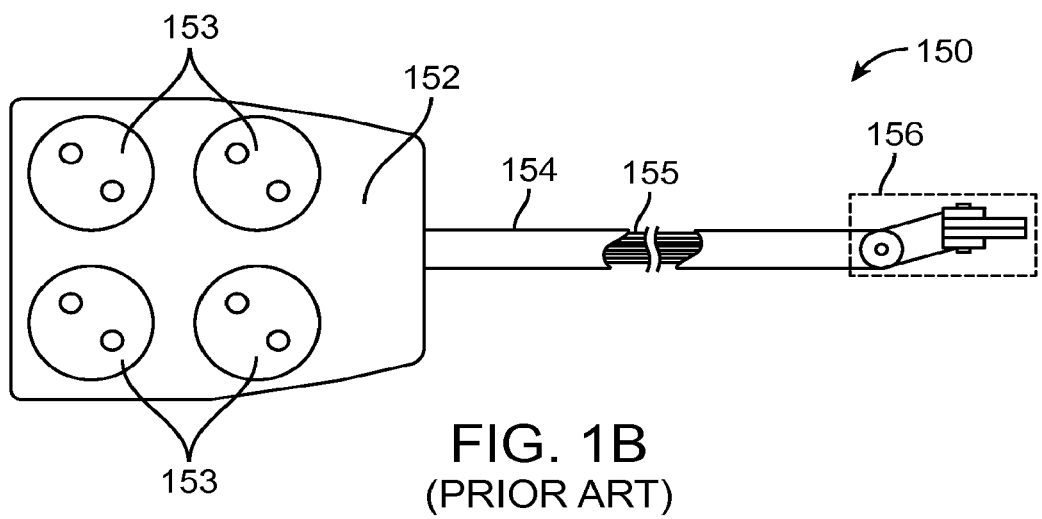
FIG. 1B is an illustration of a prior art surgical device assembly.

In the drawings, for single digit figure numbers, the first digit in the reference numeral of an element is the number of the figure in which that element first appears. For double-digit figure numbers, the first two digits in the reference numeral of an element is the number of the figure in which that element first appears.

DETAILED DESCRIPTION

Figure 2:
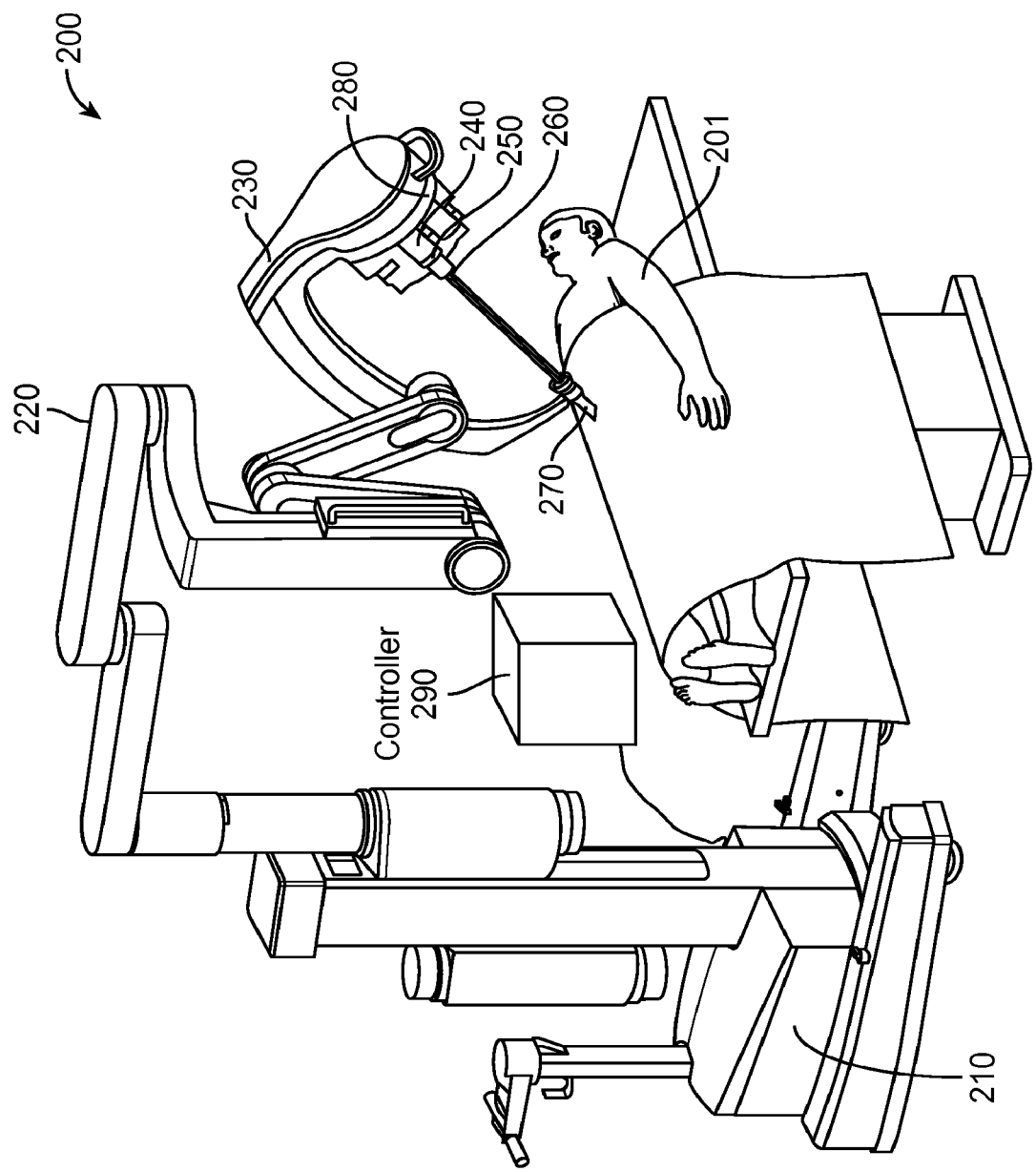
FIG. 2 is an illustration of a teleoperated surgical system that includes a surgical device assembly with a low backlash.

In one aspect, a surgical system 200 (FIG. 2), e.g., a minimally invasive teleoperated surgical system, includes a patient-side cart 210 having an arm 220. At an end of arm 220 is an entry guide manipulator 230. Mounted on entry guide manipulator 230 is a master instrument manipulator 280 that in turn supports multiple surgical device assemblies. In one aspect, a surgical device assembly includes a surgical instrument manipulator assembly 240, an instrument sterile adapter assembly 250, and a surgical instrument 260.

Surgical instrument manipulator assembly 240 is sometimes referred to as instrument manipulator assembly 240. Instrument sterile adapter assembly 250 is sometimes referred to as sterile adapter assembly 250.

Entry guide manipulator 230 changes the pitch and yaw of the surgical device assemblies as group. A main tube of each surgical instrument 260 extends through a different channel in a single port entry guide 270. Single port entry guide 270 is mounted in a cannula, in this aspect. Single port refers to a single access location (e.g., a single incision, a single natural orifice, and the like) to a surgical site inside the patient.

As used herein, a cannula is a tube that passes through the patient's body wall, and that comes in direct contact with the patient. The cannula generally does not slide in and out relative to the patient, but the cannula can pitch and yaw around a point on its axis called the remote center of motion.

As used herein, singe port entry guide 270 is a tube through which all surgical instruments and a camera instrument must pass to reach a location inside the patient. Entry guide 270 has separate lumens for each instrument. Entry guide 270 passes through the cannula, and may twist relative to the cannula.

As used here, backlash is a maximum angle through which one part of a mechanical interface can be moved without moving a connected part of the mechanical interface. Surgical instrument 260 is sensitive to backlash that would adversely affect the transmission of controlled torque and position from instrument manipulator assembly 240 to surgical instrument 260. As explained more completely below, surgical instrument 260 is coupled to motors in instrument manipulator assembly 240 via a mechanical interface. The combination of the mechanical interface and instrument manipulator assembly 240 has low backlash, e.g., less than 0.7 degrees. From the output disk (the drive output disk) in instrument manipulator assembly 240 to the input disk (the driven disk) of surgical instrument 260, the mechanical interface has zero backlash, in one aspect.

In one aspect, the mechanical interface includes sterile adapter assembly 250. Sterile adapter assembly 250 includes a sterile drape (not shown). The sterile drape is configured in a matter equivalent to the configurations known to those knowledgeable in the field. Sterile adapter assembly 250 is a single use product. Therefore, the portion of the mechanical interface implemented in sterile adapter assembly 250 includes a minimal number of parts, as described more completely below.

A transmission unit of surgical instrument 260 has multiple parallel input shafts. Due to manufacturing variations and tolerances, not all of these input shafts are or can be perfectly parallel or precisely located. For this reason, the mechanical interface must accommodate shaft angular and planar misalignment during the process of engaging surgical instrument 260 to instrument manipulator assembly 240. The mechanical interface couples surgical instrument 260 to the drive motors in instrument manipulator assembly 240 with very little, effectively zero, instrument tip motion during the instrument engagement process. As explained more completely below, until surgical instrument 260 is engaged with the motors in instrument manipulator assembly 240, instrument tip motion is inhibited. In addition, the distal end of surgical instrument 260 does not extend beyond the distal end of the cannula until the backlash in the mechanical interface has been minimized.

A controller 290 is coupled to a surgeon's control console (not shown) and to patient-side cart 210. Controller 290 represents the various controllers in system 200. Controller 290 sends control commands to the surgical instrument 260 in response to control commands. The control commands are based on movements of masters in a surgeon's control console by a surgeon. A display module in system controller 290 also updates a stereoscopic view of the surgical site generated by a display device in the surgeon's control console as slave surgical instrument 260 moves in response to the control commands.

Although described as controller 290, it is to be appreciated that controller 290 may be implemented in practice by any combination of hardware, software that is executed on a processor, and firmware. Also, its functions, as described herein, may be performed by one unit or divided up among different components, each of which may be implemented in turn by any combination of hardware, software that is executed on a processor, and firmware. When divided up among different components, the components may be centralized in one location or distributed across system 200 for distributed processing purposes. A processor should be understood to include at least a logic unit and a memory associated with the logic unit.

Figure 3:
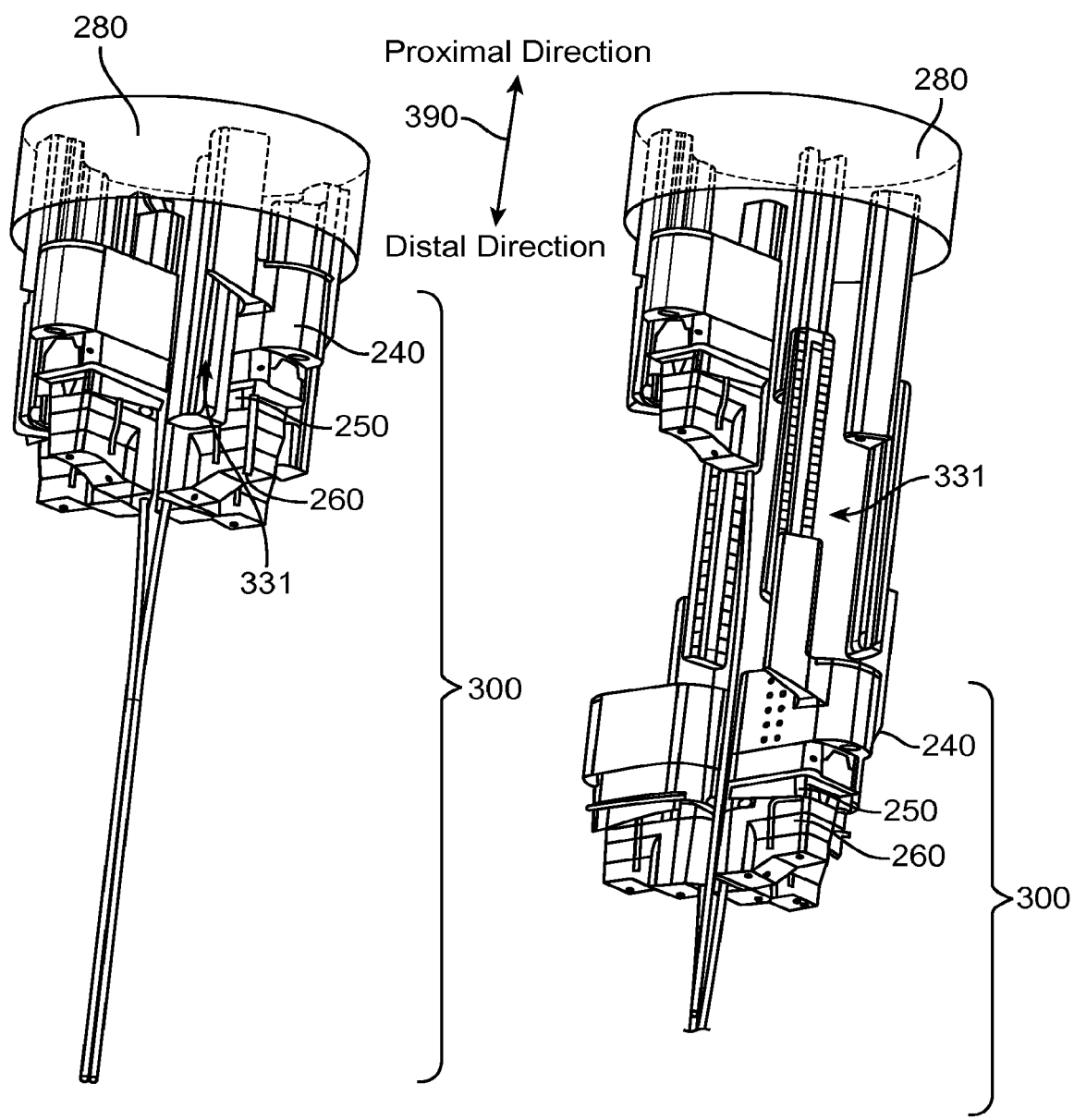
FIG. 3 is a more detailed illustration of the configuration of the surgical device assemblies in FIG. 2, where a surgical device assembly has a known backlash.

FIG. 3 illustrates four surgical device assemblies 300 mounted on entry guide manipulator 230. In FIG. 3, surgical device assemblies 300 are positioned at an initial position, e.g., a first location. As explained more completely below, the mechanical interface includes a disk stack between a motor in instrument manipulator assembly 240 and a shaft in the transmission unit of surgical instrument 260. In the configuration of FIG. 3, a first preload force is applied on the disk stack, e.g., a first predetermined force is applied on the disk stack.

With this first preload force, the mechanical interface may have some backlash because the first preload force is not sufficient to clamp the disks in the disk stack tightly enough together to prevent relative motion between the disks in the mechanical interface. However, the design of disks in the disk stack in the mechanical interface in combination with the first preload force ensures that the disks in the disk stack remain engaged, e.g., partially coupled, until the backlash is minimized.

With the first preload force, which is a low preload force, the disks in the mechanical interface have zero backlash up to a first torque level, e.g., 1.17 in-lb assuming a friction coefficient of 0.1. Above the first torque level, there may be a known small backlash, for example 1.13 degrees. Since, as described more completely below, a force sufficient to spin the disks to overcome friction and dynamically mate the disks quickly is used, this force typically provides more than the first torque level. In this instance, the disks in the mechanical interface have non-zero backlash. Thus, the mechanical interface is said to have non-zero backlash in this instance.

In FIG. 3, three of the four surgical device assemblies have been moved distally. Arrow 390 defines the distal and proximal directions. Here, the distal direction is towards patient 201 and away from master instrument manipulator 280. The proximal direction is away from patient 201 and towards master instrument manipulator 280.

As surgical device assembly 300 moves distally on insertion assembly 331, the preload force on the disk stack is automatically increased from the first preload force to a second preload force. The second preload force is an example of a second predetermined force. The second preload force reduces the backlash of the mechanical interface, i.e., the backlash between the disks in the disk stack, to zero for torque levels used in surgical procedures.

In one aspect, the second preload force is a high preload force, e.g., 2.3 lb. As just described, the disks in the mechanical interface, and hence the mechanical interface, have zero backlash at torque levels used in surgical procedures. In one example if the coefficient of friction is assumed to be 0.1, the mechanical interface has zero backlash for torque levels up to 4.9 in-lb. For surgical instrument 260 to apply surgically useful forces at the end effector a certain torque must be applied to the disks in the mechanical interface. This is deemed a surgically useful torque. In one example, a surgically useful torque may be 4.425 in-lb, and so the mechanical interface has zero backlash for torque levels used in surgical procedures in this aspect.

As explained more completely below, unlike the prior art, the control of the backlash is in instrument manipulator assembly 240. Previously, the backlash was controlled in a sterile adapter assembly that was disposable, which in one instance required that the sterile adapter assembly include injection-molded parts that had resilient properties. Moving control of the backlash into instrument manipulator assembly 240 allows use of machined parts, and so allows reduction of the backlash.

Figure 4A:
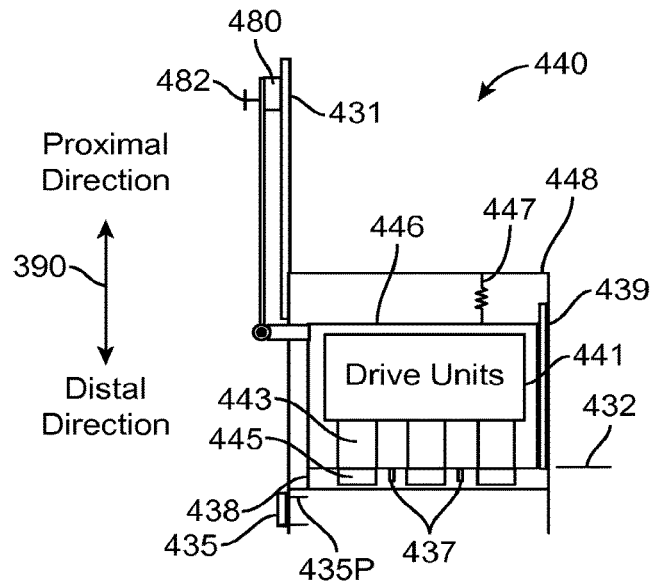
FIGS. 4A to 4G are block diagrams that illustrate the mounting of a sterile adapter assembly and a surgical instrument on a surgical instrument manipulator assembly, operation of preload mechanism to reduce backlash, instrument removal lockout, sterile adapter removal lockout, preload release, and automatic preload reset.
Figure 4B:
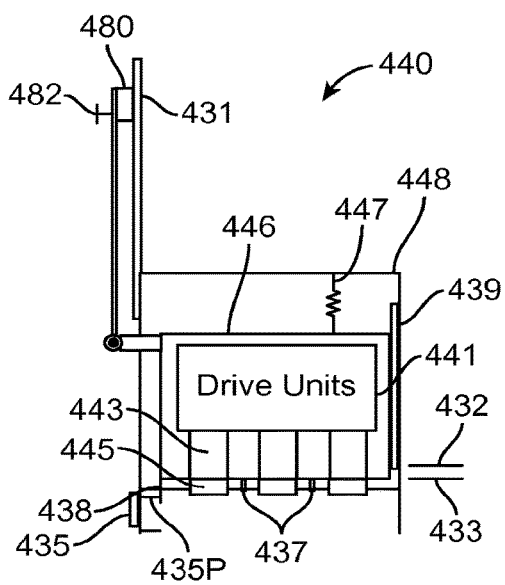
Figure 4C:
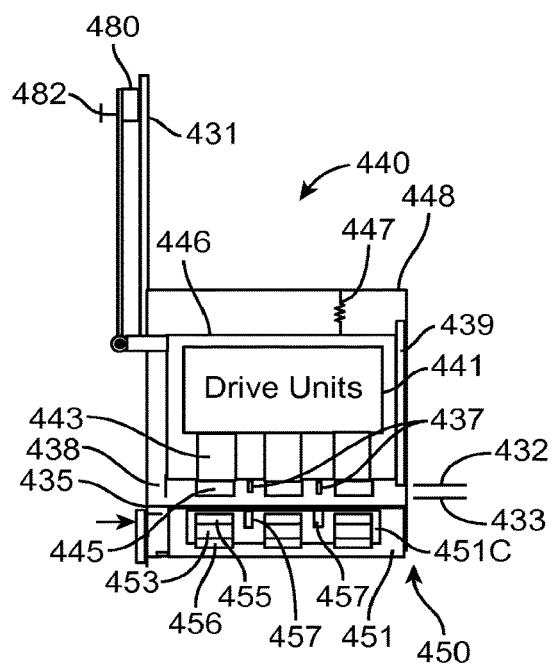
Figure 4D:
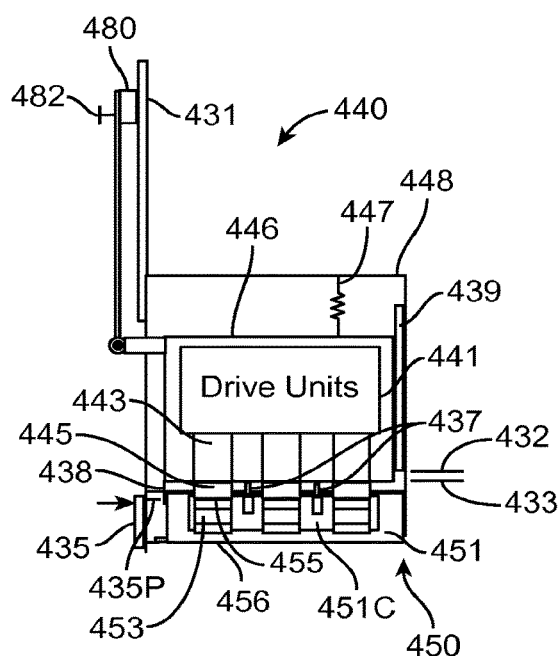
Figure 4E:
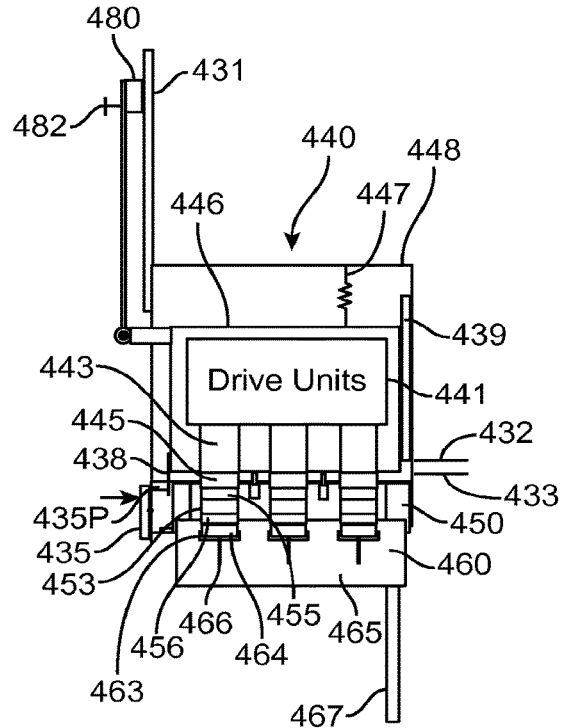
Figure 4F:
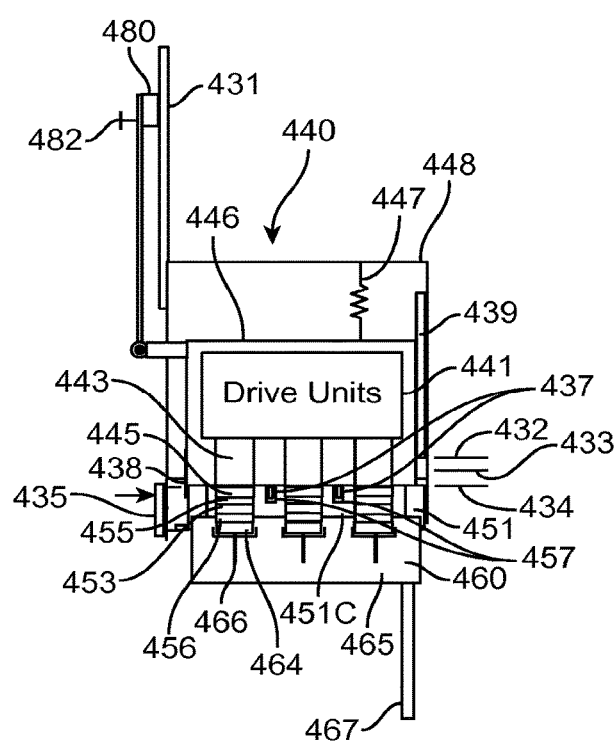
Figure 4G:
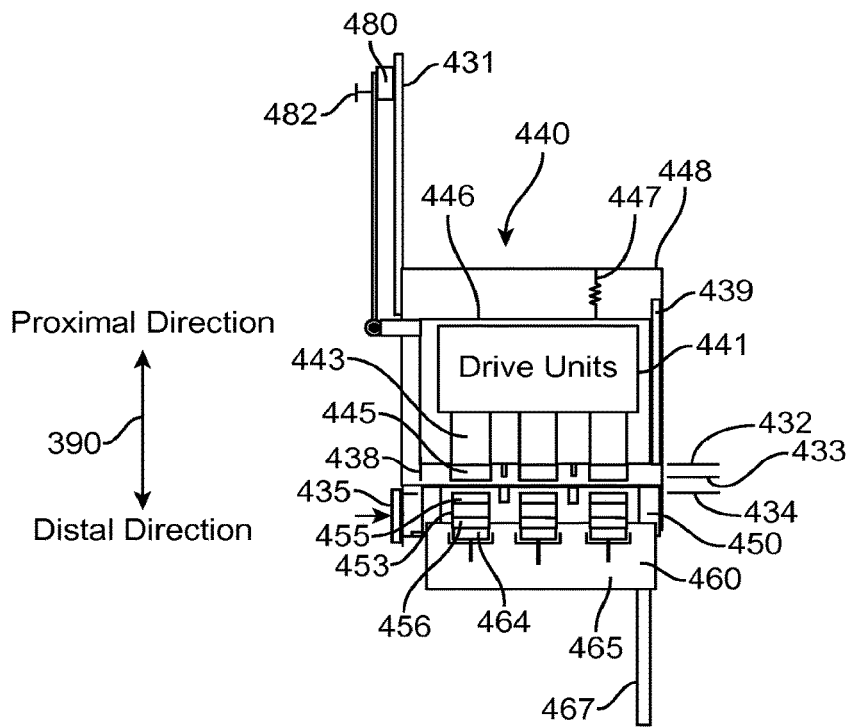

FIGS. 4A to 4G are block diagrams that illustrate the mounting of a sterile adapter assembly and a surgical instrument on a surgical instrument manipulator assembly. Other aspects illustrated in FIGS. 4A to 4G include operation of a preload mechanism to reduce backlash, instrument removal lockout, sterile adapter removal lockout, preload release, and automatic preload reset. FIGS. 4A to 4G are not to scale. Arrow 390 in FIGS. 4A and 4G shows the proximal and distal directions in each of FIGS. 4A to 4G.

FIG. 4A shows a surgical instrument manipulator assembly 440 affixed to insertion assembly 431. In particular, instrument manipulator assembly housing 448 is fixedly attached to a distal end of insertion assembly 431, and so instrument manipulator assembly housing 448 moves with movement of insertion assembly 431. However, a motor pack 446 within instrument manipulator assembly housing 448 can move on rail 439. Motor pack 446 can move in the distal and proximal directions relative to instrument manipulator assembly housing 448. Motor pack 446 is coupled to instrument manipulator assembly housing 448 by a return spring 447.

Motor pack 446 is movably coupled to insertion assembly 431 by preload assembly 480. Preload assembly 480 rides on a preload track in insertion assembly 431. As explained more completely below, as preload assembly 480 moves in the distal direction, preload assembly 480 provides a longitudinal force in the distal direction on motor pack 446. Preload assembly 480 includes a preload release button 482.

Motor pack 446 includes a plurality of drive units 441. Plurality of drive units 441 includes a plurality of drive motors and a plurality of drive output assemblies. Each drive motor in the plurality of drive motors is coupled to a corresponding drive output assembly 443 in the plurality of drive output assemblies.

Drive output assembly 443 includes a preload spring assembly and a drive output disk 445. Drive output assembly 443 also includes a low backlash coupler positioned between the preload spring assembly and drive output disk 445. Drive output disk 445 is coupled to the low backlash coupler by a set of input pins. As explained more completely below, drive output disk 445 is a cylindrical disk that includes a distal end surface. The distal end of each drive output disk 445 has a drive interface. The drive interface includes drive dogs and alignment elements.

The drive dogs extend in a distal direction from the distal end surface. Each drive dog includes a first portion comprising a three-dimensional structure, e.g., a three-dimensional rectangle, which extends from the distal end surface and a second portion extending from the first portion. The second portion of the drive dog includes two opposing second portion side surfaces, and each of the second portion side surfaces includes a curved surface. In one aspect, the curved surface is a portion of a circular section, e.g., a portion of an outer surface of a cylinder.

Motor pack 446 includes a plurality of hard stops 437 configured to extend from a distal face of motor pack 446, and motor pack 446 also includes a release latch inhibit stop 438. Release latch inhibit stop 438 extends in the distal direction from one side of motor pack 446. A release latch 435 is mounted in a wall of instrument manipulator assembly housing 448. A latch pin 435P is coupled to a proximal portion of release latch 435.

FIG. 4A shows instrument manipulator assembly 440 with the preload released, e.g., motor pack 446 is at a fully withdrawn position. In this configuration, return spring 447 retracts motor pack 446 within instrument manipulator assembly housing 448 so that the plurality of drive output disks including drive output disk 445 do not extend from a distal face of instrument manipulator assembly housing 448. The distal face of motor pack 446 is at position 432, which is the fully withdrawn position.

In one aspect, when motor pack 446 is located at fully withdrawn position 432, controller 290 causes insertion assembly 431 to move the preload track on which preload assembly 480 rides. The movement of the preload track results in preload assembly 480 applying a longitudinal force on motor pack 446. The longitudinal force on motor pack 446 moves motor pack 446 distally relative to instrument manipulator assembly housing 448 to position 433 so that the plurality of drive output disks including drive output disk 445 extend from the distal face of instrument manipulator assembly housing 448, as illustrated in FIG. 4B. With motor pack 446 at position 433, return spring 447 is stretched from its initial state when motor pack 446 was at position 432.

A surgical device interface element 450, e.g., a sterile adapter, could be mounted on instrument manipulator assembly 440 configured as shown in FIG. 4B. However, mounting the surgical device interface element 450 in this configuration requires compressing the plurality of preload spring assemblies including the preload spring assembly in drive output assembly 443 during the mounting process.

Thus, in one aspect, if motor pack 446 is in the position illustrated in FIG. 4B, prior to mounting surgical device interface element 450, preload release button 482 is activated so that the first longitudinal force applied on motor pack 446 by preload mechanism 408 is released. Consequently, return spring 447 pulls motor pack 446 to fully withdrawn position 432, as illustrated in FIG. 4A.

With motor pack 446 in fully withdrawn position 432, in one aspect, tongues on one end of surgical device interface element 450 are positioned in grooves in instrument manipulator assembly housing 448 and the other end of surgical device interface element 450 is moved in the proximal direction until that other end engages with release latch 435 as shown in FIG. 4C. In the configuration of FIG. 4C with motor pack 446 fully withdrawn, if the proximal end of release latch 435 is pushed, release latch 435 releases surgical device interface element 450, and surgical device interface element 450 can be removed from instrument manipulator assembly 440. However, in one aspect, if a surgical instrument is mounted in surgical device interface element 450 while motor pack 446 is in the fully withdrawn position 432, operation of release latch 435 is inhibited by release latch inhibit stop 438 until after preload release button 482 is pressed, e.g., is activated.

Thus, in this aspect, a surgical device interface element 450 (FIG. 4C) is mounted on the distal face of instrument manipulator assembly 440. As explained more completely below, surgical device interface element 450 includes a frame 451 and a movable body 451C. Moveable body 451C can move in the proximal and distal directions within frame 451. A plurality of intermediate disks is mounted in moveable body 451C so that each of the plurality of intermediate disks can rotate relative to frame 451. In this aspect, each intermediate disk in the plurality of disks is the same, and so intermediate disk 453 is representative of each of the plurality of intermediate disks.

Each intermediate disk 453 of the plurality of intermediate disks includes an intermediate driven interface 455, a first intermediate disk interface, and an intermediate drive interface 456, a second intermediate disk interface. Intermediate driven interface 455 is opposite and removed from intermediate drive interface 456. In one aspect, as explained more completely below, intermediate driven interface 455 includes a first alignment receptacle and drive dog receptacles. Intermediate drive interface 456 includes drive dogs and an engagement structure.

Each of the drive dog receptacles of the intermediate driven interface is positioned so that each of the drive dog receptacles of the intermediate driven interface is bisected by a first plane. Each of the drive dogs of the intermediate drive interface is positioned so that each of the drive dogs of the intermediate drive interface is bisected by a second plane. The first plane is perpendicular to the second plane.

Each of the drive dog receptacles of the intermediate driven interface includes a first portion comprising opposed sidewalls extending from the outer surface into the intermediate disk, a second portion comprising a bottom surface, and a third portion extending from the first portion to the second portion. The third portion includes two opposing third portion side surfaces, where each third portion side surface includes a sloped surface.

Each of the drive dogs of the intermediate drive interface includes a first portion and a second portion extending from the first portion. The first portion is a three-dimensional structure, e.g., a three-dimensional rectangle. The second portion includes two opposing second portion side surfaces, where each second portion side surface includes a curved surface. The engagement structure includes an open three-dimensional structure extending in a distal direction from the distal surface of the intermediate disk.

Movable body 451C also includes a plurality of hard stop receptacles 457. Plurality of hard stop receptacles 457 extend from a proximal face of movable body 451C in a distal direction into movable body 451C.

In one aspect, instrument manipulator assembly 440 includes a sensor that sends a signal to controller 290 when surgical device interface element 450 is mounted on instrument manipulator assembly 440. In response to this signal, controller 290 causes insertion assembly 431 to move the preload track on which preload assembly 480 rides so that preload assembly 480 is reset and so that preload assembly 480 automatically applies the longitudinal force on motor pack 446. The longitudinal force on motor pack 446 moves motor pack 446 distally relative to instrument manipulator assembly housing 448 to position 433.

As motor pack 446 is moved from fully withdrawn position 432 to position 433, a drive interface of each drive output disk 445 of the plurality of drive output disks contacts a corresponding intermediate driven interface 455 of the plurality of intermediate driven interfaces of the plurality of intermediate disks and in turn, each intermediate disk 453 contacts movable body 451C. When movable body 451C moves distally as far as possible within frame 451, further motion of drive output disk 445 in the distal direction is inhibited.

Consequently, as motor pack 446 continues to move to position 433, in response to the longitudinal force, return spring 447 is stretched further, and the preload spring assembly in each drive output assembly 443 of the plurality of drive output assemblies is compressed so that a preload force is exerted on each drive output disk 445 in the plurality of drive output disks. The preload force pushes against drive output disk 445 and against a corresponding intermediate driven interface 455 so that the preload force is transferred to each intermediate disk 453 of the plurality of intermediate disks in surgical device interface element 450. This configuration is illustrated in FIG. 4D.

When surgical device interface element 450, sometimes referred to as a surgical device interface, is first mounted on instrument manipulator assembly 440, the elements of intermediate driven interface 455 may not be aligned with corresponding elements of the drive interface on drive output disk 445. If the elements of disks 453 and 445 are not aligned, the two disks are partially coupled together by features in the drive and intermediate driven interfaces, but the two disks are not coupled, e.g., mated, to each other.

Next, controller 290 sends a signal to instrument manipulator assembly 440 to rotate drive output disk 445. As explained more completely below, rotation of intermediate disk 453 is inhibited and drive output disk 445 is rotated until the drive interface of drive output disk 445 mates with intermediate driven interface 455 of intermediate disk 453. Also, as explained more completely below, the partial coupling of the elements of the drive interface on drive output disk 445 with the corresponding elements of intermediate driven interface 455 on intermediate disk 453 assures that the two disks remain partially coupled under the preload force as the two disks rotate. In one aspect, when the two disks are coupled, another sensor detects a change in a height of the disk stack and sends a signal to controller 290 to stop the rotation of drive output disk 445. An alternative technique to sense the mating of the two disks is described below. When the two disks are mated, the preload force is reduced, because the height of the disk stack is reduced.

When motor pack 446 is at position 433, release latch inhibit stop 438 extends in front of latch pin 435P that is coupled to release latch 435. Thus, if someone tries to release surgical device interface element 450 by pressing on the proximal end of release latch 435, latch pin 435P contacts release latch inhibit stop 438, which prevents releasing surgical device interface element 450, because release latch 435 cannot be pivoted enough to release surgical device interface element 450. Thus, while there is a preload force on surgical device interface element 450, surgical device interface element 450 cannot be dismounted.

In another aspect, when surgical device interface element 450 is mounted on instrument manipulator assembly 440, a signal is not sent to the controller and so motor pack 446 remains at fully released position 432, as illustrated in FIG. 4C. A surgical instrument 460 can be coupled to instrument manipulator assembly 440 in either the configuration of FIG. 4B, or the configuration of 4C. For purposes of an example, the configuration of FIG. 4C is used.

In one aspect, a first end of surgical instrument 460 is slid along a ramp in frame 451 of surgical device interface element 450 until surgical instrument 460 is held in the proper position, as illustrated in FIG. 4E. In one aspect, surgical instrument 460 includes a body 465 and a main tube 467. Main tube 467 extends distally from body 465. Body 465 includes a driven disk receptacle 463, a shaft 466, and a driven disk 464. Shaft 466 and driven disk 464 are part of a transmission unit that transmits received torque through the instrument to one or more components of the instrument.

A proximal end of shaft 466 extends into driven disk receptacle 463, and driven disk 464 is mounted on the proximal end of shaft 466 so that driven disk 464 is positioned in driven disk receptacle 463. Driven disk 464 includes a driven interface that interfaces with intermediate drive interface 456 of intermediate disk 453.

The driven interface of driven disk 464 includes an engagement receptacle, drive dog receptacles, and a rotation disable element. The drive dog receptacles are equivalent to those described above. The rotation disable element includes a rotation locking mechanism. Upon engagement of the rotation disable element, the rotation locking mechanism engages driven disk receptacle 463 and prevents rotation of driven disk 464.

When surgical instrument 460 is coupled to instrument manipulator assembly 440, each driven disk 464 pushes a corresponding intermediate disk 453 in surgical device interface element 450 proximally so that intermediate disk 453 can rotate freely. This increases the preload force on the disk stack. However, when surgical instrument 460 is first mounted on surgical device interface element 450, the elements of intermediate drive interface 456 may not be aligned with corresponding elements of the driven interface on driven disk 464. If the elements of the two disks 453 and 464 are not aligned, the two disks are partially coupled together by features in intermediate drive interface 456 and in the driven interface, but the two disks are not mated to each other.

As explained more completely below, when intermediate drive interface 456 of an intermediate disk 453 is not aligned with the corresponding driven interface of driven disk 464, an engagement structure on intermediate drive interface 456 of intermediate disk 453 engages a rotation disable element on driven disk 464 of surgical instrument 460. The rotation disable element includes a rotation locking mechanism. Upon engagement of the rotation disable element, the rotation locking mechanism engages driven disk receptacle 463 and prevents rotation of driven disk 464.

When surgical instrument 460 is coupled to instrument manipulator assembly 440, instrument manipulator assembly 440 detects the presence of surgical instrument 460, and sends a signal to controller 290. In response to the signal, controller 290 sends a signal to instrument manipulator assembly 440 to rotate drive output disk 445. As the intermediate drive interface 456 of intermediate disk 453 rotates with driven disk 464 fixed in place, each element on intermediate drive interface 456 rotates into alignment with the corresponding element of the driven interface of driven disk 464 and mates with the corresponding element. The coupling of intermediate drive interface 456 and the driven interface on driven disk 464 releases the rotation lock on driven disk 464. Thus, the stack of disks, disks 445, 453, and 464, rotates as a unit. When disks 453 and 464 are coupled, the sensor again detects a change in a height of the disk stack and sends a signal to controller 290 to stop the rotation of drive output disk 445. When the stack of disks is mated, the preload force applied to the disk stack is referred to as a first longitudinal force, i.e., a first preload force.

The above description assumed that surgical instrument 460 was mounted with instrument manipulator assembly 440 and surgical device interface element 450 in the configuration illustrated in FIG. 4D. However, in a different aspect, if the instrument manipulator assembly 440 and surgical device interface element 450 were in the configuration illustrated in FIG. 4C, when surgical instrument 460 is mounted, the sensor sends the signal to the controller and the controller automatically resets the preload, as described above so that disks 445, 453, and 464 are under the preload force. The controller then rotates drive output disk 445 so that the stack of disks are aligned, become mated, and rotates as a unit, in a manner equivalent to that described above. Therefore, irrespective of the initial position of motor pack 446 with respect to positions 432 and 433 when surgical instrument 460 is mounted, the resulting configuration is shown in FIG. 4E.

In the configuration of FIG. 4E with the first longitudinal force applied to motor pack 446, surgical device interface element 450 cannot be removed without releasing the preload. However, surgical instrument 460 could still be removed. As explained more completely below, in one aspect, there are release buttons on each side of surgical instrument 460. Engaging the release buttons causes a mechanism in surgical instrument 460 to push movable body 451C in surgical device interface element 450 proximally so that intermediate disk 453 and driven disk 464 are disengaged and surgical instrument 460 can be removed.

As surgical instrument 460 is inserted into a cannula by moving instrument manipulator assembly 440 along insertion assembly 431, a second preload force is applied on the disk stack of disks 445, 453, and 464 by preload assembly 480 before an end component coupled to main tube 467 protrudes from a distal end of the cannula. Specifically, as surgical instrument 460 moves distally, preload assembly 480 moves distally along the preload track. As explained more completely below, when instrument manipulator assembly 440 moves distally a predetermined distance Zload, preload assembly 480 causes motor pack 446 to move predetermined distance Zload plus an additional distance Δ so that motor pack 446 is at position 434. The movement of motor pack 446 the additional distance Δ compresses the preload spring assembly in each drive output assembly 443 of the plurality of drive output assemblies so that a second preload force is exerted on each drive output disk 545 in the plurality of drive output disks. The second preload force reduces any backlash between rotation of the motor shaft in drive units 441 and rotation of shaft 467 in surgical instrument 460 to less than 0.7 degrees before the distal end of surgical instrument 260 exits the cannula.

The movement of motor pack 446 the additional distance Δ also further stretches return spring 447, and in addition inserts each of plurality of hard stops 437 into a corresponding hard stop receptacle in plurality of hard stop receptacles 457. Plurality of hard stops 437 prevents any proximal movement of moveable body 451C in surgical device interface element 450. The combination of plurality of hard stops 437 and plurality of hard stop receptacles 457 form a surgical instrument removal interlock and prevent removal of surgical instrument 460. If a person tries to engage the release buttons on surgical instrument 460, the mechanism in surgical instrument 460 cannot push movable body 451C in surgical device interface element 450 proximally, because plurality of hard stops 437 prevent any proximal movement of moveable body 451C, and so intermediate disk 453 and driven disk 464 cannot be disengaged.

The use of plurality of hard stop receptacles 457 is illustrative only and is not intended to be limiting. In another aspect, plurality of hard stop receptacles 457 is not used. Instead, plurality of hard stops 437 contact a proximal surface of moveable body 451C and prevent movement of moveable body 451C in the proximal direction.

If for some reason it is necessary to remove surgical instrument 460 while the distal tip of surgical instrument 460 extends beyond the distal end of the cannula, a person pushes preload release button 482. When pushed, preload release button 482 causes the longitudinal force on motor pack 446 to be released. Consequently, return spring 447 pulls motor pack 446 to fully withdrawn position 432.

With motor pack 446 fully withdrawn, plurality of hard stops 437 are retracted from plurality of hard stop receptacles 457 in movable body 451C of surgical device interface element 450 and disks 453 and 464 are no longer subject to any preload forces. Thus, the release buttons on surgical instrument 460 can be used to remove surgical instrument 460 from surgical device interface element 450 at any position of insertion assembly 431. In addition, release latch inhibit stop 438 is withdrawn, and release latch 435 can be used to disengage surgical device interface element 450 from instrument manipulator assembly 440 at any position of insertion assembly 431. In one aspect, the release of surgical device interface element 450 is inhibited until after preload release button 482 is pressed, e.g., release latch inhibit stop 438 inhibits the operation of release latch 435 until after preload release button 482 is pressed. The preload is automatically reset, as described above, the next time surgical device interface element 450 is installed and insertion assembly 431 is moved to the fully retracted position.

FIGS. 5 to 13 illustrate one aspect of installing the parts of surgical device assembly 300 to obtain the configuration illustrated in FIG. 3. FIG. 5 illustrates the distal end of instrument manipulator assembly 240. Instrument manipulator assembly 240 includes a drive unit assembly 541 and a drive output unit 542. In this aspect, drive output unit 542 includes a plurality of drive output assemblies 543P, e.g., eight drive output assemblies. Herein, drive output assembly 543 refers to any one of the eight drive output assemblies. In one aspect, only six of the eight drive output assemblies are used. Drive output assembly 543 includes a low backlash coupler 544, sometimes referred to as coupler 544, and a drive output disk 545. See also FIG. 16A. In one aspect, a coupler that has a backlash of less than 0.3 degrees is considered a low backlash coupler.

Drive output disk 545 is coupled to low backlash coupler 544 by a set of output pins. As explained more completely below, drive output disk 545 is a cylindrical disk that includes a distal end surface. The distal end of each drive output disk 545 has a drive interface 557. Drive interface 557 includes drive dogs and alignment elements. In FIG. 5, the drive dogs and first and second alignment elements extend in the distal direction from the distal end surface (see FIG. 16C) of drive output disk 545.

Figure 6:
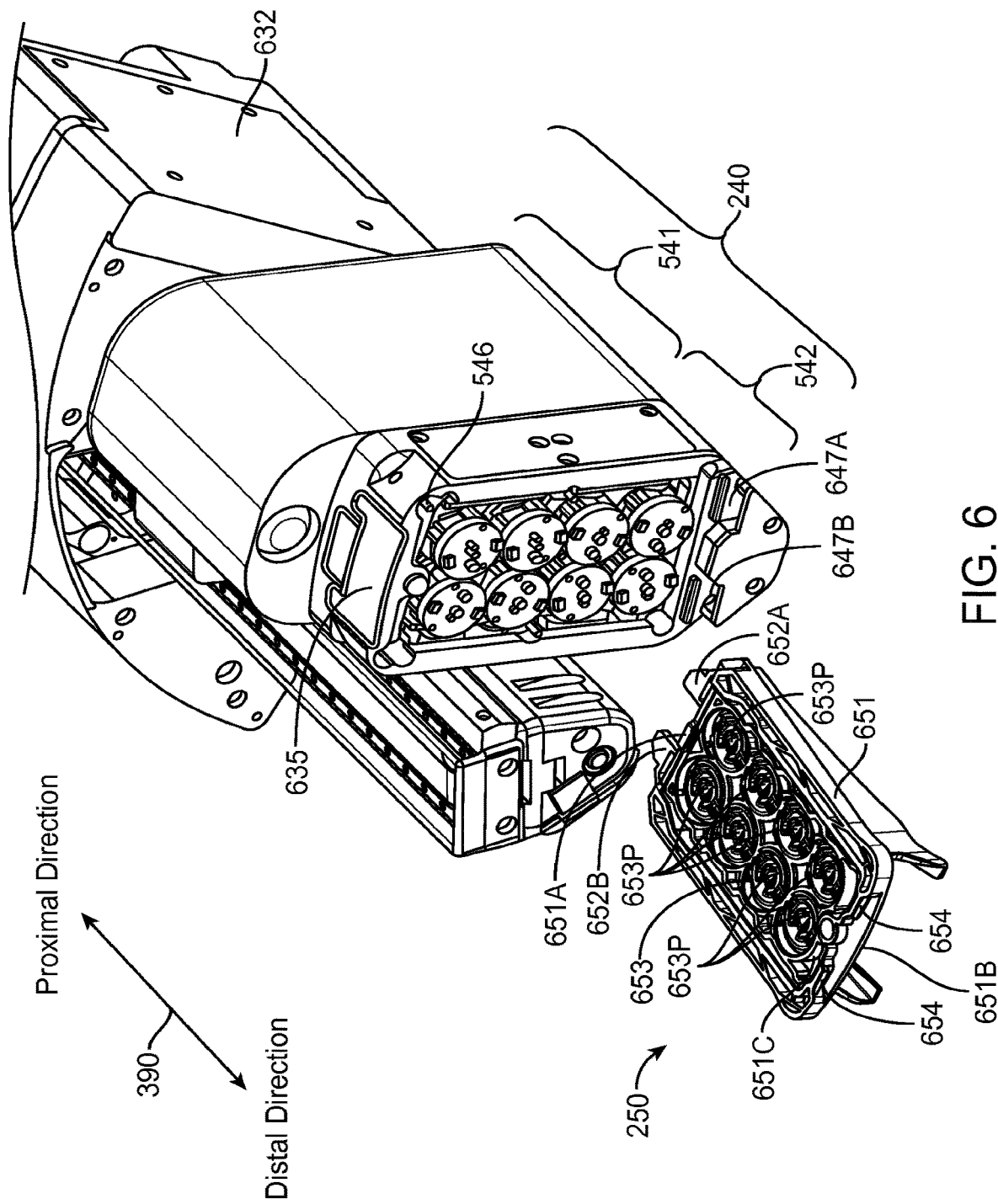
FIG. 6 illustrates the surgical instrument manipulator assembly affixed to an insertion assembly that in turn is attached to an insertion axis base assembly.

FIG. 6 shows instrument manipulator assembly 240 affixed to insertion assembly 331 that in turn is attached to an insertion axis base assembly 632. Insertion axis base assembly 632 includes a motor and power electronics to move insertion assembly 331.

Sterile adapter assembly 250 includes a sterile adapter frame 651 and a sterile drape (not shown). The sterile drape is fixedly attached to sterile adapter frame 651. Sterile adapter assembly 250 is an example of a surgical device interface element. Sterile adapter frame 651 is an example of a surgical device interface element body. In more general terms, a surgical device interface element is a structure that includes a mechanical interface between a drive interface of a drive system and a driven interface of a surgical instrument.

A plurality of tongues 652A, 652B extends from a first end 651A of sterile adapter frame 651. First end 651A is sometimes referred to as a closed end of sterile adapter assembly 250 and of sterile adapter frame 651. Each tongue 652A, 652B is configured to mate with a corresponding groove 647A, 647B in a plurality of grooves in drive output unit 542. A second end 651B of sterile adapter frame 651 includes a lip 654 that is engaged by a sterile adapter release latch 635 of drive output unit 542 when sterile adapter frame 651 is mounted on drive output unit 542. Second end 651B is sometimes referred to as an open end of sterile adapter assembly 250 and of sterile adapter frame 651.

As explained more completely below, sterile adapter frame 651 includes a movable body 651C. Moveable body 651C can move in the proximal and distal directions within sterile adapter frame 651.

A plurality of intermediate disks 653P is mounted in a plurality of intermediate disk receptacles of movable body 651C so that each intermediate disk can rotate relative to sterile adapter frame 651 and relative to movable body 651C. Thus, plurality of intermediate disks 653P is rotatably mounted in sterile adapter frame 651. Intermediate disk 653 is representative of each intermediate disk in plurality of intermediate disks 653P. Intermediate disk 653 is a representative intermediate disk.

Each intermediate disk 653 includes an intermediate driven interface 655 on a first side of intermediate disk 653 and an intermediate drive interface 756 (FIG. 7) on a second side of intermediate disk 653. The first side is opposite and removed from the second side. Intermediate driven interface 655 of each intermediate disk 653 is visible in FIG. 6 with intermediate disk 653 mounted in an intermediate disk receptacle of movable body 651C. Intermediate driven interface 655 is configured to mate with a drive interface 557 on drive output disk 545 in drive output unit 542.

To mount sterile adapter assembly 250 on instrument manipulator assembly 240, each tongue 652A, 652B is inserted into a corresponding groove 647A, 647B in drive output unit 542. See FIG. 7A. Sterile adapter frame 651 is then rotated until lip 654 is engaged by sterile adapter release latch 635. Referring to elements 652A, 652B as tongues and referring to elements 647A, 647B as grooves is illustrative only and is not intended to be limiting. Alternatively, elements 652A, 652B could be described as tenons or projections, and elements 674A, 647B could be described as mortises or cavities.

Figure 7A:
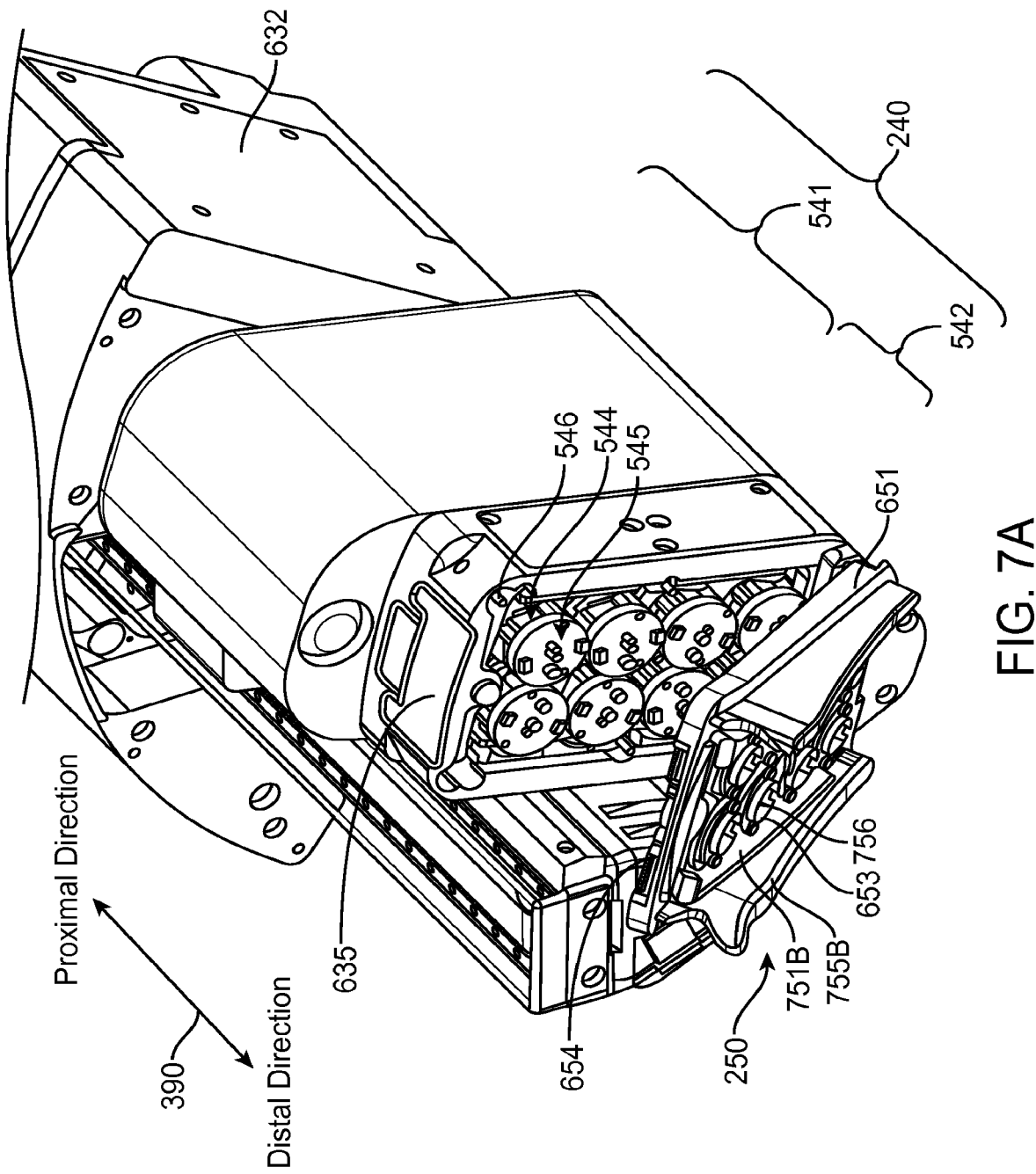
FIGS. 7A and 7B illustrate a first aspect in attaching a sterile adapter assembly to the surgical instrument manipulator assembly.
Figure 7B:
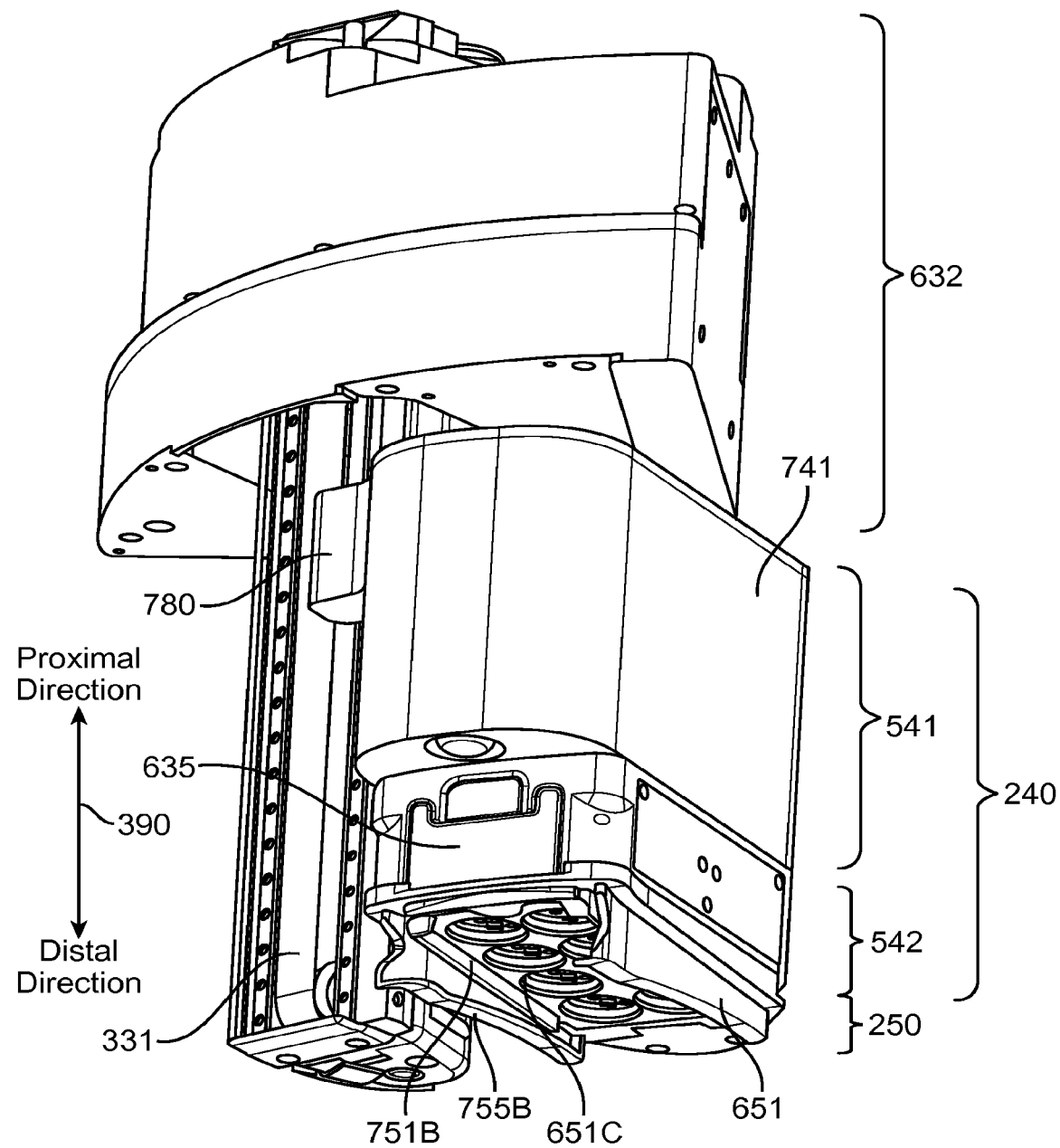

When sterile adapter frame 651 is latched to drive output unit 542, as illustrated in FIG. 7B, plunger 546 of instrument manipulator assembly 240 is depressed. When plunger 546 is depressed, a signal is generated that indicates to controller 290 the presence of sterile adapter assembly 250. In response to the signal, controller 290 in surgical system 200 first energizes an automatic preload reset mechanism (see FIG. 24B) that generates a preload force on each drive output disk 545 of plurality of drive output disks 545P (FIG. 5), and then controller sends a signal to instrument manipulator assembly 240 to rotate each drive output disk 545 of plurality of drive output disks 545P.

As explained more completely below, each drive output assembly 543 in drive output unit 542 is spring-loaded and is automatically positioned so that a preload force is exerted on each drive output disk 545 after sterile adapter assembly 250 is mounted on instrument manipulator assembly 240. The preload force pushes against drive output disk 545 and against a corresponding intermediate driven interface 655 of intermediate disk 653 in sterile adapter frame 651.

However, in FIG. 7B, when sterile adapter frame 651 is first mounted on instrument manipulator assembly 240, the elements of the intermediate driven interface 655 may not be aligned with corresponding elements of drive interface 557 on drive output disk 545. If the elements of the two disks 653 and 545 are not aligned, the two disks are partially coupled, but the two disks are not mated to each other. Thus, a disk stack including disks 545 and 653, i.e., a first disk and a second disk, which are partially coupled has a first height. After the preload force is applied to this disk stack, the controller rotates drive output disk 545.

As explained more completely below, rotation of intermediate disk 653 is inhibited while drive output disk 545 is rotated until the two disks are mated. Also, as explained more completely below, the coupling of the elements of drive interface 557 on drive output disk 545 with the corresponding elements of intermediate driven interface 655 on intermediate disk 653 assure that the two disks remain partially coupled under the preload force while drive output disk 545 is rotated. When the two disks are mated, in one aspect, the height of the disk stack has a second height, and the second height is less than the first height, a sensor in instrument manipulator assembly 240 detects this change in height and sends a signal to controller 290 to stop the rotation of drive output disk 545. An alternative way to detect the mating of the drive output disk and the intermediate disk is described below.

FIG. 7B also shows a preload assembly 780 that is coupled to a motor pack in drive unit assembly 541. Preload assembly 780 is a more detailed example of one aspect of preload assembly 480.

Preload assembly 780 rides on a preload track (see preload track 2225 in FIG. 22A) in insertion assembly 331. Instrument manipulator assembly housing 741 and instrument sterile adapter assembly 250 are fixedly attached to a distal end of insertion assembly 331 and move as a unit with the distal end of insertion assembly 331.

However, a motor pack (see FIGS. 22A to 22B) within instrument manipulator assembly housing 741 can move in the distal and proximal directions relative to instrument manipulator assembly housing 741. As explained more completely, as preload assembly 780 moves in the distal direction, preload assembly 780 provides a longitudinal force in the distal direction on the motor pack. The longitudinal force results in compression of springs in drive output assembly 543 that generates a second preload force. The second preload force reduces any backlash to less than 0.7 degrees before the distal end of surgical instrument 260 exits the cannula.

Figure 11:
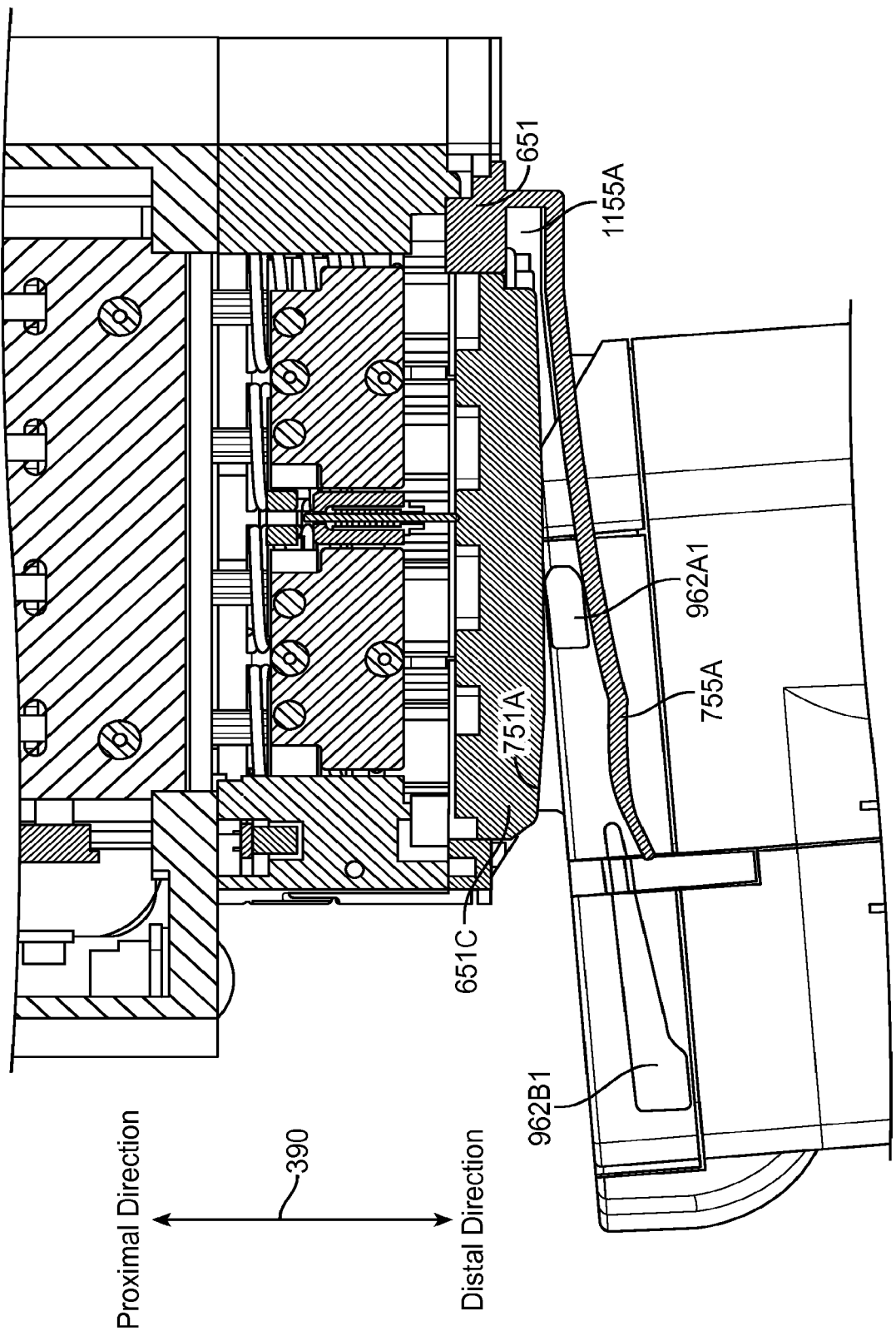

Returning to FIG. 7A, an intermediate drive interface 756 on the distal side of intermediate disk 653 of plurality of intermediate disks 653P is visible. Also visible in FIGS. 7A and 7B is an instrument insertion skid plate 755B, which extends from an inner side surface of sterile adapter frame 651. There is a similar instrument insertion skid plate 755A that extends from an inner side surface on the opposite side of sterile adapter frame 651. In FIGS. 7A and 7B, a side 751B, sometimes called lip 751B of movable body 651C is also visible. Side 751A is shown in FIG. 11.

FIGS. 8A to 8I illustrate an alternative example, sterile adapter assembly 250A, of surgical device interface element 450 and of sterile adapter assembly 250. Sterile adapter assembly 250A includes a sterile adapter frame 851 and a sterile drape (not shown). The sterile drape is fixedly attached to sterile adapter frame 851. Sterile adapter frame 851 is an example of a surgical device interface element body.

A plurality of grooves 852A, 852B (FIGS. 8H and 8I) extend into a first end 851A of sterile adapter frame 851 to form first and second lips 852A1, 852B1. First end 851A is sometimes referred to as a closed end of sterile adapter assembly 250A and of sterile adapter frame 851. The depth and size of each groove 852A, 852B is configured to allow a surface of a corresponding hook 847A, 847B on a distal end of ventral latch assembly 847 to engage a corresponding lip 852A1, 852B1.

Each of first and second lips 852A1, 852B1 includes a first surface and a second surface. The second surface is opposite the first surface, e.g., the first surface is a proximal surface and the second surface is a distal surface. The second surface of the lip is longer than the first surface of the lip in a direction perpendicular to axis 890. A third surface of the lip extends between the first and second surfaces, and is tapered in view of the different lengths of the first and second surfaces. In one aspect, the third surface is a beveled surface.

A second end 851B of sterile adapter frame 851 includes a lip 854 that is engaged by a lip 835L that extends inward towards axis 890 from a distal portion of a sterile adapter release latch 835 of drive output unit 542A when sterile adapter assembly 250A is mounted on drive output unit 542A. Second end 851B is sometimes referred to as an open end of sterile adapter assembly 250A and of sterile adapter frame 851.

Lip 854 includes a first surface and a second surface. The second surface is opposite the first surface, e.g., the first surface is a proximal surface and the second surface is a distal surface. The second surface of lip 854 is longer than the first surface of lip 854 in a direction perpendicular to axis 890. A third surface of lip 854 extends between the first and second surfaces, and is tapered in view of the different lengths of the first and second surfaces. In one aspect, the third surface is a beveled surface.

As explained more completely below, sterile adapter frame 851 includes a movable body 851C. Moveable body 851C can move in the proximal and distal directions within sterile adapter frame 851. An instrument insertion skid plate 855A extends from an inner side surface of sterile adapter frame 851. There is a similar instrument insertion skid plate 855B that extends from an inner side surface on the opposite side of sterile adapter frame 851. In FIG. 8A, a side 851C1, sometimes called a lip 851C1 of movable body 851C is also visible.

The features and operation of movable body 851C are the same as the features and operation of movable body 651C, and so the description of the features and operation of moveable body 651C are not repeated here for movable body 851C. Also, the mounting of a surgical instrument on sterile adapter assembly 250A is the same as described with respect to sterile adapter assembly 250, and so that description is not repeated for sterile adapter assembly 250A.

To mount sterile adapter assembly 250A on instrument manipulator assembly 240, sterile adapter assembly 250A is moved axially in the proximal direction along longitudinal axis 890, i.e., the direction indicated by arrow 891 (FIGS. 8A and 8B) until sterile adapter assembly is engaged by features of drive output unit 542A, as described more completely below. FIGS. 8B to 8D are cut-away drawings that illustrate the elements using in mounting sterile adapter assembly 250A to drive output unit 542A. Drive output unit 542A is similar to drive output unit 542 with the exception of latching mechanism 860 for sterile adapter assembly 250A that is included in drive output unit 542A.

A frame 842F of drive output unit 542A includes a first sterile adapter alignment element 845A, sometimes referred to as a first alignment element, extending from the distal face of frame 842F and a second sterile adapter alignment element 845B, sometimes referred to as a second alignment element also extending from the distal face of frame 842F.

Sterile adapter alignment element 845A is adjacent but inboard of ventral latch assembly 847, while sterile adapter alignment element 845B is adjacent but inboard of sterile adapter release latch 835.

As sterile adapter assembly 250A moves axially to the proximity of the distal face of drive output unit 542A, first sterile adapter alignment element 845A enters, e.g., engages, first sterile adapter alignment receptacle 853A (FIGS. 8H and 8I) in sterile adapter frame 851. Similarly, second sterile adapter alignment element 845B enters, e.g., engages, second sterile adapter alignment receptacle 853B in sterile adapter frame 851. The alignment elements and receptacles are configured to align sterile adapter assembly 250A so that further motion of sterile adapter assembly 250A in the proximal direction causes latching mechanism 860 to engage sterile adapter assembly 250A.

First and second alignment elements 845A, 845B are an example of a plurality of sterile adapter alignment elements. First and second alignment receptacles 853A, 853B are an example of a plurality of alignments receptacles. Thus, drive output unit 542A, and so instrument manipulator assembly 240, in this aspect, includes a plurality of sterile adapter alignment elements, and sterile adapter assembly 250A includes a plurality of alignment receptacles. Alternatively, the plurality of receptacles could be formed in drive output unit 542A, and the plurality of alignment elements could extend from the proximal face of sterile adapter frame 851.

As sterile adapter assembly 250A moves further in the proximal direction, a tapered surface of hook 847A contacts the tapered surface of lip 852A1 of sterile adapter assembly 250A, and a tapered surface of a tapered surface of hook 847B contacts the tapered surface of lip 852B1 of sterile adapter assembly 250A. Similarly, a tapered surface of lip 835L of sterile adapter release latch 835 contacts the tapered surface of lip 854 of sterile adapter assembly 250A.

Further motion of the sterile adapter assembly 250A in the proximal direction causes a distal end portion of sterile adapter release latch 835 to pivot outward away from axis 890 of drive output unit 542A, and hooks 847A, 847B of ventral latch assembly 847 to pivot outward, away from axis 890 of drive output unit 542A. After hooks 847A and 847B and lip 835L move distally beyond lips 852A1 and 852B1, and after lip 835L moves distally beyond lip 854, hooks 847A and 847B and lip 835L pivot inward towards axis 890 so that lip 835L engages lip 854, hook 847A engages lip 852A1, and hook 847B engages lip 852B1. Specifically, a proximal surface of each hook contacts the second surface of the corresponding lip. Hence, sterile adapter assembly 250A is mounted on drive output unit 542A, as illustrated in FIG. 8D, by only moving sterile adapter assembly 250 along axis 890 toward the distal face of drive output unit 542A.

Figure 8E:
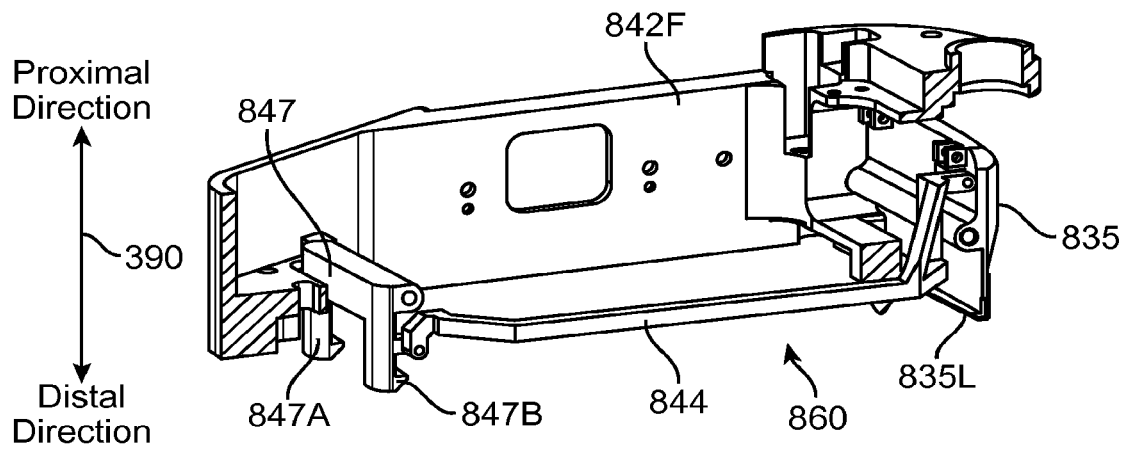
FIGS. 8E to 8G are cut-away drawings illustrating a sterile adapter latch assembly for the sterile adapter assembly of FIG. 8A.
Figure 8F:
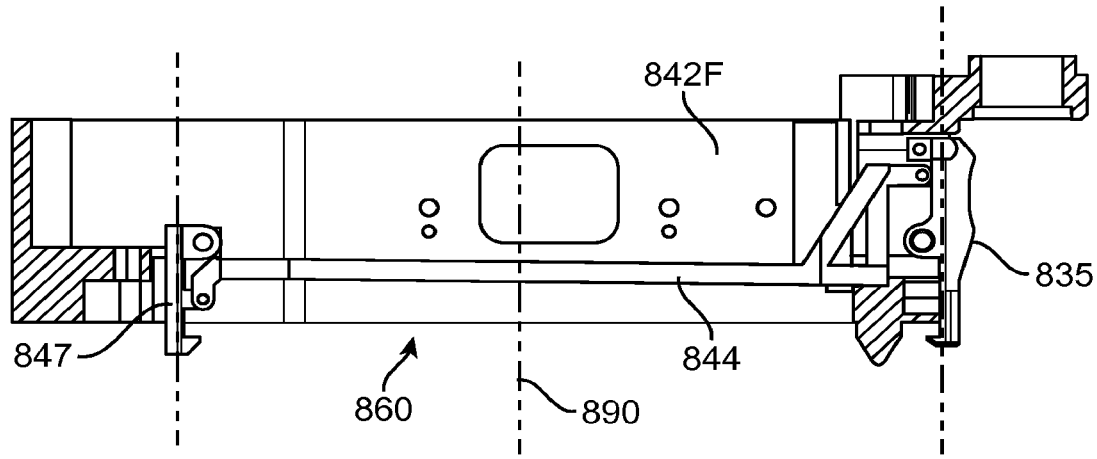
Figure 8G:
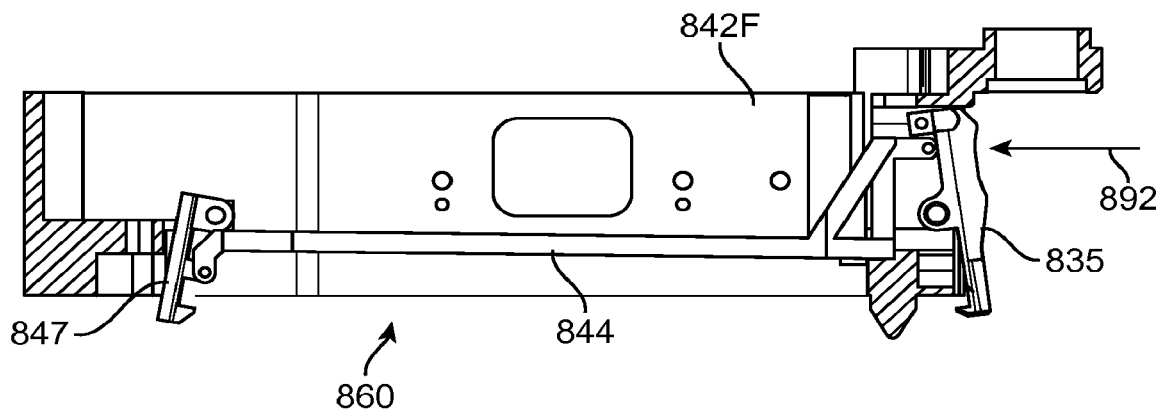

FIGS. 8E to 8G are cut-away drawings illustrating sterile adapter latching mechanism 860. Components that are not needed to understand sterile adapter latching mechanism 860 are not included in FIGS. 8E to 8G. Sterile adapter latching mechanism 860 is movably coupled to frame 842F of drive output unit 542A. Sterile adapter latching mechanism 860 includes sterile adapter release latch 835, push rod 844, and ventral latch assembly 847. Push rod 844 couples sterile adapter release latch 835 to ventral latch assembly 847 so that motion of latch 835 is transferred to ventral latch assembly 847. Thus, the sterile adapter latching mechanism includes a first latch assembly, a second latch assembly, and a push rod coupling the first latch assembly to the second latch assembly.

Sterile adapter release latch 835, sometimes referred to as latch 835, includes a proximal end portion—an example of a first end portion—and a distal end portion—an example of a second end portion opposite from the first end portion. A latch pin 835P (FIG. 8B) is coupled to an interior surface of the proximal end portion of latch 835. Latch pin 835P extends inward from the interior surface of latch 835. Latch pin 835P is equivalent to latch pin 435P and latch pin 2635P, and so the description of those latch pins is directly applicable to latch pin 835P, and conversely. Lip 835L extends inward from the distal portion of latch 835. In this aspect, sterile adapter release latch 835 is pivotally connected to frame 842F. The pivotal connection is spring loaded to maintain latch 835 in what is referred to as the engaged position, or engaged state in the absence of a force that causes latch 835 to pivot. A first end of push rod 844 is pivotally connected to the proximal end portion of latch 835 so that when the proximal portion of latch 835 is pushed inward, e.g., pushed in a first direction, the motion is transferred to push rod 844.

In this aspect, a proximal end portion, e.g., a first end portion, of ventral latch assembly 847 is pivotally connected to frame 842F. In one aspect, the connection to frame 842F is spring-loaded to maintain ventral latch assembly 847 in what is referred to as the engaged position, or engaged state in the absence of a force that causes ventral latch assembly 847 to pivot. Two legs extend distally from the proximal end portion of ventral latch assembly 847. At the distal end of each leg, e.g., at the distal end of ventral latch assembly 847, is a hook, i.e., one of hook 847A and hook 847B. Push rod 844 is pivotally connected to one leg of ventral latch assembly 847 between the proximal end portion of latch assembly 847 and the distal end of the leg.

In this aspect, ventral latch assembly 847 is implemented as a Class 3 lever, the effort is between the fulcrum (pivotal connection to frame) and the load (hooks 847A and 847B). Use of a Class 3 lever is illustrative only and is not intended to be limiting. In other aspects, a Class 1 lever or a Class 2 lever could be used. For a Class 2 lever, the load is between the fulcrum and the effort, and for a Class 1 lever, the fulcrum is between the effort and the load.

As shown in FIG. 8F, in a first state where no external forces are acting on sterile adapter release latch 835, both sterile adapter release latch 835 and ventral latch assembly 847 are in a steady-state position, the engaged position, with a longitudinal axis of each aligned with longitudinal axis 890, i.e., substantially parallel to axis 890. Here, substantially parallel means parallel within manufacturing tolerances. In a second state, where an external force 892 is applied to the proximal end of latch 835 (FIG. 8G), or alternatively, a force is applied to lip 835L, the proximal end portion of latch 835 pivots inward toward axis 890 and the distal end portion of latch 835 pivots outward. In response to the motion of latch 835, the distal end portions of ventral latch assembly 847 pivot outward. Thus, external force 892 causes the two latch assemblies to move to the disengaged position, e.g., move to a second state different from the first state.

Figure 8H:
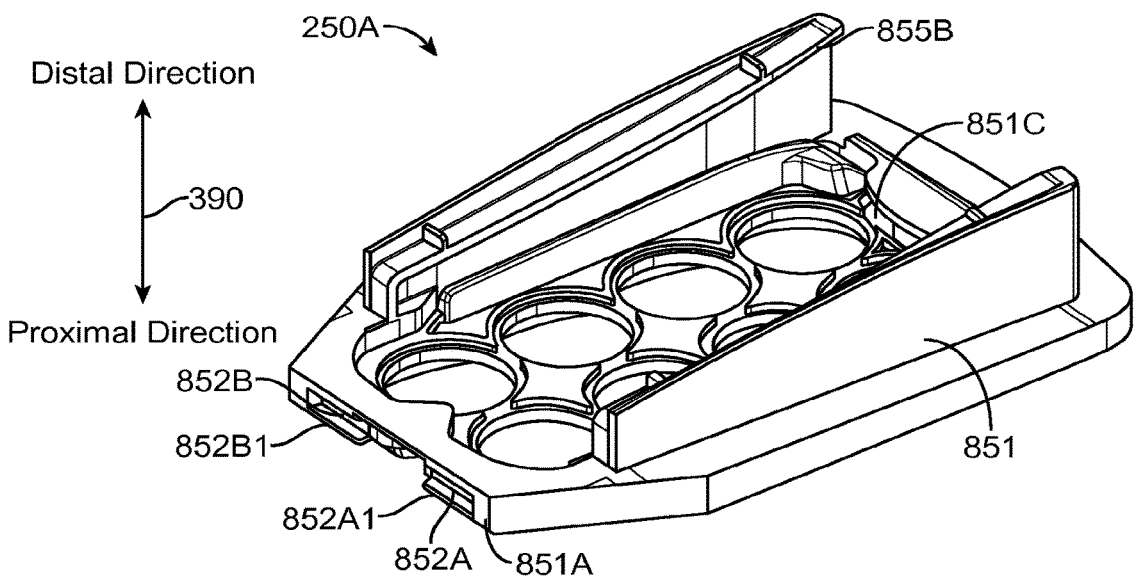
FIG. 8H is bottom perspective view of the sterile adapter assembly of FIG. 8A.
Figure 8I:
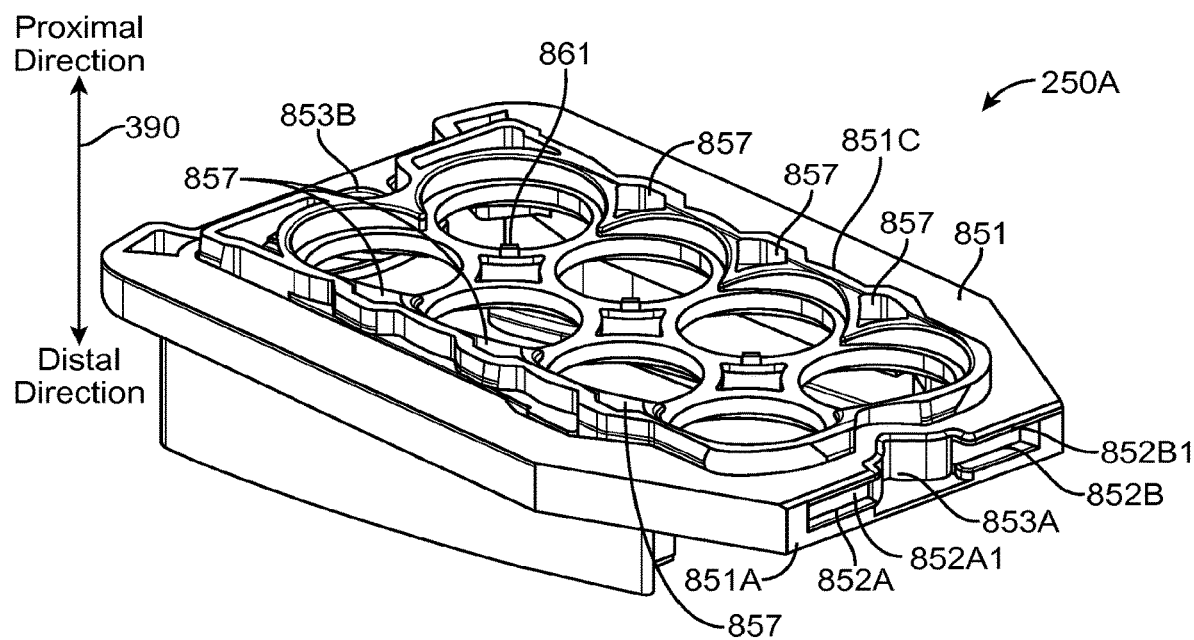
FIG. 8I is a top perspective view of the sterile adapter assembly of FIG. 8A.

FIG. 8H is bottom perspective view of sterile adapter assembly 250A. FIG. 8I is a top perspective view of sterile adapter assembly 250A. While it is not shown in FIGS. 8H and 8I, an intermediate disk 653 is mounted in each of the plurality of intermediate disk receptacles in movable body 851C. As for sterile adapter assembly 250 (FIG. 6), a plurality of intermediate disks is mounted in the plurality of intermediate disks receptacles of movable body 851C so that each intermediate disk can rotate relative to sterile adapter frame 851 and to movable body 851C. Thus, a plurality of intermediate disks is rotatably mounted in sterile adapter frame 851. The plurality of intermediate disks is the same as plurality of intermediate disks 653P, and so the characteristics of the plurality of intermediate disks are not repeated here. Also, each intermediate disk in the plurality of disks mounted in movable body 851C is the same as intermediate disk 653 (see FIG. 17B), and so the description of intermediate disk 653 is not repeated with respect to sterile adapter assembly 250A.

The plurality of hard stop receptacles 857 of sterile adapter assembly 250A is the same as and works in the same way as described for plurality of hard stop receptacles 1757, and so that description is not repeated here. Sterile adapter assembly 250A has an intermediate disk hard stop 861 associated with each intermediate disk. Each intermediate disk hard stop 861 of sterile adapter assembly 250A is the same as and works in the same way as described for intermediate disk hard stop 1761 (FIG. 17B), and so that description is not repeated here FIG. 9A is a more detailed illustration of surgical instrument 260 in one aspect. Surgical instrument 260, in this aspect, includes a driven interface assembly 961, a transmission unit 965, a main tube 967, a parallel motion mechanism 968, a wrist joint 969, and an end effector 970. Wrist joint 969 is described, for example, in U.S. Patent Application No. US 2003/0036748 A1 (filed Jun. 28, 2002 disclosing "Surgical Tool Having Positively Positionable Tendon-Activated Multi-Disk Wrist Joint"), which is incorporated herein by reference. Parallel motion mechanism 968 is described, for example, in U.S. Pat. No. 7,942,868 B2 (filed Jun. 13, 2007, disclosing "Surgical Instrument With Parallel Motion Mechanism").

As shown in FIG. 9B, driven interface assembly 961 includes a plurality of driven disks 964P. Plurality of driven disks 964P is an example of driven interface elements. Driven disk 964 is representative of each driven disk of plurality of driven disks 964P. Driven disk 964 is mounted on a shaft of transmission unit 965. Also, each driven disk 964 is mounted in a receptacle in a body of driven interface assembly 961 (see FIG. 19B).

Mechanical components (e.g., gears, levers, gimbals, cables etc.) in transmission unit 965 transfer torques from plurality of driven disks 964P to cables, wires, and/or cable, wire, and hypotube combinations that run through main tube 967 to control movement of parallel motion mechanism 968, wrist joint 969, and end effector 970. Main tube 967, although substantially rigid, can be bent slightly between transmission unit 965 and entry guide 270. This bending allows the instrument body tube bores in entry guide 270 to be spaced closer together than the size of the transmission units would otherwise allow. The bending is resilient so that main tube 967 assumes its straight shape when surgical instrument 260 is withdrawn from entry guide 270 (the main tube may be formed with a permanent bend, which would prevent instrument body roll).

Figure 10:
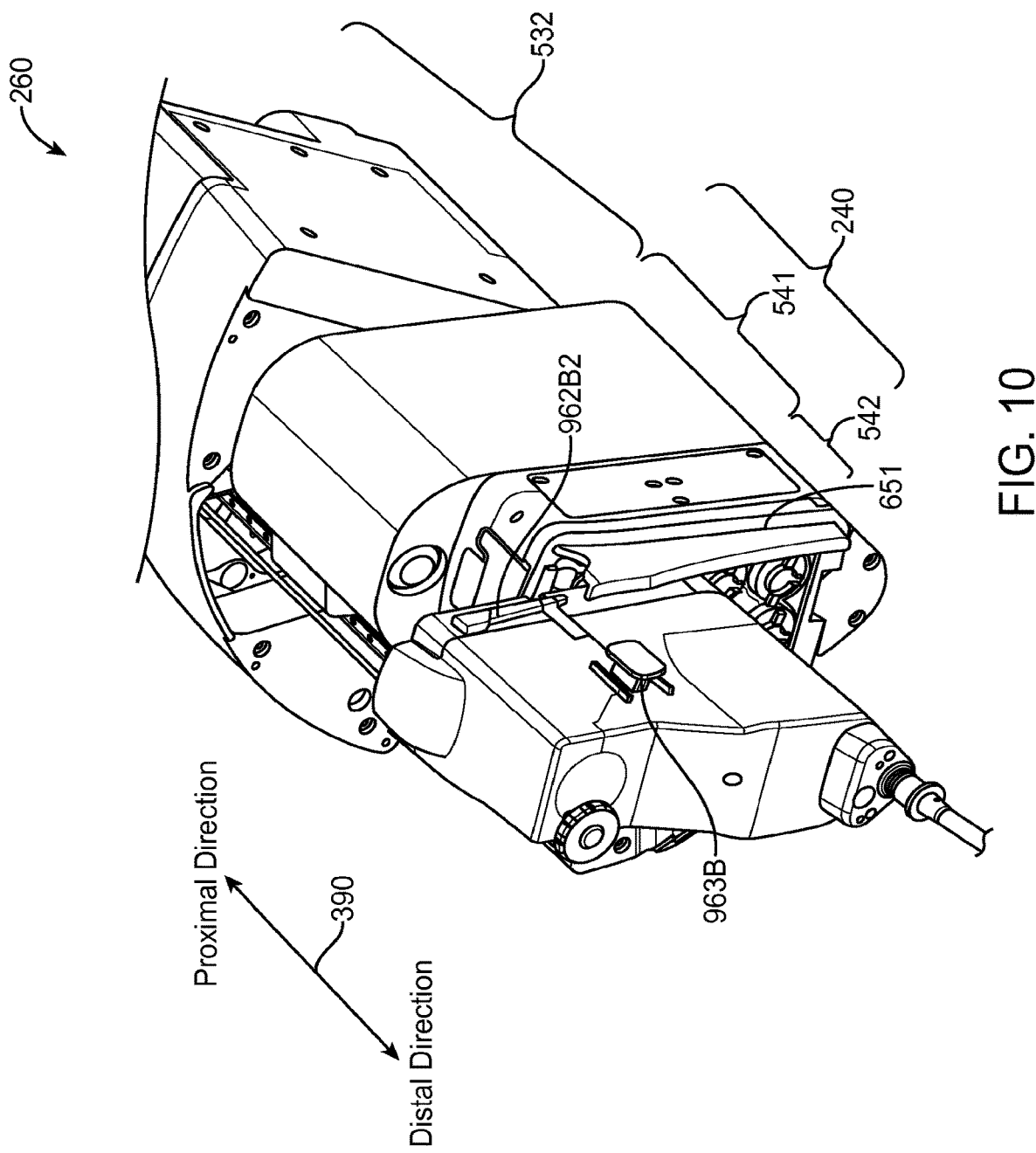
FIGS. 10 to 13 illustrate stages in the mounting of the surgical instrument in the sterile adapter assembly.

Driven interface assembly 961 has on each side a pair of mounting wings (962A1, 962B1) and (962A2, 962B2). Also, on each side of transmission unit 965 is a release button 963A, 963B. Mounting wing 962B2 and release button 963B are shown in FIG. 10.

To mount surgical instrument 260 in sterile adapter frame 651, first, mounting wings 962A1, 962A2 are placed on skid plates 755A, 755B (FIGS. 10 and 11) at the open end of sterile adapter frame 651. FIG. 11 is a cutaway view of FIG. 10 with the outer side surface of sterile adapter frame 651 removed.

Figure 12:
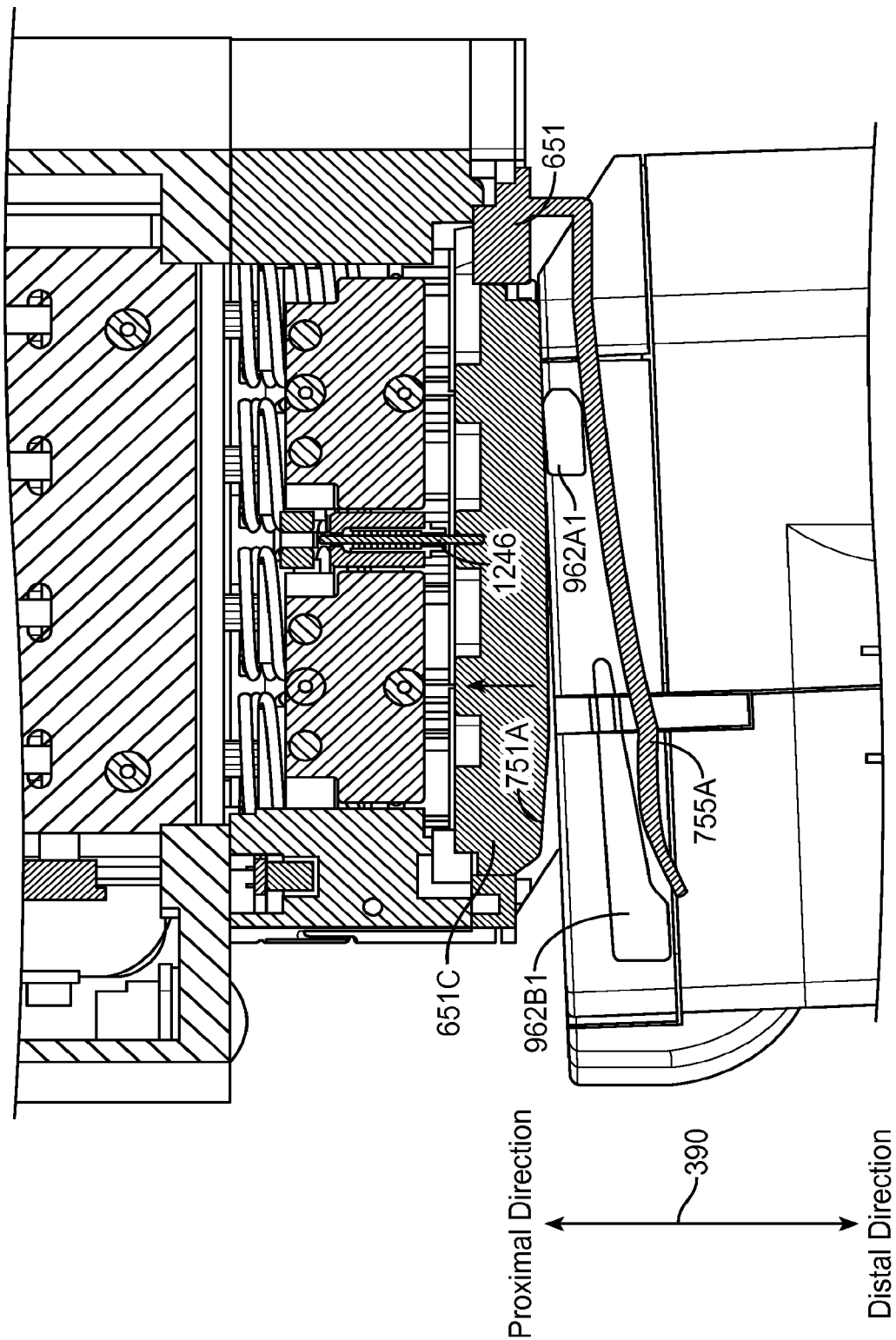
Figure 13:
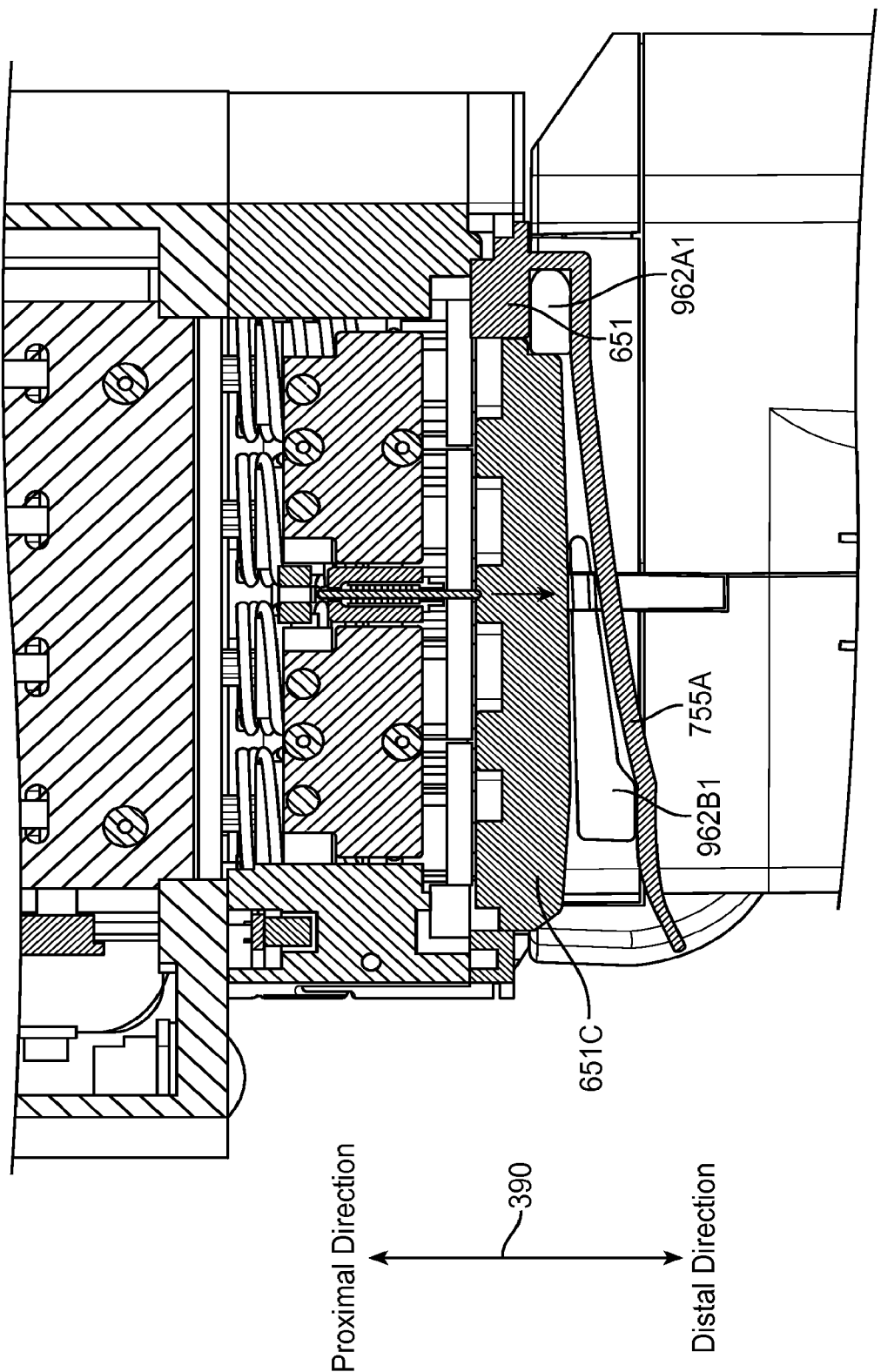

Mounting wing 962A1 is resting on skid plate 755A that extends from a first sidewall of sterile adapter frame 651. As surgical instrument 260 is slid on skid plate 755A towards parking slot 1155A, which is at the opposite end of skid plate 755A, (FIG. 11), the top surface of first mounting wings 962A1, 962A2 contacts the bottom edge of lip 751A, 751B, which moves movable body 651C in the proximal direction (FIG. 12). The proximal motion of movable body 651C depresses plunger 1246 of instrument manipulator assembly 240 in the proximal direction, which in turn generates a signal to controller 290 that surgical instrument 260 is being loaded unto sterile adapter assembly 250.

When mounting wing 962A1 reaches parking slot 1155A at the closed end of sterile adapter frame 651 (FIG. 13), the top surface of first mounting wings 962A1, 962A2 no longer contacts the bottom edge of lip 751A, 751B. Consequently, the preload force on movable body 651C moves body 651C in the distal direction (FIG. 13) and locks first mounting wing 962A1 in place. When first mounting wing 962A1 reaches the closed end of sterile adapter frame 651, second mounting wing 962B1 rests on a flat portion of skid plate 755A near the open end of sterile adapter frame 651.

Each intermediate disk 653 in sterile adapter frame 651 is being pushed axially in the distal direction by the preload force on the plurality of drive output disks 545P. Thus, as surgical instrument 260 is mounted in sterile adapter frame 651, plurality of intermediate disks 653P transfer the first preload force to movable body 651C so that the preload force is applied to mounting wing 962A1. This preload force is selected so that surgical instrument 260 can be easily slid into sterile adapter frame 651 and so that a small preload force is maintained on all the disks.

When surgical instrument 260 is mounted in sterile adapter assembly 250, instrument manipulator assembly 240 detects the presence of surgical instrument 260 and sends a signal to controller 290 that indicates the presence of surgical instrument 260. In response to the signal, controller 290 in surgical system 200 sends the signal to instrument manipulator assembly 240 to rotate each drive output disk 545 of plurality of drive output disks 545P.

As explained more completely below, each drive output assembly 543 in drive output unit 542 is spring-loaded and is automatically positioned so that a preload force is exerted on each drive output disk 545 after sterile adapter assembly 250 is mounted on instrument manipulator assembly 240. The preload force pushes against drive output disk 545 and against a corresponding intermediate driven interface 655 of intermediate disk 653 in sterile adapter frame 651.

However, in FIG. 7B, when surgical instrument 260 is first mounted on sterile adapter assembly 250, the elements of the intermediate drive interface 765 of intermediate disk 653 may not be aligned with corresponding elements of driven interface 980 on driven disk 964. If the elements of the two disks 653 and 964 are not aligned, the two disks are partially coupled, but the two disks are not mated to each other. Thus, a disk stack including disks 964, 653, and 545, i.e., a third disk, the second disk, and the first disk, which are partially coupled has a third height.

When surgical instrument 260 is mounted in sterile adapter frame 651, each driven disk 964 in driven interface assembly 961 pushes a corresponding intermediate disk 653 in sterile adapter assembly 250 proximally so that intermediate disk 653 can rotate freely. As explained more completely below, when intermediate drive interface 756 of an intermediate disk 653 in sterile adapter assembly 250 is not aligned with corresponding driven interface 980 of a driven disk 964 in driven interface assembly 961, an engagement structure on intermediate drive interface 756 of intermediate disk 653 engages a rotation disable element 1980 (see FIG.

19A) on driven disk 964 of surgical instrument 260, which prevents rotation of driven disk 964 in driven interface assembly 961.

As intermediate drive interface 756 of intermediate disk 653 rotates with driven disk 964 fixed in place, each element on intermediate drive interface 756 rotates into alignment with the corresponding element of driven interface 980 of driven disk 964 and mates with the corresponding element. The coupling of intermediate drive interface 756 and driven interface 980 releases the rotation lock on driven disk 964. Thus, the stack of disks rotates as a unit. When all three disks are mated, the height of the disk stack has a fourth height, and the fourth height is less than the third height, a sensor in instrument manipulator assembly 240 detects this change in height and sends a signal to controller to stop the rotation of drive output disk 545. The sensor in instrument manipulator assembly 240 that detects changes in the height of the disk stack can be a mechanical sensor, an optical sensor, an inductive sensor, a capacitive sensor, etc.

Figure 14:
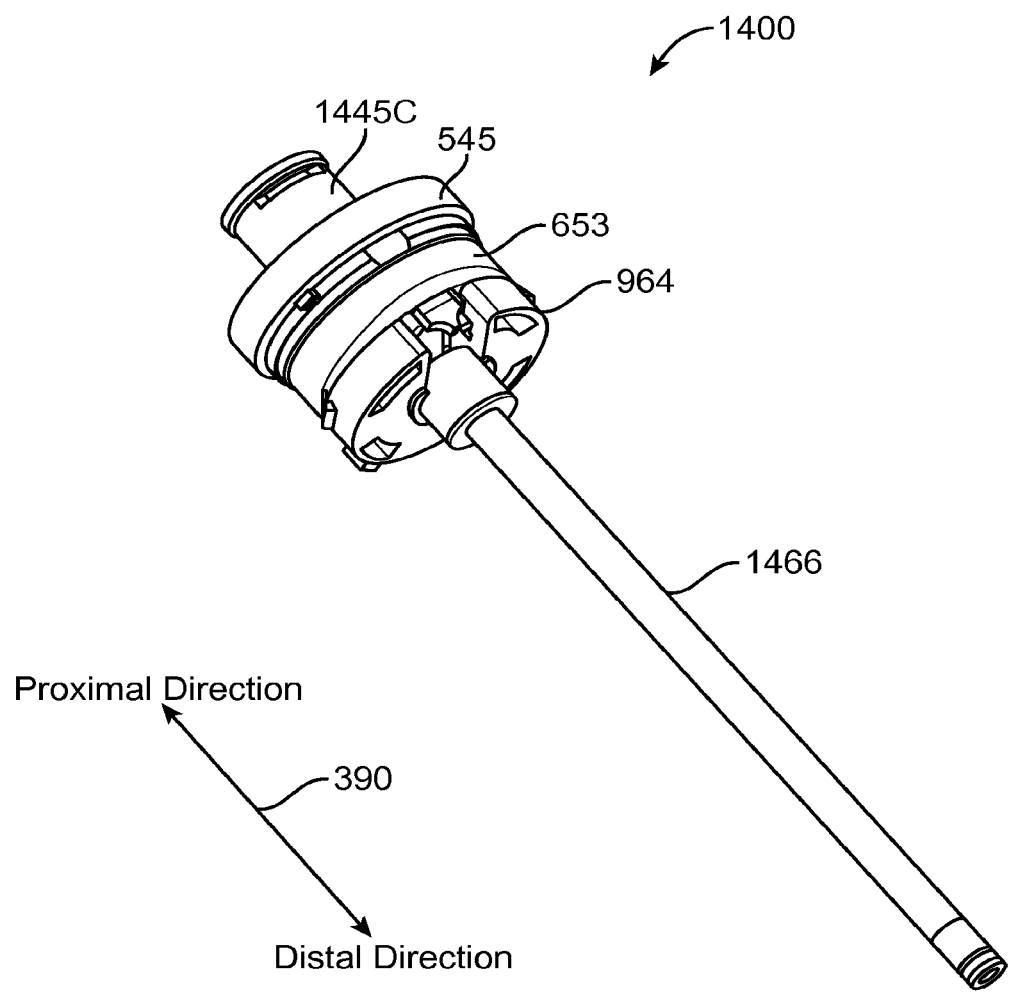
FIG. 14 is an illustration of a disk stack when a drive output disk is coupled, e.g., mated, to an intermediate disk and the intermediate disk is coupled to a driven disk.

FIG. 14 is an illustration of disk stack 1400 when drive output disk 545 is coupled to intermediate disk 653, and intermediate disk 653 is coupled to driven disk 964. Herein, coupled means that all of the alignment features on two interfacing disks are aligned so that the two disks are mated, i.e., fully coupled. As described above, when some of the alignment features on two interfacing disks are aligned, but other alignment features on the two interfacing disks are not aligned, the two interfacing disks are partially coupled. The preload force is selected so that despite some backlash, the two partially coupled disks remain in contact so that all the alignment features can be aligned and mated.

Disk stack 1400 is the disk stack configuration referred to above with respect to FIGS. 3A and 3B. Drive interface 557 of drive output disk 545 is mated to intermediate driven interface 655 of intermediate disk 653 and intermediate drive interface 756 of intermediate disk 653 is mated to driven interface 980 of driven disk 964. As explained more completely below, when there is a high preload force, i.e., a second preload force, on the stack of disks 1400, there is zero backlash between the disks in disk stack 1400 for torque levels used in surgical procedures even though shaft 1466 may not be precisely aligned with the shaft coupled to drive output disk 545. When disks 545, 653, and 964 in stack of disks 1400 are mated under the second preload force, there is zero backlash in the couplings between the disks for torque levels used in surgical procedures. Low backlash coupler 544 compensates for spatial misalignment and transmits motion and torque to disk stack 1400. As explained more completely below, the design of drive dogs compensates for angular misalignment of the drive output disk 445 and the driven disk 964.

Figure 15A:
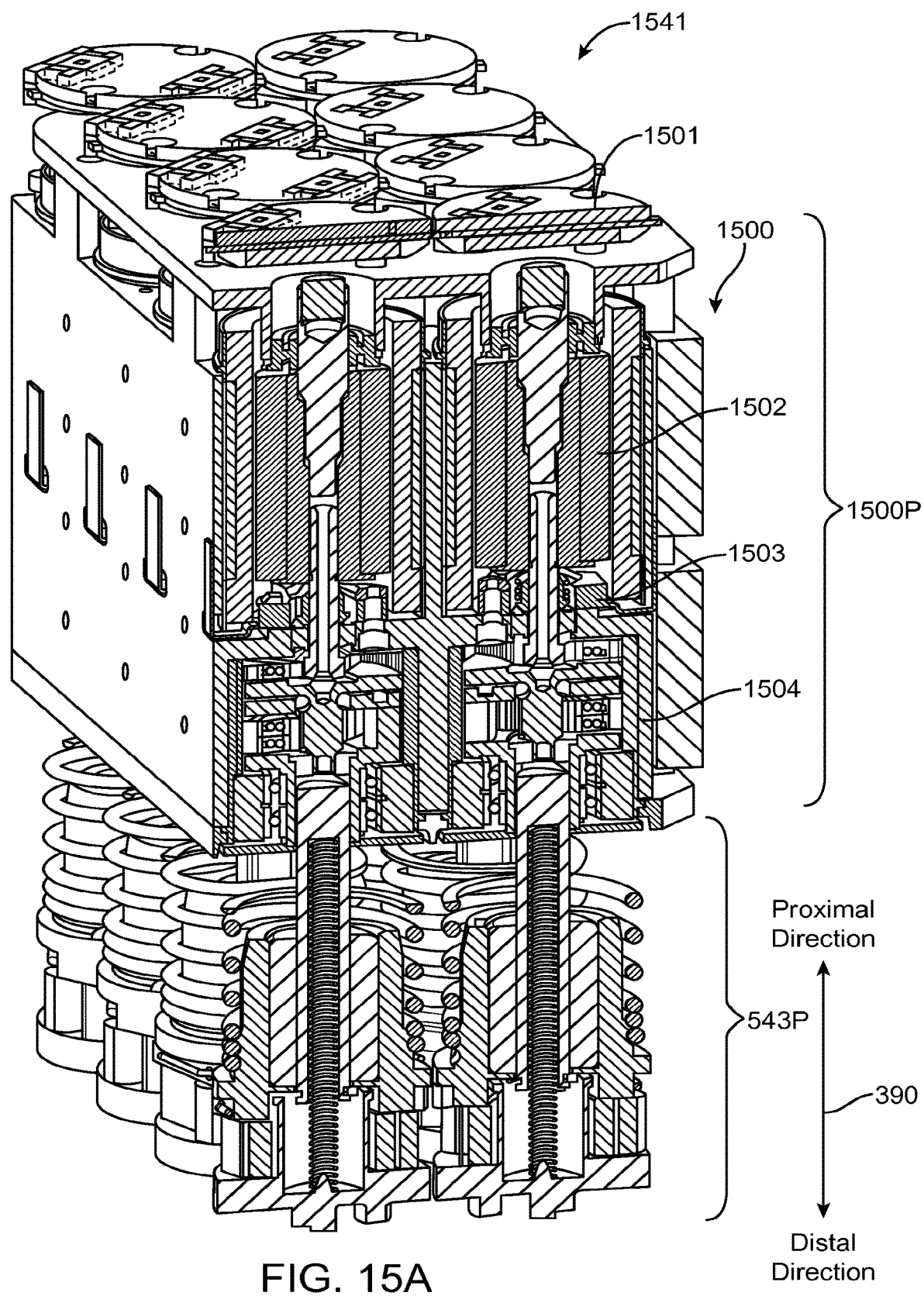
FIG. 15A is an illustration of the surgical instrument manipulator assembly with the drive unit assembly housing removed and with the housing around the drive output unit removed.

FIG. 15A is an illustration of instrument manipulator assembly 240 with instrument manipulator assembly housing 741 removed. Also, there is a vertical cut showing the components in drive unit assembly 541. Instrument manipulator assembly 240 includes a motor pack 1541 that in turn includes a plurality of drive units 1500P and plurality of drive output assemblies 543P. Each drive unit 1500 of plurality of drive units 1500P includes an encoder 1501, a slotless brushless servomotor 1502, a compact Hall effects sensor 1503, and a planetary gearhead 1504.

In one aspect, slotless brushless servomotor 1502 has a very high motor constant, and so servomotor 1502 is very efficient. The use of a slotless brushless servomotor is illustrative only and is not intended to limit the motors in plurality of drive units 1500P to this specific type of motor. A variety of motors can be used including brush type motors, stepper motors, etc. Each servomotor 1502 includes magnetic shielding to prevent torque ripple to adjacent servomotors in view of the compact configuration of the eight servomotors in motor pack 1541.

Compact Hall effects sensor 1503 is used to detect the position of the permanent magnet in servomotor 1502. Hall effects sensor 1503 is used as a second encoder. An encoder-to-hall check compares the rotary positions reported by encoder 1501 and Hall effects sensor 1503. If the rotary positions are significantly different, something is wrong with encoder 1501, Hall effects sensor 1503, or the mechanism between them. Executing software in a controller immediately turns off the motors, when this check fails.

Planetary gearhead 1504 is heavy duty and highly efficient (greater than 90%), and thus is easier to back-drive than typical gearheads. By back drivable, it is meant that the output shaft of the gearhead can be rotated with a relatively low torque, as compared to typical gearheads.

Planetary gearhead 1504 has backlash, in one aspect, of less than one degree, and in another aspect has low backlash, e.g., 0.4 degrees. In one aspect, four of the planetary gearheads have a 28:1 input to output ratio and are referred to as standard planetary gearheads. In this aspect, four of the planetary gearheads have a 9 to 1 input to output ratio and are referred to as high-speed gearheads. Similarly a drive unit 1500 with a standard planetary gearhead is referred to as a standard drive unit. A drive unit 1500 with a high-speed planetary gearhead is referred to as a high-speed drive.

FIGS. 15B to 15E are illustrations of one example of planetary gearheads suitable for use in motor pack 1541. FIG. 15B is a side view of planetary gearhead 1504. FIG. 15C is a distal view of planetary gearhead 1504. FIG. 15D is a proximal view of a 28:1 planetary gearhead. FIG. 15E is a proximal view of a 9:1 planetary gearhead. One example of dimensions for the gearhead in FIGS. 15B to 15E is given in Table 1.

TABLE 1

| REFERENCE NUMBER | DIMENSION |
|---|---|
| L1 | 1.043 inches |
| L2 | 1.070 inches |
| L3 | 0.673 inches |
| L4 | 0.698 ± 0.002 inches |
| L5 | 0.738 inches |
| L6 | 0.030 inches |
| D1 | 0.684 inches (diameter) |
| A1 | 5.00 degrees |
| D2 | 0.750 inches (diameter) |
| D3 | 0.699, 0.700 inches (diameter) |
| W1 | 0.698, 0.700 inches |
| W2 | 0.385 ± 0.003 inches |
| A2 | 45.00 degrees |
| R1 | 0.32 inches radius thru flange align to octagon ± 3 degrees |

FIGS. 16A to 16D are more detailed illustrations of drive output assembly 543 that is representative of each drive output assembly in plurality of drive output assemblies 543P in this aspect. Drive output assembly 543 includes a ball-spline 1603. A light preload spring 1601, e.g., a first preload spring, is mounted in a central lumen of ball-spline 1603, and has one end affixed to a proximal side of drive output disk 545. Light preload spring 1601 applies a first preload force to drive output disk 545 when spring 1601 is compressed. In one aspect, the first preload force is 0.5 pounds force (Lbf).

A ball-spline nut 1604 is mounted is mounted on ball-spline 1603. Ball-spline nut 1604 slides proximally and distally along ball-spline 1603, i.e., slides in a first direction and in a second direction opposite to the first direction, while transferring torque/motion from ball-spline 1603. Thus, torque/motion is transferred to low backlash coupler 544, sometimes called flexure 544, through ball-spline 1603. Ball-spline 1603 transmits torque/motion, while allowing drive output assembly 543 to move along a longitudinal axis of ball-spline 1603. As disks are engaged or disengaged in disk stack 1400, drive output assembly 543 moves in and out along ball-spline 1603 to facilitate the engagement or disengagement. Ball-spline 1603 has zero backlash for torque levels used in surgical procedures.

Ball-spline nut 1604 is inserted in a housing 1605 on which heavy preload spring 1602, a second preload spring, is mounted. Heavy preload spring 1602 in combination with light preload spring 1601 applies a second preload force to drive output disk 545, when both springs are compressed. In one aspect, the second preload force is 2.3 pounds force (Lbf)

Flexure 544 is coupled to the drive unit by two pins that transmit torque from the drive unit to flexure 544. Flexure 544 is also coupled to drive output disk 545 by two pins. Thus, flexure 544 transfers torque from the drive unit to drive output disk 545. FIG. 16B is an end view of flexure 544.

Flexure 544 has a central lumen 1640 that fits on a cylinder 1445C (FIGS. 14 and 16A) extending proximally from a proximal surface of drive output disk 545. Flexure has four beams 1641A, 1641B, 1641C, and 1641D. A first end of each of four beams 1641A, 1641B, 1641C, and 1641D is connected to a body 1642 of flexure 544. A second end of each of four beams 1641A, 1641B, 1641C, and 1641D is connected to a cylinder 1643A, 1643B, 1643C, and 1643D, respectively, having a central bore. Beams 1641A, 1641B, 1641C, and 1641D are stiff in torsion about the axis through central lumen 1640, but flexible with respect to lateral offsets.

Output pins driven by the drive unit are mounted in the central bores of cylinders 1643A, 1643B. Input pins of drive output disk 545 are mounted in central bores of cylinders 1643C, 1643D.

Flexure 544 is a precision-machined one-piece part made of precipitation-hardened stainless steel 17-4 H1150, in one aspect. The backlash of flexure 544 is determined by the mounting pin clearances between the central bore of the cylinder and the outer diameter of the input pin or the output pin. The backlash of surgical device assembly 300 is controlled solely by instrument manipulator assembly 240, in this aspect. This is in contrast to previous systems where the backlash was accounted for by an Oldham coupling in the prior art sterile adapter. The parts in the prior art sterile adapter were injection molded and so could not be made to the same precision as flexure 544. Controlling backlash in a reusable part of surgical device assembly 300, e.g., instrument manipulator assembly 240, means that the backlash is consistent for each use of surgical device assembly 300 and is not dependent on the manufacturing tolerances of injection molded parts in a single-use disposable assembly, such as the prior art sterile adapter.

Flexure 544 accommodates motion in two-degrees of freedom in the plane normal to the axis of central lumen 1640. Output pins coupled to beams 1641A, 1641B can move along axis 1690. The range of motion is limited by the gap between the outer surface of cylinder 1643A, 1643B and the outer surface of body 1642. Similarly, input pins coupled to beams 1641C, 1641D can move along axis 1691, which is perpendicular to axis 1690. The range of motion is limited by the gap between the outer surface of the cylinder 1643C, 1643D and the outer surface of body 1642. In one aspect, to displace a beam 0.010 inches along one of axes 1690, 1691 takes 0.66 Lbf and results in 29,000 pounds per square inch stress. At 100 in-Lbf applied torque, the peak stress was 38,000 pounds per square inch.

The two degrees of freedom of flexure 544 accommodate shaft misalignment.

Specifically, drive unit assembly 541 can tolerate misalignment of drive shafts in motor pack 1541 with shafts in transmission unit 965, because each flexure 544 transfers torque to drive output disk 545 while flexing to compensate for a shaft 1466 (FIG. 14) that is not perfectly co-axial with the corresponding drive shaft of drive unit 1500.

Figure 16C:
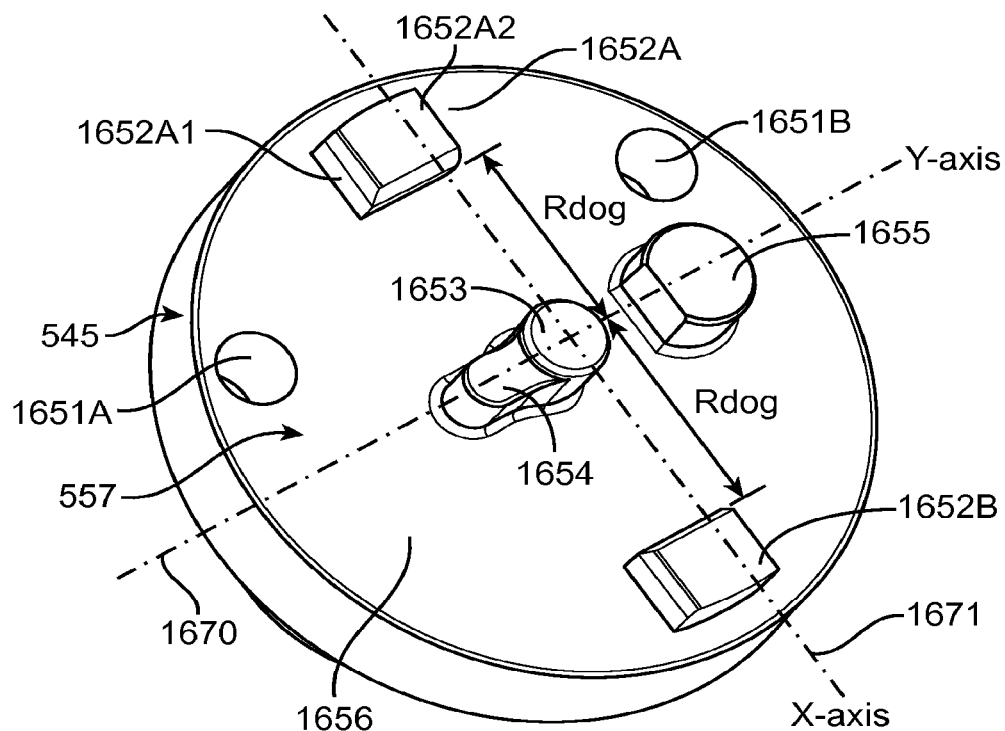
FIG. 16C is an illustration of a drive interface on the drive output disk.
Figure 16D:
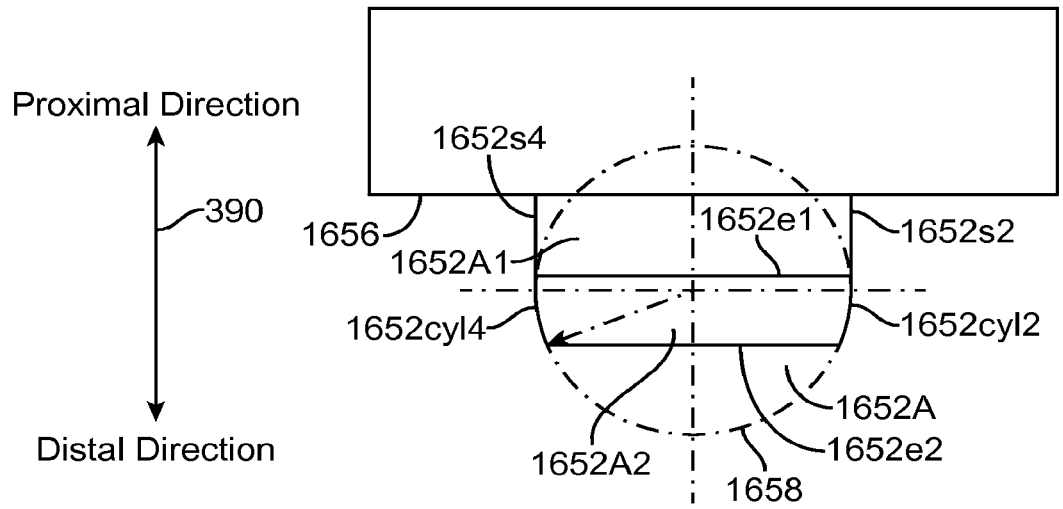
FIG. 16D is a cross-sectional view of a drive dog.

FIG. 16C is a more detailed illustration of one aspect of a drive interface 557 of drive output disk 545, e.g., the distal part of drive output disk 545. Drive output disk 545 has a cylindrical body. FIG. 16D is a cross-sectional view of drive output disk 545 with drive dog 1652A.

Two bores 1651A, 1651B extend through drive output disk 545. An input pin is fitted in each bore 1651A, 1651B and into a corresponding bore in cylinders 1643A, 1643B of flexure 544.

Two drive dogs 1652A, 1652B, a first alignment element—center post 1653 and tab 1654—and a second alignment element, pin 1655, extend distally from a distal end surface 1656 of drive output disk 545. Center post 1653 has a height that is larger than a height of tab 1654 and so helps to center drive output disk 545 with respect to a corresponding alignment receptacle in intermediate driven interface 655 of intermediate disk 653. Tab 1654 extends from center post 1653 towards a circumferential edge of distal end surface 1656. Centerlines 1670 and 1671 extend through and intersect at the center of center post 1653. Center post 1653 and tab 1654 assist in aligning drive output disk 545 to intermediate disk 653. Center post 1653 and tab 1654 also provide stability to the mated pair of disks.

Pin 1655, in this aspect, is also centered on centerline 1670 and is positioned between center post 1653 and an edge of distal end surface 1656. Pin 1655 is a segment of a cylinder, e.g., the cylinder has been cut vertically by a plane to so that a portion of the outer surface of pin 1655 is flat and not cylindrical. In one aspect, pin 1655 has a generally three-dimensional D-shape. Here, a generally three-dimensional D-shape means that the shape is similar enough to a three-dimensional D-shape to be recognized as a three-dimensional D shape, e.g., the shape of pin 1655. Pin 1655 is configured to mate with an alignment receptacle in intermediate disk 653.

The shape and orientation of the first and second alignment elements is illustrative only and is not intended to be limiting. Other shapes of the alignment elements and other orientations between the alignment elements may be used so long as backlash is not introduced under the second preload force, the elements do not bind when engaging and disengaging, and the elements provide stability to the mated pair of disks.

Drive interface 557 includes two drive dogs 1652A, 1652B. Each of drive dogs 1652A, 1652B extend distally from distal end surface 1656. Each of drive dogs 1652A, 1652B is a same radial distance Rdog from a longitudinal axis of drive output disk 545. The longitudinal axis of drive output disk 545 runs through the center of center post 1653. Also, each drive dog 1652A, 1652B is close to the circumferential edge of distal end surface 1656. The combination of radially equidistant drive dogs 1652A, 1652B and positioning drive dogs 1652A, 1652B adjacent the circumferential edge allows drive dogs 1652A, 1652B to efficiently transfer torque/motion to intermediate disk 653.

Figure 18A:
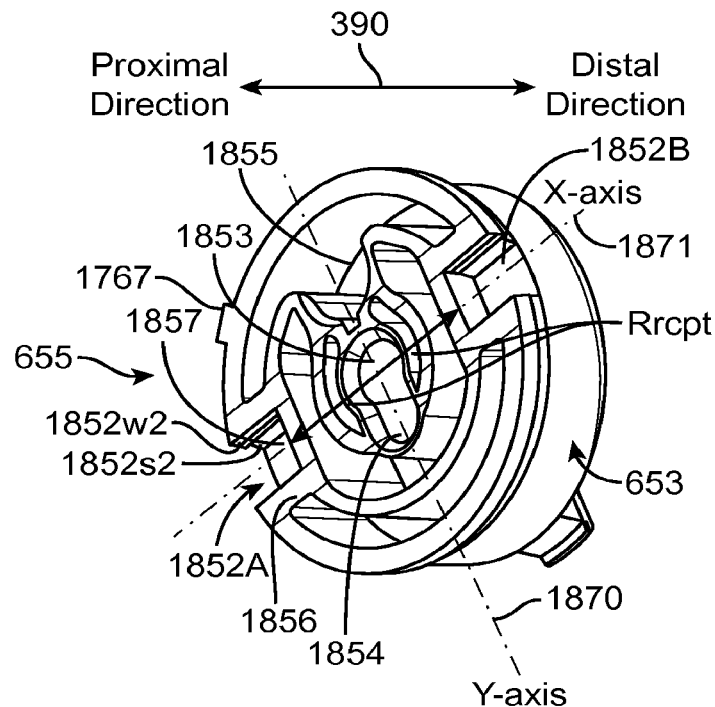
FIG. 18A is an illustration of the intermediate driven interface on the proximal end of the intermediate disk.

The location of the drive dogs 1652A, 1652B relative to the circumferential edge of distal end surface 1656 is determined by the location of drive dog receptacles on intermediate disk 653 (see FIG. 18A). The diameter of intermediate disk 653 is determined, in part, by the number of intermediate disks 653 that can fit in movable body 651C of sterile adapter assembly 250. Drive dogs 1652A, 1652B are sized and positioned so that drive dogs 1652A, 1652B engage the drive dog receptacles in intermediate disk 653, as described more completely below, and so that drive dogs 1652A, 1652B do not contact the sidewall of movable body 651C.

As illustrated in FIG. 16C, drive dogs 1652A, 1652B have mirror symmetry with respect to a plane that includes y-axis 1670 and a longitudinal axis (not shown) of drive output disk 545. The longitudinal axis of drive output disk 545 is perpendicular to both axis 1670 and axis 1671 at the center of center post 1653.

Each of drive dogs 1652A, 1652B has mirror symmetry with respect to a plane that includes x-axis 1671 and the longitudinal axis of drive output disk 545. This plane bisects each of drive dogs 1652A, 1652B.

The size of drive dogs 1652A, 1652B is selected based on strength requirements. A length of drive dogs 1652A, 1652B (radially from center to edge) in this application is determined by size constraints of the alignment features/antirotation features in the center of disk 545, and the height of drive dogs 1652A, 1652B is minimized to reduce the size and weight of the mechanism while assuring proper engagement with intermediate disk 653 under both the first and second preload forces.

Drive dog 1652A is the same as drive dog 1652B and so only the characteristics of drive dog 1652A are considered in further detail. The description of drive dog 1652A is directly applicable to drive dog 1652B and so the description is not repeated for drive dog 1652B.

Drive dog 1652A has a first portion 1652A1 and a second portion 1652A2. First portion 1652A1 extends distally from distal end surface 1656 to second portion 1652A2. Second portion 1652A2 extends from first portion 1652A1 in the distal direction.

First portion 1652A1 of drive dog 1652A is a three-dimensional rectangle and so has four straight sides extending from distal end surface 1656, e.g., sides 1652s2, 1652s4 in FIG. 16D. Herein, straight means substantially parallel to plane including a longitudinal axis of drive dog 1652A and one of x-axis 1671 and y-axis 1670. The axis chosen depends on the side of the three-dimensional rectangle being considered. Substantially parallel means parallel to within manufacturing tolerances.

Second portion 1652A2 (FIG. 16D) includes two opposing sides 1652cyl2, 1652cyl4 that are curved surface. In one aspect, the curved surface is a portion of a circular section, e.g., a portion of an outer surface of a cylinder 1658. Side surfaces 1652cyl2, 1652cyl4 are outer surfaces of a section of cylinder intersected by two parallel planes that include edges 1652e1, 165e2 and that extend out of FIG. 16D. Thus, side surfaces 1652cyl2, 1652cyl4 are curved surfaces.

In one aspect, cylinder 1658 has a diameter of 0.125 inches. The axis of cylinder 1658 extends out of FIG. 16D. In this aspect, the other two sidewalls of second portion 1652A2 are straight sides.

In one aspect, drive output disk 545 is an injection-molded disk. Drive output disk 545 can be made from polycarbonate, polyphenlysulfone (PPSU), polyethylenimine (PEI), etc.

Figure 17A:
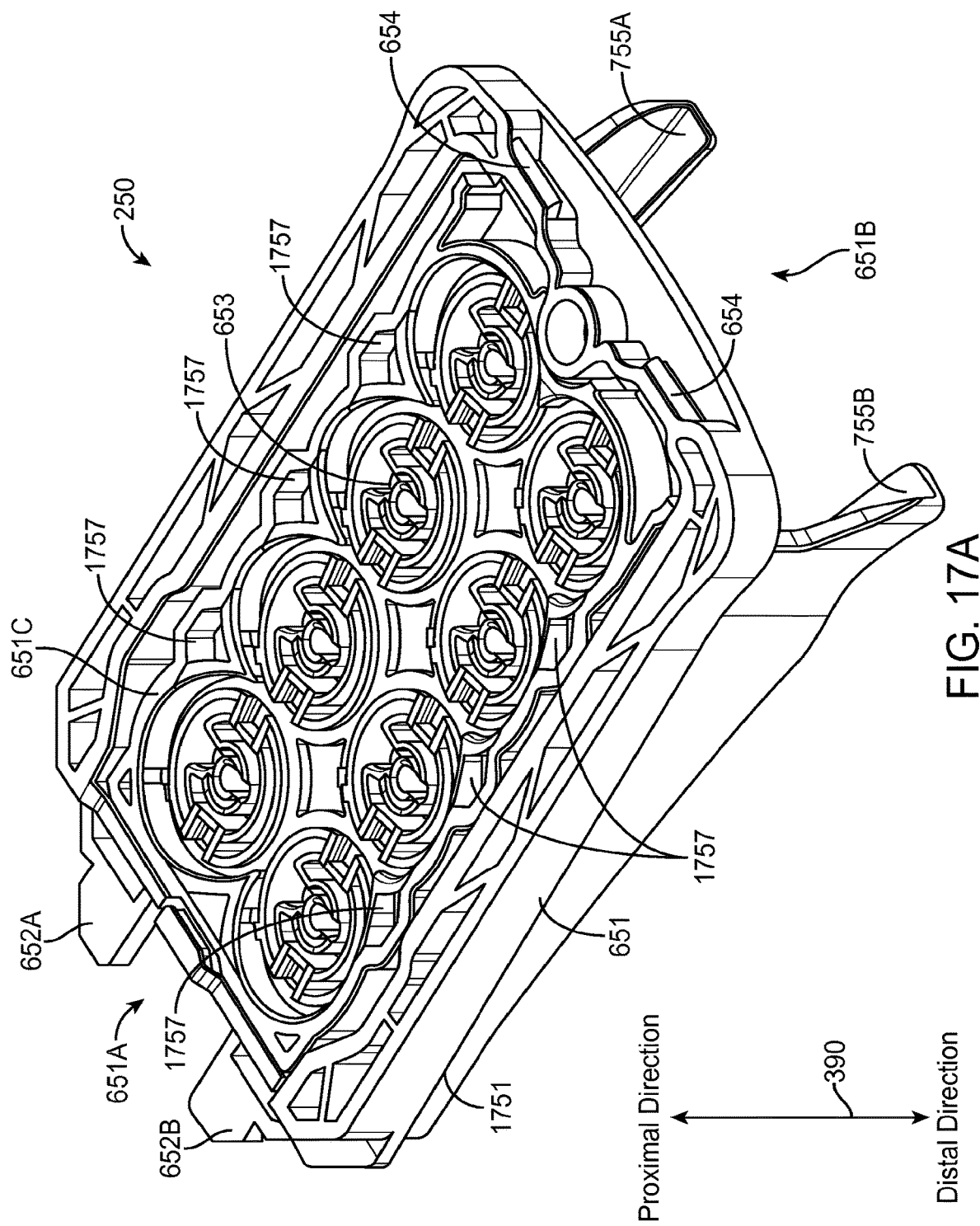
FIG. 17A is an illustration of the sterile adapter assembly.

FIG. 17A is another illustration of sterile adapter assembly 250. A sterile drape (not shown) is fixedly attached to a rim 1751, e.g., is affixed by two-sided tape. Sterile drapes are known and so are not described in further detail. See for example, U.S. Pat. No. 7,666,191 B2 (filed Dec. 20, 2005), U.S. Pat. No. 7,699,855 B2 (filed Mar. 31, 2006), U.S. Patent Application Publication No. US 2011/0277775 A1 (filed Aug. 12, 2010), and U.S. Patent Application Publication No. US 2011/0277776 A1 (filed Aug. 12, 2010), all of which are incorporated herein by reference. The sterile drape drapes at least a portion of system 200 to maintain a sterile field during a surgical procedure while sterile adapter assembly 250 also provides efficient and simple instrument exchange in conjunction with an accurate mechanical interface between surgical instrument 260 and its associated instrument manipulator assembly 240.

As indicated above, movable body 651C is mounted in sterile adapter frame 651 so that movable body 651C can move in the proximal and distal directions, i.e., can move in a first direction and in a second direction opposite to the first direction relative to the sterile adapter frame. In FIG. 17A, movable body 651C in the distal most position. Movable body 651C includes a receptacle for each intermediate disk 653 in plurality of intermediate disks 653P. Moveable body 651C also includes a plurality of hard stop receptacles 1757. Each intermediate disk 653 has a cylindrical body.

In one aspect, each of sterile adapter frame 651, movable body 651C, and the plurality of intermediate disks 653P are made by injection molding. Suitable materials for sterile adapter frame 651, movable body 651C, and plurality of intermediate disks 653P include polycarbonate, polyphenlysulfone (PPSU), polyethylenimine (PEI), etc.

Figure 17B:
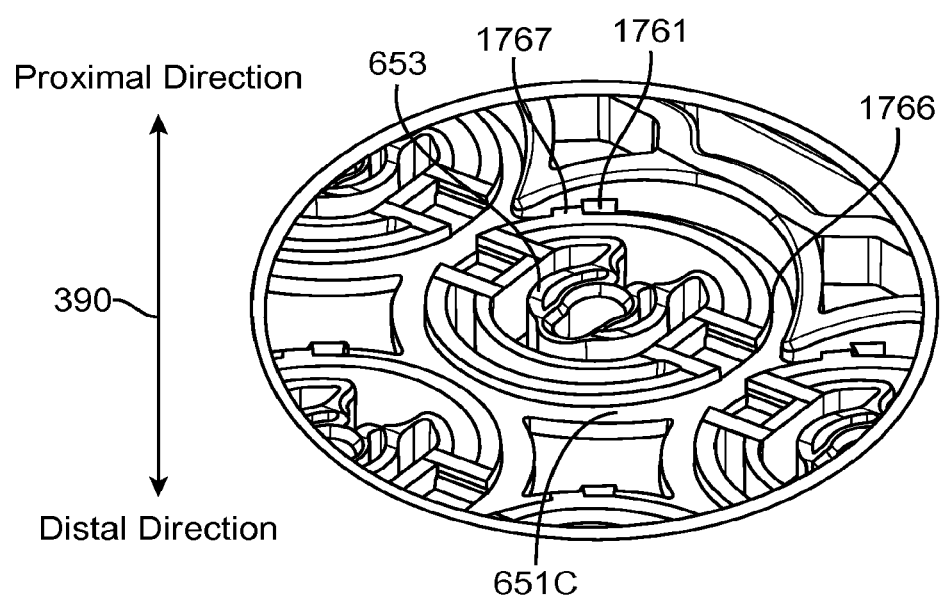
FIG. 17B is an enlarged illustration of a portion of the movable body showing a receptacle and an intermediate disk.

Each intermediate disk 653 is mounted in a corresponding receptacle in movable body 651C. Each intermediate disk 653 can rotate within the receptacle and can move distally and proximally in the receptacle. In FIG. 17A, intermediate disk 653 is in the most distal position. FIG. 17B is an enlarged illustration of a portion of movable body 651C showing an intermediate disk receptacle 1766 and intermediate disk 653. Intermediate disk 653 has a tab 1767 extending from an outer side surface of disk 653 and extending from the proximal end surface of disk 653 (see FIG. 18A). Intermediate disk 653 is said to be associated with an intermediate disk hard stop 1761. This means that tab 1767 can contact hard stop 1761 and upon contact, rotation of intermediate disk 653 is stopped.

When surgical instrument 260 is mounted on sterile adapter assembly 250, intermediate disk 653 is displaced proximally relative to movable body 651C. In this position, the most distal part of tab 1767, the bottom of tab 1767, is above the most proximal part of hard stop 1761, the top of stop 1761, so that intermediate disk 653 rotates freely and does not contact hard stop 1761.

Figure 18B:
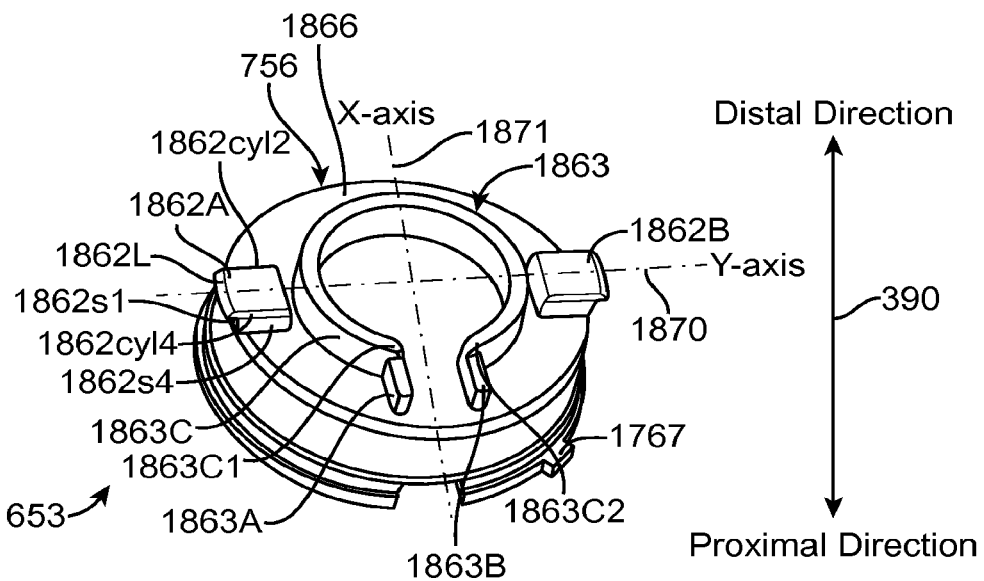
FIG. 18B is an illustration of the intermediate drive interface on the distal end of the intermediate disk.

FIGS. 18A and 18B are illustrations of intermediate driven interface 655 (FIG. 18A) and intermediate drive interface 756 (FIG. 18B) of intermediate disk 653. Intermediate driven interface 655 (FIG. 18A) is on a proximal end of intermediate disk 653. Intermediate driven interface 655 includes a first alignment receptacle and a second alignment receptacle. In this aspect, the first alignment receptacle is the combination of center post receptacle 1853 and tab receptacle 1854. The second alignment receptacle is pin receptacle 1855.

The combination of center post receptacle 1853 and tab receptacle 1854 is configured to mate with the combination of center post 1653 and tab 1654 when post 1653 and tab 1654 are aligned with receptacle 1853 and receptacle 1854, respectively. Similarly, pin receptacle 1855 is configured to mate with pin 1655 when the two are aligned. Thus, drive output disk 545 can only mate with intermediate disk 653 in one orientation, when the alignment elements of disk 545 are aligned with the alignment receptacles of intermediate disk 653.

Intermediate driven interface 655 also includes two drive dog receptacles 1852A, 1852B. As illustrated in FIG. 18A, drive dog receptacles 1852A, 1852B have mirror symmetry with respect to a plane that includes y-axis 1870 and a longitudinal axis (not shown) of intermediate disk 653. The longitudinal axis of intermediate disk 653 is perpendicular to both axis 1870 and axis 1871.

Each of drive dog receptacles 1852A, 1852B has mirror symmetry with respect to a plane that includes x-axis 1671 and the longitudinal axis of intermediate disk 653. This plane bisects each of drive dog receptacles 1852A, 1852B.

Each drive dog receptacle has an inner edge surface that is a same distance Rrcpt from a longitudinal axis of intermediate disk 653. The inner edge surface forms the third side of the drive dog receptacle, as explained more completely below. Since drive dog receptacle 1852A is the same as drive dog receptacle 1852B, only the characteristics of drive dog receptacle 1852A are considered in further detail. The description of drive dog receptacle 1852A is directly applicable to drive dog receptacle 1852B and so the description is not repeated for drive dog receptacle 1852B.

Drive dog receptacle 1852A can be bounded by four sides. In one aspect, a first side is not present, and so the first side is said to be open. The use of an open sidewall is illustrative only and is not intended to be limiting. In some aspects, the first sidewall can be a solid sidewall. Second and fourth sides are walls that are perpendicular to the first side. The third side is a wall that is perpendicular to the second and fourth sides. Thus, in this aspect, drive dog receptacle 1852A is bounded by three walls that extend from an outer proximal edge surface 1856 of intermediate disk 653 distally into intermediate disk 653 to a bottom surface 1857 of drive dog receptacle 1852A. The third wall that is opposite to the open side is a straight wall extending from outer proximal edge surface 1856 to bottom surface 1857. The two opposing walls, second and fourth walls, have two portions, as described below, a straight wall portion, and a sloped wall portion.

Figure 18C:
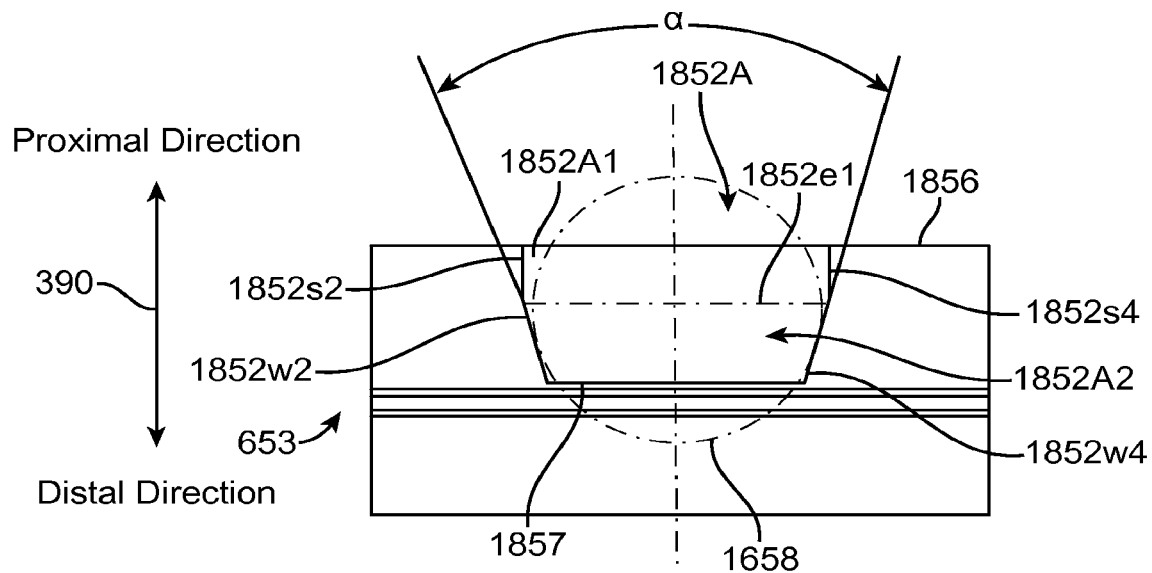
FIG. 18C is a cross-sectional view of a drive dog receptacle.

FIG. 18C is a cross-sectional view of drive dog receptacle 1852A cut along a centerline perpendicular to x-axis 1871. Drive dog receptacle 1852A is divided into a first portion 1852A1 and a second portion 1852A2. First portion 1852A1 extends into intermediate disk 653 from outer proximal surface 1856 to second portion 1852A2. Second portion 1852A2 extends further into intermediate disk 653 from first portion 1852A1 to bottom surface 1857 of drive dog receptacle 1852A.

Opposing walls that bound first portion 1852A1 of drive dog receptacle 1852A are straight walls 1852s2, 1852s4. Typically, a height of first portion 1852A1 is smaller than the height of portion 1652A1 of drive dog 1652A so that there is some space between the distal edge surface of drive output disk 545 and the proximal edge surface of intermediate disk 653.

Second portion 1852A2 (FIG. 18C) is bounded by two opposing sidewalls 1852w2, 1852w4 that are a portion of an outer side surface of a wedge shape, i.e., sides 1852w2, 1852w4 are a sloped flat surface. Sidewalls 1852w2, 1852w4 subtend an angle α. Side surfaces 1852w1, 1852w2 are the surface portions of the wedge shape intersected by two parallel planes, e.g., a plane that includes line 1852e1 and a plane that includes bottom surface 1857. Both of these planes extend out of FIG. 18C.

In one aspect, the portion of the wedge is selected so that when the distal end of drive dog 1652A is completely inserted in receptacle 1852, the distal end surface of drive dog 1652A does not contacts bottom surface 1857, and the cylindrical sidewall portions of cylinder 1658 contact sloped sidewalls 1852w2, 1852w4. In one aspect, for a 0.125 diameter of cylinder 1658, angle α is 30 degrees, so sidewalls 1852w2, 1852w4 are portions of sides of a 30-degree wedge shape.

When sterile adapter assembly 250 is mounted on instrument manipulator assembly 240, the orientation of drive interface 557 on drive output disk 545 with respect to the orientation of intermediate driven interface 655 on intermediate disk 653 is not known. However, irrespective of the relative orientation of the two interfaces, the preload force on drive output disk 545 pushes intermediate disk 653 distally so that intermediate disk 653 is positioned at the most distal portion in receptacle 1766 (FIG. 17B) of moveable body 651C, e.g., intermediate disk 653 is in a first axial position. As explained more completely below, when surgical instrument 260 is mounted in sterile adapter assembly 250, intermediate disk 653 is displaced proximally to a second axial position.

As described above, after plunger 546 is depressed by attaching sterile adapter assembly 250 to instrument manipulator assembly 240, drive output disk 545 is rotated. Since drive output disk 545 and intermediate disk 653 are in contact and partially coupled, rotation of drive output disk 545 rotates intermediate disk 653. Thus, either interfaces 557 and 655 align and mate, or tab 1767 on intermediate disk 653 contacts hard stop 1761. When tab 1767 contacts hard stop 1761, rotation of intermediate disk 653 is stopped. When interfaces 557 and 655 have not mated and rotation of intermediate disk 653 is stopped, drive output disk 545 continues to rotate until the two interfaces mate. Hence, the result is that disks 545 and 653 are coupled and rotation of drive output disk 545 is stopped at hard stop 1761. The control system uses the stopping of rotation of drive output disk 545 to determine the orientation of drive output disk 545. Note that if the two disks mated prior to reaching hard stop 1761, when hard stop 1761 is reached rotation of the two-mated disks is stopped.

Figure 18D:
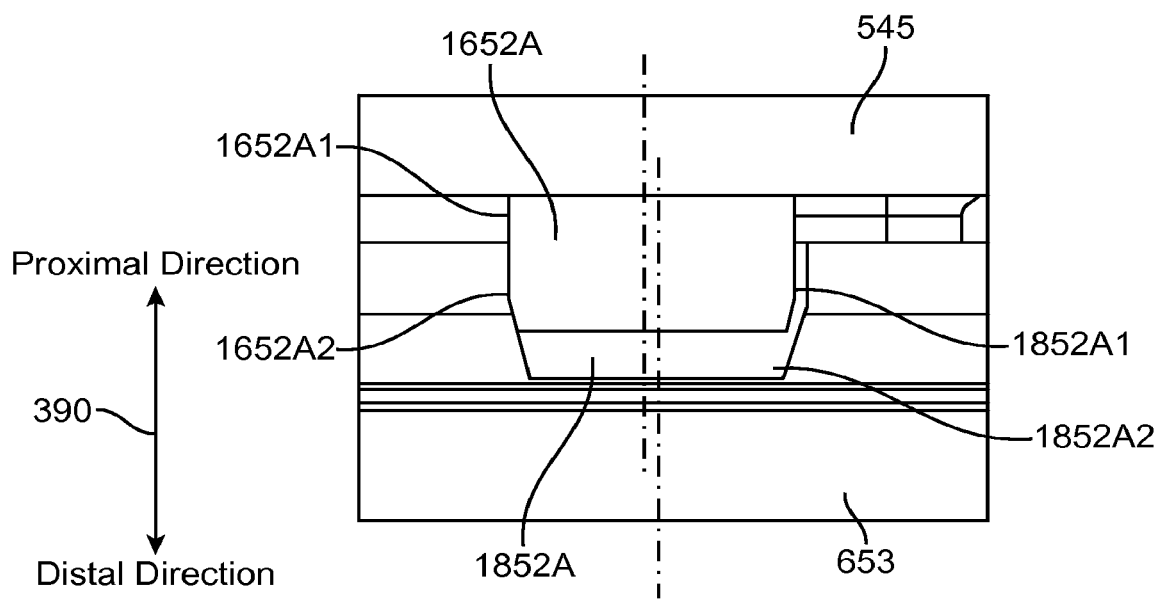
FIG. 18D is a cross sectional view that illustrates a drive dog inserted in a drive dog receptacle under the light preload force after the drive interface on the drive output disk has partially coupled with the intermediate driven interface on the intermediate disk.

FIG. 18D is a cross sectional view that illustrates drive dog 1652A inserted in drive dog receptacle 1852A under a light preload force after drive interface 557 on drive output disk 545 has partially-coupled with intermediate driven interface 655 on intermediate disk 653. As described above, drive dog 1652A has a first portion 1652A1 with straight sides. The straight sides of first portion 1652A1 blend into a second portion 1652A2, a cylindrical tip, as described above. Drive dog receptacle 1852A also has a first portion 1852A1 with straight internal sidewalls. First portion 1852A1 blends into a second portion 1852A2 with tapered internal walls also as described above.

Curved surfaces on two sides of the distal portion of drive dog 1652A and a sloped slide walls on the corresponding two sides on the distal portion of drive dog receptacle 1852A, where the sloped sidewall is tangent to the curved side surface, are illustrative only and is not intended to be limiting. Other surfaces on the distal portion of drive dog 1652A and on the corresponding distal wall portions of drive dog receptacle 1852A could be used so long as under the high preload force, the second preload force, there is zero backlash in the rotational direction between drive output disk 545 and intermediate disk 653 for torque levels used in surgical procedures, and so long as the interface between the two disks compensates for angular misalignment.

Due to the tapered walls of receptacle 1852A and the cylindrical surfaces on second portion 1652A2 of drive dog 1652A, an appropriate force is required to hold drive output disk 545 and intermediate disk 653 in place so that the two disks function properly when torque/motion is applied by drive output disk 545 while the two disks are partially coupled. In the absence of this force, drive output disk 545 and intermediate disk 653 can separate because the applied torque can drive them apart.

To prevent this separation under the light preload force, both drive dog 1652A and drive dog receptacle 1852A have the first portions with straight walls, as described above. As drive dog 1652A and drive dog receptacle 1852A start to separate under torque, the straight wall portions come into contact with one another as shown in FIG. 18C. At this point, drive dog 1652A and drive dog receptacle 1852A are no longer capable of driving themselves apart, and the motion can continue with a known or controlled level of backlash and without drive dog 1652A completely inserted into and coupled to drive dog receptacle 1852A. In one aspect, under the light preload force, the known level of backlash is 1.13 degrees. Thus, the partial coupling between drive output disk 545 and intermediate disk 653 has a known level of backlash under the light preload force.

Also, as shown in FIG. 18D, a small amount of misalignment between the shaft driving disk 545 and the shaft that is driven by intermediate disk 653 can be tolerated. In addition, angular misalignment can be tolerated in the direction defined by the axis of blending cylinder 1658 which is into and out of the page in FIG. 18D.

When drive dog 1652A and drive dog receptacle 1852A are mated together under the high preload force, e.g., the second preload force, as described more completely below, there is no backlash in the interface between the two disks. The second preload force is sufficient to keep drive dog 1652A and drive dog receptacle 1852A from physically backing apart and separating when torque/motion is applied. Thus, this joint can transmit torque/motion without backlash. Under the second preload force, the coupling between drive output disk 545 and intermediate disk 653 has zero backlash for torque levels used in surgical procedures.

FIG. 18B is a more detailed illustration of intermediate drive interface 756 on the distal end of intermediate disk 653. Intermediate drive interface 756 includes drive dogs 1862A, 1862B, and an engagement structure 1863C.

Each of drive dogs 1862A and 1862B is a structure that is equivalent to each of drive dogs 1652A and 1652B. Specifically, each of drive dogs 1862A, 1862B extend distally from distal end surface 1866. An inner edge of each of drive dogs 1862A, 1862B is a same radial distance from a longitudinal axis of distal end surface 1866. Also, each drive dog 1862A, 1862B is adjacent to the circumferential edge of distal end surface 1866. The combination of radially equidistant drive dogs 1862A, 1862B and of positioning of drive dogs 1862A, 1862B adjacent to the circumferential edge allows drive dogs 1862A, 1862B to efficiently transfer torque/motion to driven disk 964.

As illustrated in FIG. 18B, drive dogs 1862A, 1862B have mirror symmetry with respect to a plane that includes x-axis 1871 and a longitudinal axis (not shown) of intermediate disk 653. The longitudinal axis of intermediate disk 653 is perpendicular to both axis 1870 and axis 1871 at the intersection of axis 1870 and axis 1871.

Each of drive dogs 1862A, 1862B has mirror symmetry with respect to a plane that includes y-axis 1870 and the longitudinal axis (not shown). This plane bisects the drive dogs.

Drive dog 1862A is the same as drive dog 1862B and so only the characteristics of drive dog 1862A is considered in further detail. The description of drive dog 1862A is directly applicable to drive dog 1862B and so the description is not repeated for drive dog 1862B.

The cylindrical sidewall portions of drive dog 1862A and the straight wall portions of drive dog 1862B are the same as the corresponding portions of drive dog 1652A, and so the description of these portions is not repeated here. As shown in FIG. 18B, a lip 1862L extends radially outward from the distal end of the second portion of drive dog 1862A. Two sidewalls 1862s2, 1862s4 are perpendicular to sidewall 1862s1 and lip 1862A1 extends radially outward from sidewall 1862s1. Lip 1862L is a retention feature that retains intermediate disk 653 in movable body 651C.

Engagement structure 1863C, in this aspect, is an open three-dimensional structure. Open three-dimensional structure has mirror symmetry with respect to a plane including the longitudinal axis of intermediate disk 653 and axis 1871, in this aspect. Here, an open three-dimensional structure means a three-dimensional structure that does not have a closed perimeter, i.e., there is an opening at which an outer side surface meets an inner side surface. In the example of FIG. 18D, the open three-dimensional structure includes two parts—a generally three-dimensional letter C-shaped structure 1863C and two walls 1863A, 1863B. Again, here a generally three-dimensional letter C-shaped structure is a three-dimensional structure that is perceived as a three-dimensional letter C-shaped structure by a person viewing the structure.

Three-dimensional letter C-shaped structure 1863C has a height, a first end 1863C1, and a second end 1863C2. The height of structure 1863C extends distally from distal end surface 1866 of intermediate disk 653, which could be called a distal face of intermediate disk 653, to the most distal end surface or most distal edge of structure 1863C. First end 1863C1 and second end 1863C2 bound an opening of C-shaped structure 1863C. Axis 1871, in this aspect, is equidistant from first end 1863C1 and from second end 1863C2 and is a centerline of C-shaped structure 1863C.

C-shaped structure 1863C is an example of an open three-dimensional structure that is a circular track. The circular track includes a first circumferential section having a first height, a first end, and a second end, e.g., the body of the C-shaped structure. The circular track also includes a second circumferential section extending between the first and second ends of the first circumferential section, e.g., the gap between the ends of the C-shaped structure. The second circumferential section has a second height. The second height is less than the first height. A centerline of the circular tracks extends through a center of the circular track and is equidistance from the first and second ends.

Wall 1863A abuts first end 1863C1 and extends towards the circumferential edge of distal end surface 1866. Wall 1863B abuts second end 1863C2 and extends towards the circumferential edge of distal end surface 1866. Wall 1863A and wall 1863B have a same height. The height of wall 1863A and of wall 1863B extends distally from distal end surface 1866 of intermediate disk 653 to the most distal end surface or most distal edge of wall 1863A and of wall 1863B. The height of walls 1863A and 1863B is smaller than the height of C-shaped structure 1863C.

As illustrated in FIGS. 18A and 18B, the axis that bisects drive dog receptacles 1852A, 1852B, i.e., x-axis 1871, is perpendicular to the axis that bisects drive dogs 1862A, 1862B. When all the discs are mated as in disc stack 1400, the axis of allowed rotation for intermediate disk 653 and driven disk 964 is 90 degrees to the axis of allowed rotation for intermediate disk 653 and drive output disk 545. Stated another way, each of drive dog receptacles 1852A, 1852B of intermediate disk 653 is positioned so that each of drive dog receptacles 1852A, 1852B is bisected by a first plane. Each of drive dogs 1862A, 1862B of intermediate disk 653 is positioned so that each of drive dogs 1862A, and 1862B is bisected by a second plane. The first plane is perpendicular to the second plane.

The coupling of the interfaces between intermediate disk 653 and drive output disk 545 forms a first joint, while the coupling of the interfaces between intermediate disk 653 and driven disk 964 forms a second joint. Together these two working joints accommodate angular misalignment as the system rotates and transmits motion/torque. The two joints act like a set of U-Joints.

Figure 19A:
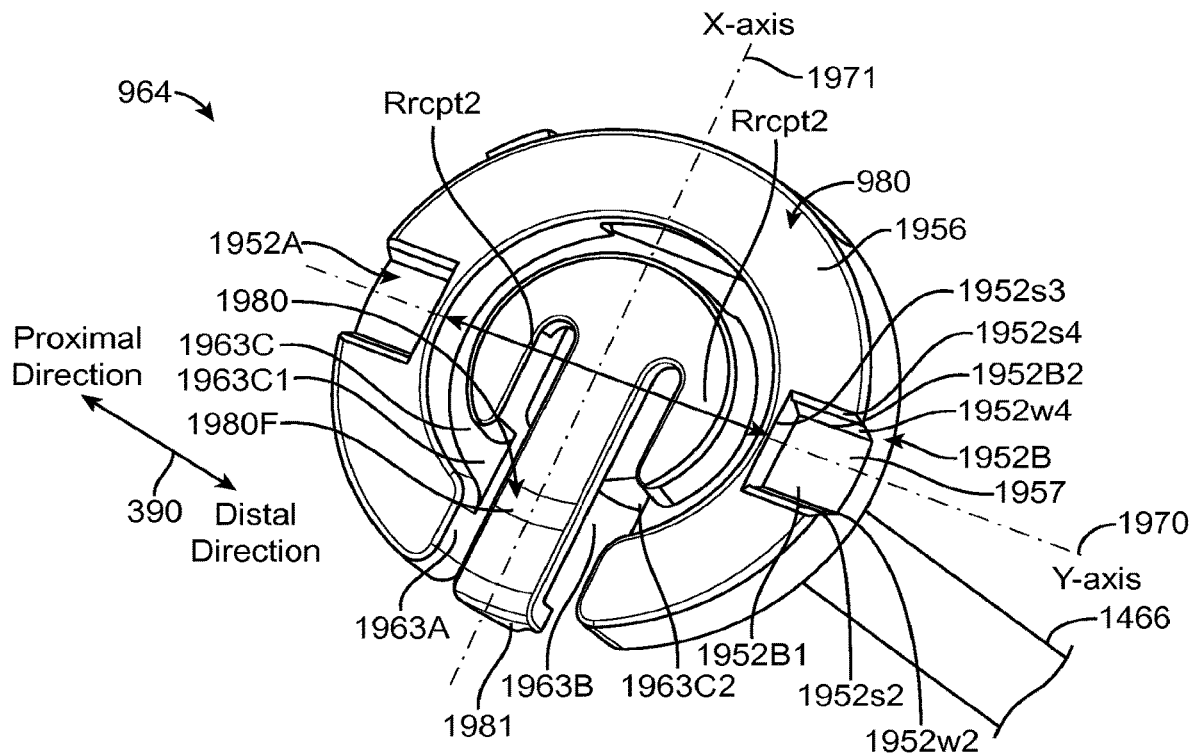
FIG. 19A is an illustration of the driven interface on a proximal end of the driven disk.

FIG. 19A is an illustration of driven interface 980 on a proximal end of driven disk 964. Driven interface 980 includes an engagement receptacle, drive dog receptacles 1952A, 1952B, and a rotation disable element 1980. As explained more completely below, rotation disable element 1980 includes a rotation locking mechanism 1981.

Drive dog receptacles 1952A, 1952B have mirror symmetry with respect to a plane that includes x-axis 1971 and a longitudinal axis (not shown) of driven disk 964. The longitudinal axis of driven disk 964 is perpendicular to the intersection of axis 1970 and axis 1971. Each of drive dog receptacles 1952A, 1952B has mirror symmetry with respect to a plane that includes y-axis 1970 and the longitudinal axis of driven disk 964. This plane bisects the drive dog receptacles. Each drive dog receptacle has an inner edge surface that is a same distance Rrcpt2 from the longitudinal axis of driven disk 964. Since drive dog receptacle 1952A is the same as drive dog receptacle 1952B, only the characteristics of drive dog receptacle 1952B are considered in further detail. The description of drive dog receptacle 1952B is directly applicable to drive dog receptacle 1952A and so the description is not repeated for drive dog receptacle 1952A.

Drive dog receptacle 1952B can be bounded by four sides. Second and fourth sides are walls that are perpendicular to a first side. The third side is a wall that is perpendicular to the second and fourth sides. However, in this aspect, a first of four sides is missing and so is referred to as an open first side. The use of an open sidewall is illustrative only and is not intended to be limiting. In some aspects, the first sidewall can be a solid sidewall.

Thus, in this aspect, drive dog receptacle 1952B is bounded by three walls that each extends from an outer proximal edge surface 1956 of driven disk 964 to a bottom surface 1957 of drive dog receptacle 1952B. The third wall that is opposite to the open side is a straight wall 1952s3 extending from outer proximal edge surface 1956 to bottom surface 1957. The two opposing walls, second and fourth walls, have two portions, straight wall portions 1952s2, 1952s4, and a sloped wall portion 1952w2, 1952w4.

Thus, drive dog receptacle 1952B is divided into a first portion 1952B1 and a second portion 1952B2. First portion 1952B1 extends into driven disk 964 from an outer proximal edge surface 1956 to second portion 1952B2. Second portion 1952B2 extends further into driven disk 964 from first portion 1952B1 to bottom surface 1957 of drive dog receptacle 1952B. The other characteristics of drive dog receptacle 1952B are the same as the characteristics described above for drive dog receptacle 1852A and so that description is applicable to drive dog receptacle 1953B and is not repeated here.

Engagement receptacle 1963, in this aspect, includes an open three-dimensional groove formed in the proximal end of driven disk 964. The open three-dimensional groove extends distally into driven disk 964 from outer proximal edge surface 1956. Here, an open three-dimensional groove means a three-dimensional groove that does not have closed inner and outer perimeters. In the example of FIG. 19A, the open three-dimensional groove is a generally three-dimensional letter C-shaped groove 1963C that has a width and a depth.

Three-dimensional letter C-shaped groove 1963C has a first end 1963C1 and a second end 1963C2. First end 1963C1 and second end 1963C2 are separated from rotation disable element 1980 by a first gap 1963A and a second gap 1963B, respectively.

In this aspect, rotation disable element 1980 includes a flexure 1980F with rotation locking mechanism 1981 at one end. In this aspect, flexure 1980F extends radially outward from a center region of the proximal end of driven disk 964 towards the sidewall of driven disk 964. The center region is bounded by C-shaped groove 1963C. Rotation locking mechanism 1981 extends in a distal direction from an end of flexure 1980F. Rotation locking mechanism 1981 forms part of a sidewall of disk 964. The most distal end of rotation locking mechanism 1981 is a tang, in this aspect.

Figure 19B:
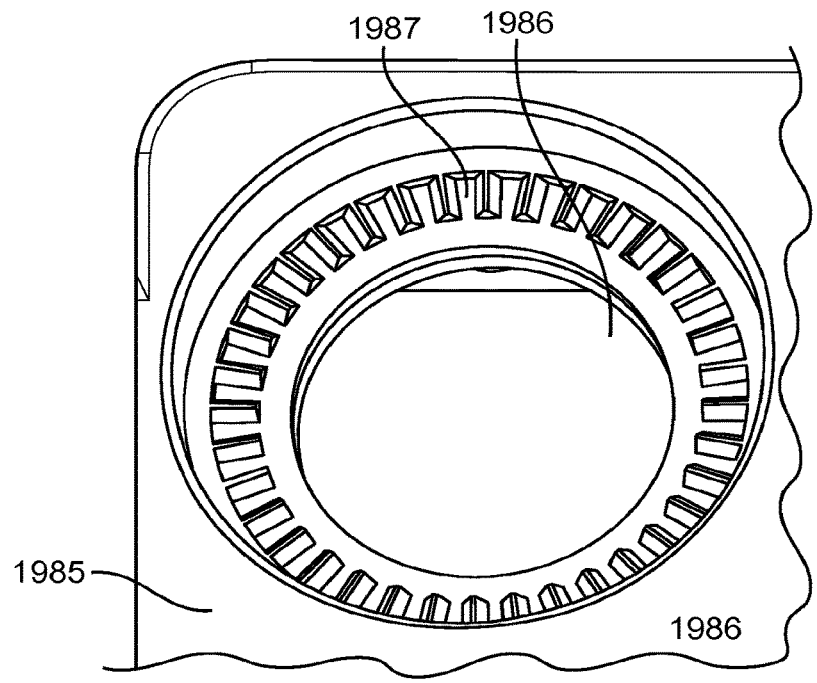
FIG. 19B is an illustration of a part of the body of the driven interface assembly.

FIG. 19B is an illustration of a part of body 1985 of driven interface assembly 961. Body 1985 includes a driven disk receptacle 1986. A plurality of gear teeth 1987 extend in the proximal direction from a bottom surface of driven disk receptacle 1986. Body 1985 includes a driven disk receptacle 1986 for each driven disk 964 in plurality of driven disks 964P.

Shaft 1466 of transmission unit 965 has a proximal end that extends into driven disk receptacle 1986. Driven disk 964 is mounted on the proximal end of shaft 1466 so that driven disk 964 is positioned in driven disk receptacle 1986 and can rotate within driven disk receptacle 1986.

Figure 20A:
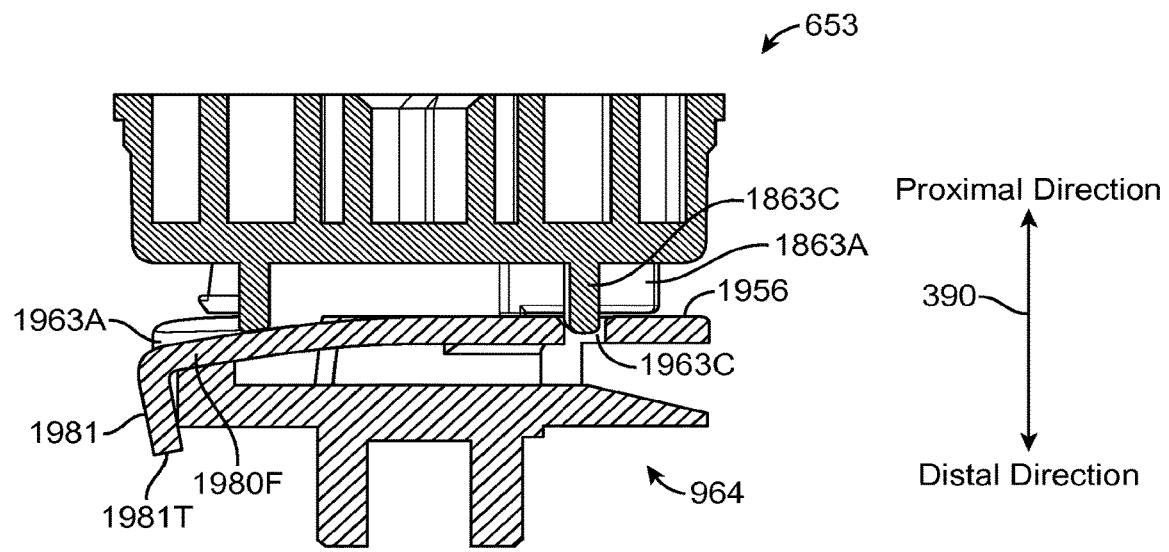
FIG. 20A illustrates a cut-away view of when the intermediate disk and the driven disk are in contact, i.e., partially coupled, but are not mated.

When surgical instrument 260 is first mounted in sterile adapter assembly 250, driven disk 964 in driven interface assembly 961 pushes intermediate disk 653 in sterile adapter assembly 250 proximally relative to movable body 651C so that the intermediate disk 653 can rotate freely, e.g., tab 1767 on intermediate disk 653 is moved proximally so that tab 1767 no long contacts hard stop 1761 as intermediate disk 653 rotates. Typically, when surgical instrument 260 is first mounted in sterile adapter assembly 250, intermediate drive interface 756 of intermediate disk 653 in sterile adapter assembly 250 is not aligned with driven interface 980 of driven disk 964. Thus, intermediate disk 653 and driven disk 964 are not mated. FIG. 20A illustrates a cut-away view of when intermediate disk 653 and driven disk 964 are in partial contact, i.e., are partially coupled.

When intermediate disk 653 and driven disk 964 are put in contact and partially coupled, C-shaped structure 1863C is partially inserted in C-shaped groove 1963C. However, wall 1863A is not aligned with gap 1963A and wall 1863B is not aligned with gap 1963B. Thus, C-shaped structure 1863C only goes into C-shaped groove 1963C until walls 1863A, 1863B contact proximal outer edge surface 1956 of driven disk 964.

A part of C-shaped structure 1863C rests on flexure 1980F and deflects flexure 1980F in the distal direction. The deflection of flexure 1980F moves rotation-locking mechanism 1981 distally so that tang 1981T engages teeth 1987 on the bottom surface of driven disk receptacle 1986. The engagement of tang 1981T with teeth 1987 prevents driven disk 964 from rotating.

Figure 20B:
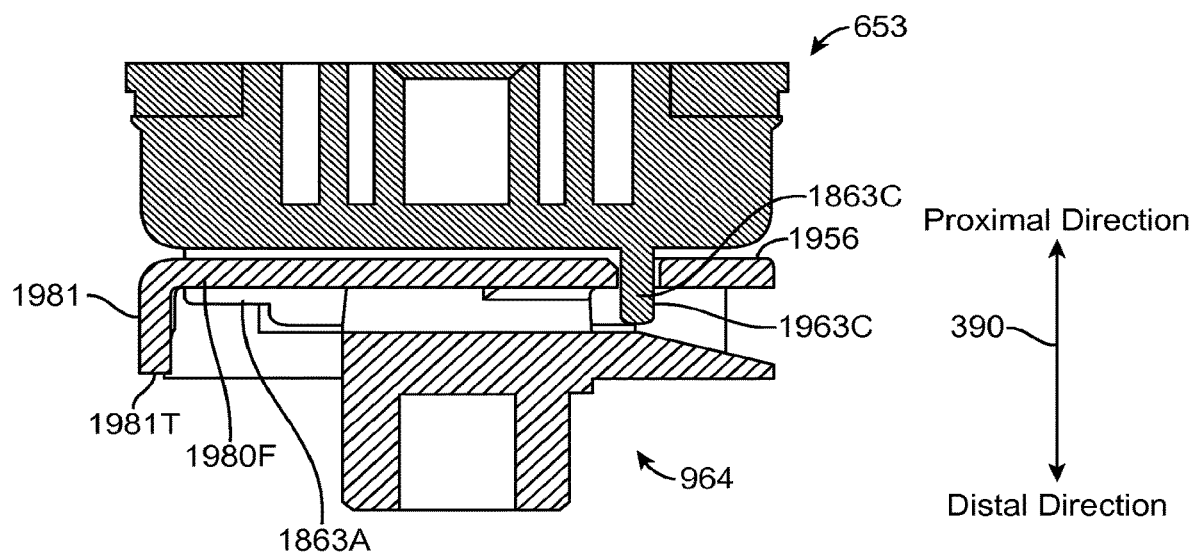
FIG. 20B illustrates a cut-away view of when the intermediate disk and the driven are mated.

Thus, as driven disk 964 is held stationary and intermediate disk 653 is rotated, walls 1863A and 1863B become aligned with gap 1963A and gap 1963B, respectively, and the preload force causes C-shaped structure 1863C to insert completely into C-shaped groove 1963C and walls 1863A and 1863B to insert into gap 1963A and gap 1963B, respectively. Also, each of the drive dogs is inserted into the corresponding drive dog receptacle. Since C-shaped structure 1863C is no longer pushing on flexure 1980F, flexure 1980F returns to the undeflected state (FIG. 20B). This disengages tang 1981T from teeth 1987 and so driven disk 964 can rotate. Hence, driven disk 964 has coupled with intermediate disk 653 so that torque is transferred to shaft 1466.

Flexure 1980F is illustrative only and is not intended to be limiting. For example, a spring-loaded pin could be included in the driven disk 964 so that C-shaped structure 1863C depressed the pin until intermediate disk 653 and driven disk 964 were coupled. The depressed pin could push on a flexure in the distal end of driven disk 964 that includes a tang on one end. The tang would engage teeth 1987 until the force on the flexure was removed. Alternatively, the spring-loaded pin could engage teeth 1987 to prevent rotation.

After surgical instrument 260 is mounted on sterile adapter assembly 250 and the intermediate disks are coupled with the driven disks, motion/torque can be transferred from drive unit assembly 541 to transmission unit in surgical instrument 260. However, as described above, under the first preload force that is supplied by the compression of spring 1601, there is some backlash in disk stack 1400.

Under the first preload force, the coupling between intermediate disk 653 and driven disk 964 and the coupling between drive output disk 545 and intermediate disk 653 have a known non-zero backlash for torque levels necessary to bring the two disks into alignment. However, for lower torque levels, the partial coupling between drive output disk 545 and intermediate disk 653 has zero backlash. To reduce the backlash of the coupling between intermediate disk 653 and driven disk 964 and of the coupling between drive output disk 545 and intermediate disk 653 to zero for torque levels used in surgical procedures, the preload force is changed from the first preload force to the second preload force using preload assembly 780.

Figure 21:
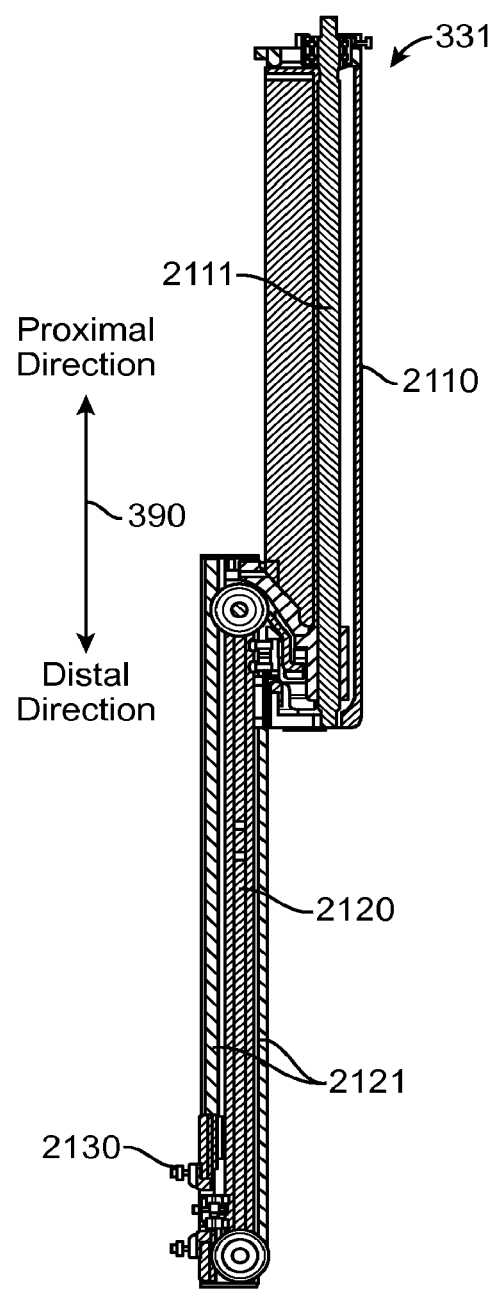
FIG. 21 is a more detailed illustration of one aspect of the insertion assembly.

FIG. 21 is a more detailed illustration of one aspect of insertion assembly 331. Insertion assembly 331 includes a frame 2110, a mid-carriage 2120, and a distal carriage 2130. Mid-carriage 2120 rides on a ball screw 2111 in frame 2110. In one aspect, ball screw 2111 has a 6 mm pitch and so is back drivable. Mid-carriage 2120 includes metal belts 2121 that drive distal carriage 2130. Distal carriage 2130 is attached to instrument manipulator assembly housing 741 of instrument manipulator assembly 240. Distal carriage 2130 moves twice as far as mid-carriage 2120 in one aspect.

Figures 22A, 22B:
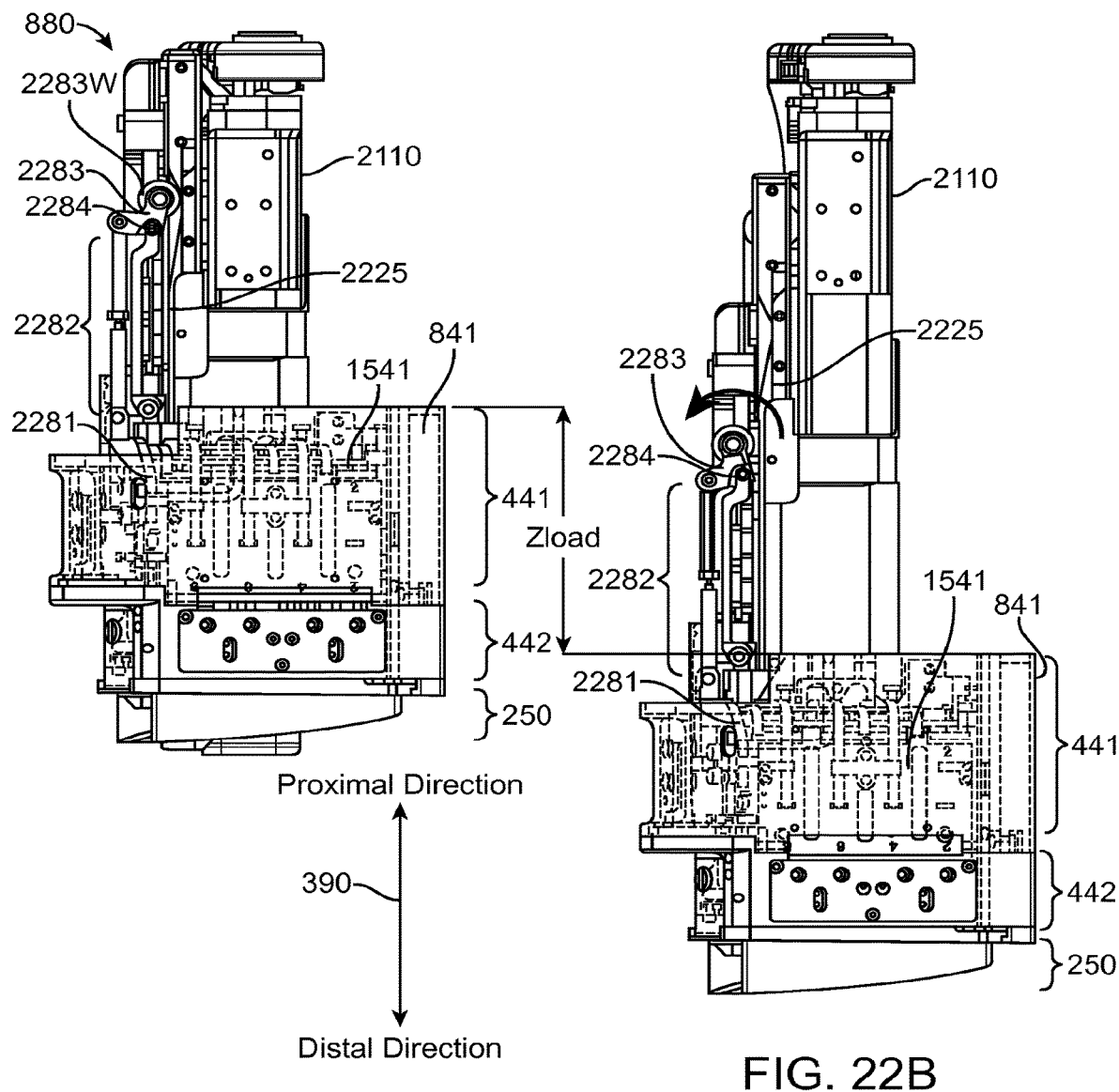
FIGS. 22A and 22B illustrate a preload assembly in greater detail.

FIGS. 22A and 22B illustrate preload assembly 780 in greater detail. In FIGS. 22A and 22B, surgical instrument 260 is mounted in sterile adapter assembly 250. However, for ease of illustration, surgical instrument 260 is not shown in FIGS. 22A and 22B. The distal end of surgical instrument is, for example positioned at an entry to a channel in entry guide 270.

Initially, as shown in FIG. 22A, cam follower assembly 2283 in preload assembly 780 is positioned in a valley in a preload track 2225 on mid-carriage 2120, e.g., is positioned at a first location on preload track 2225. Preload track 2225 is mounted on mid-carriage 2120. The valley is located at a proximal end of preload track 2225. Cam follower assembly 2283 is rotatably connected to a first end of an arm 2282 in preload assembly 780. A second end of arm 2282 is connected to a motor pack bracket 2281. Motor pack bracket 2281 is affixed to motor pack 1541. Thus, arm 2282 is coupled to motor pack 1541. In FIGS. 22A and 22B, instrument manipulator assembly housing 741 is transparent so that the features and elements within instrument manipulator assembly housing 741 are visible. As indicated above, instrument manipulator assembly housing 741 is affixed to distal carriage 2130

At the first location, light preload spring 1601 in each drive output assembly 543 has been compressed, and the first preload force is applied to each disk in disk stack 1400. As surgical device assembly 300 is moved distally a distance Zload by insertion assembly 331 from the first location (FIG. 22A) to a second location (FIG. 22B) instrument manipulator assembly housing 741 is moved distance Zload.

Pivot pin 2284, on which cam follower assembly 2283 is rotatably mounted, is coupled to instrument manipulator assembly housing 741 of instrument manipulator assembly 240. Thus, as insertion assembly 331 moves instrument manipulator assembly housing 741 distally a distance Zload, pivot pin 2284 moves cam follower assembly 2283 the same distance Zload. In one aspect distance Zload is 3.85 inches.

A wheel 2283W is rotatably attached to a first end of cam follower assembly 2283, and wheel 2283W rides on preload track 2225. Thus, as cam follower assembly 2283 moves distally, wheel 2283W follows the contour of preload track 2225. However the distance between preload track 2225 and pivot point 2284 diminishes as cam follower assembly 2283 moves distally. Consequently, as cam follower assembly 2283 rides up ramp 2225R in preload track 2225, cam follower assembly 2283 rotates from a first position illustrated in FIG. 22A to a second position as illustrated in FIG. 22B and moves motor pack 1541 a distance that is greater than the distance traveled by instrument manipulator assembly housing 741. Thus, the rotation of cam follower assembly 2283 displaces motor pack 1541 a predetermined distance distally relative to instrument manipulator assembly housing 741.

Figure 22C:
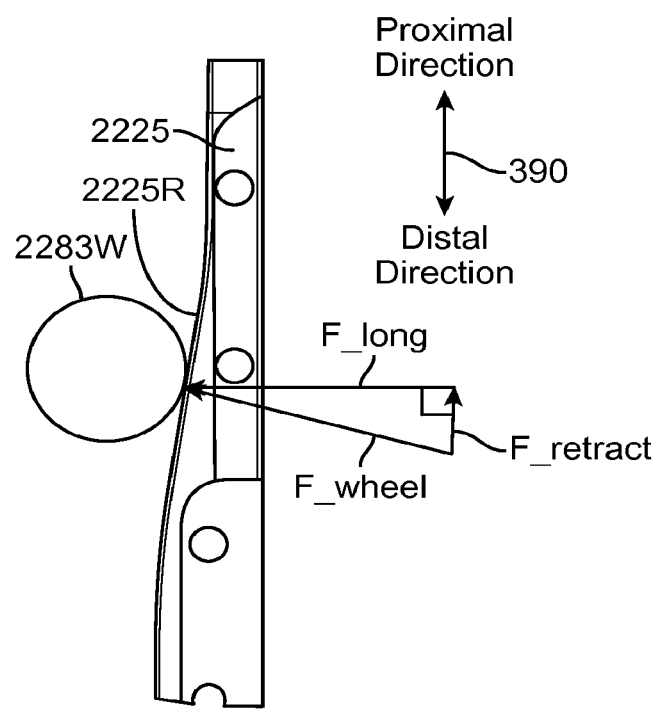
FIG. 22C is a free body force diagram of the forces acting on a wheel in the cam follower assembly of the preload assembly.

To understand the forces acting on cam follower assembly 2283, consider the free body force diagram in FIG. 22C. FIG. 22C illustrates a portion of cam follower assembly 2283 and a portion of preload track 2225. As cam follower assembly 2283 moves wheel 2283W up ramp 2225R of preload track 2225, preload track 2225 exerts a wheel force F_wheel on preload track 2225. Wheel force F_wheel is perpendicular to preload track 2225. Force F_wheel is made up of two perpendicular forces—a retraction force F_retract and a longitudinal force F_long. Retraction force F_retract is a force that the user would apply in the distal direction to move surgical device assembly 300 distally. Alternatively, part or all of this force could be applied by the motor so that the user does not need to exert the full force.

As cam follower assembly 2283 moves from the first location to the second location, a force proportional to longitudinal force F_long is transferred to arm 2282 by cam follower assembly 2283. The force proportional of longitudinal force F_long is applied on motor pack 1541 through arm 2282 and motor pack bracket 2281.

Thus, two acts are performed by cam follower assembly 2282 as cam follower assembly 2283 travels along track 2225. As cam follower assembly 2283 moves up ramp 2225R and rotates, the rotation of cam follower assembly 2283 pushes motor pack distally a distance greater than distance Zload, e.g., motor pack 1541 moves a distance (Zload+Δ). In addition, as cam follower assembly 2283 moves up ramp 2283W, cam follower assembly 2283 transfers a force proportional of longitudinal force F_long to motor pack 1541, which in turn compresses the first and second springs 1601, 1602 so that second preload force is asserted on drive output disk 545. The second preload force is a combination of the forces provided by compressed spring 1601, 1602. A force provided by compressed spring 1602 is larger than a force provided by compressed spring 1601. The second preload force asserted on drive output disk 545 is applied to each of the other disks in disk stack 1400. As described above, in one aspect, the second preload force is 3.0 Lbf. Of course, this is true only when a surgical instrument has been installed, because otherwise the springs do not compress.

Figures 22D, 22E:
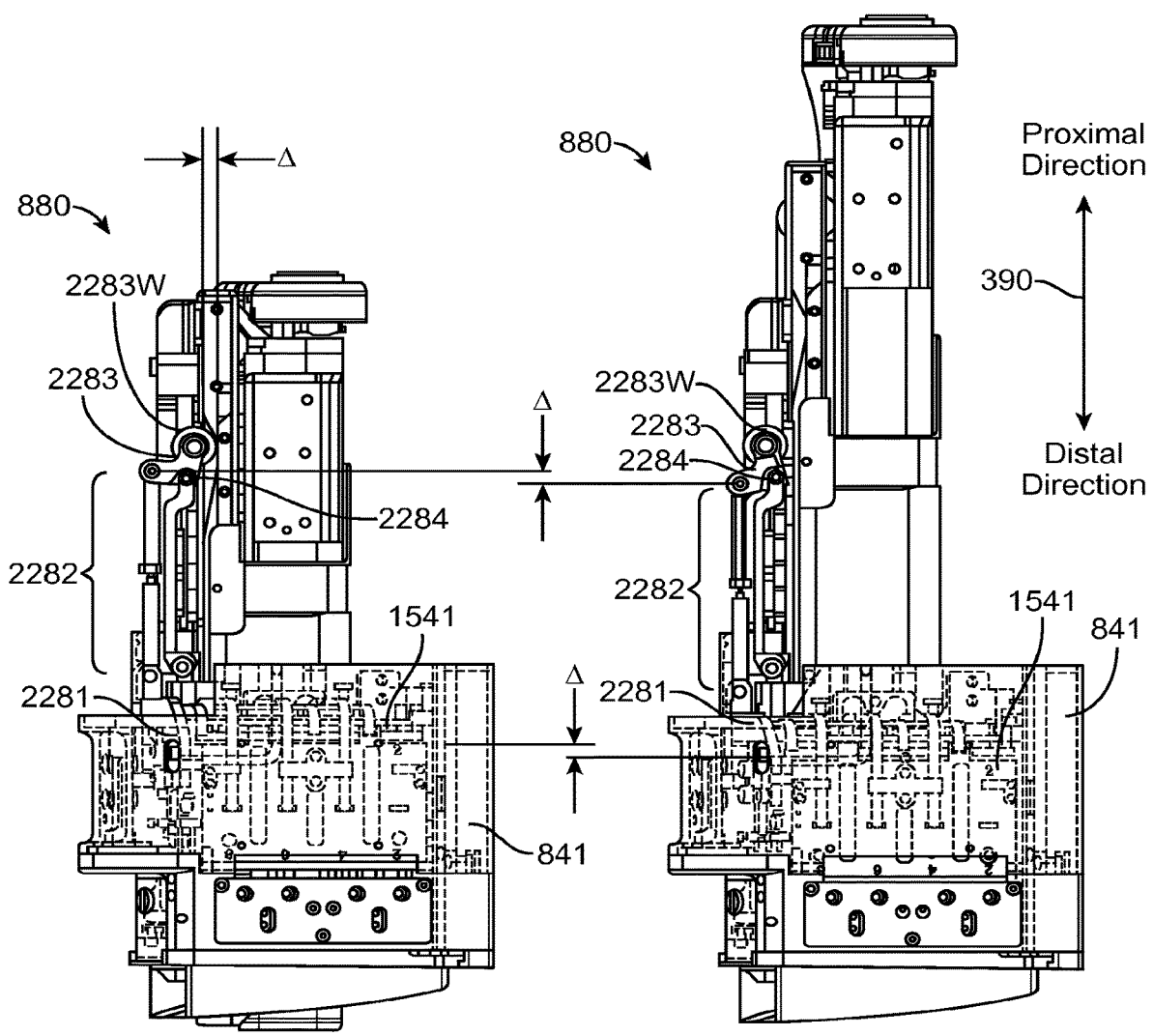
FIGS. 22D and 22E show that a motor pack has moved an additional distance Δ relative to the top of the drive unit housing that moved distance Zload.

FIGS. 22D and 22E shows that motor pack 1541 has moved an additional distance Δ relative to the top of instrument manipulator assembly housing 741 that moved distance Zload. In one aspect, distance Δ is 0.212 inches. In this aspect, FIGS. 22D and 22E show that distance the proximal end of arm 2282 moves as cam follower assembly 2283 rotates is distance Δ. This is illustrative only and is not intended to be limiting.

In other implementations, cam follower assembly 2283 could have different length moment arms 2283M1 and 2283M2 (see FIG. 23) so that when wheel 2283W traverses ramp 2225R having a height Δ, arm 2282 and consequently motor pack 1541 is moved a distance larger than distance Δ, or alternatively could have different length moment arms 2283M1 and 2283M2 (see FIG. 23) so that when wheel 2283W traverses ramp 2225R having a height Δ, arm 2282 and consequently motor pack 1541 is moved a distance smaller than distance Δ. Finally, FIG. 22D illustrates that a ramp 2225R has a height Δ, e.g., wheel 2283W is displaced a distance Δ in a direction perpendicular to track 2225 as wheel 2283W moves from the first position to the second position.

Figure 22F:
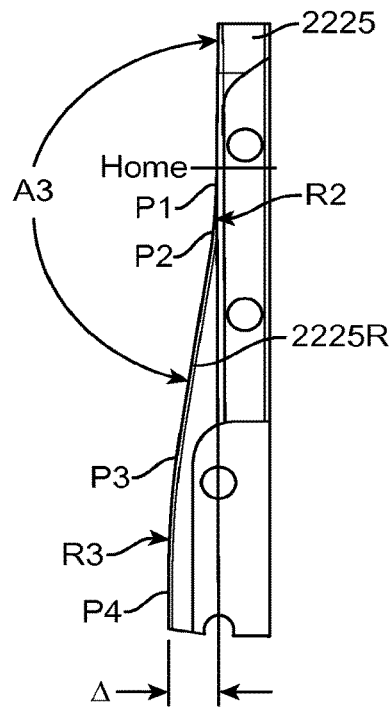
FIG. 22F illustrates, in one aspect, dimensions of the preload track.

FIG. 22F is an illustration of one aspect of preload track 2225. One example of dimensions for preload track 2225 is given in Table 2.

TABLE 2

| REFERENCE NUMBER | DIMENSION |
|---|---|
| Home | 0 inches |
| P1 | 0.05 inches |
| P2 | 0.33 inches |
| P3 | 1.14 inches |
| P4 | 1.92 inches |
| R2 | 1.80 inches (radius) |
| R3 | 5.00 inches (radius) |
| A3 | 171 degrees |
| Δ | 0.212 inches |

Figure 22G:
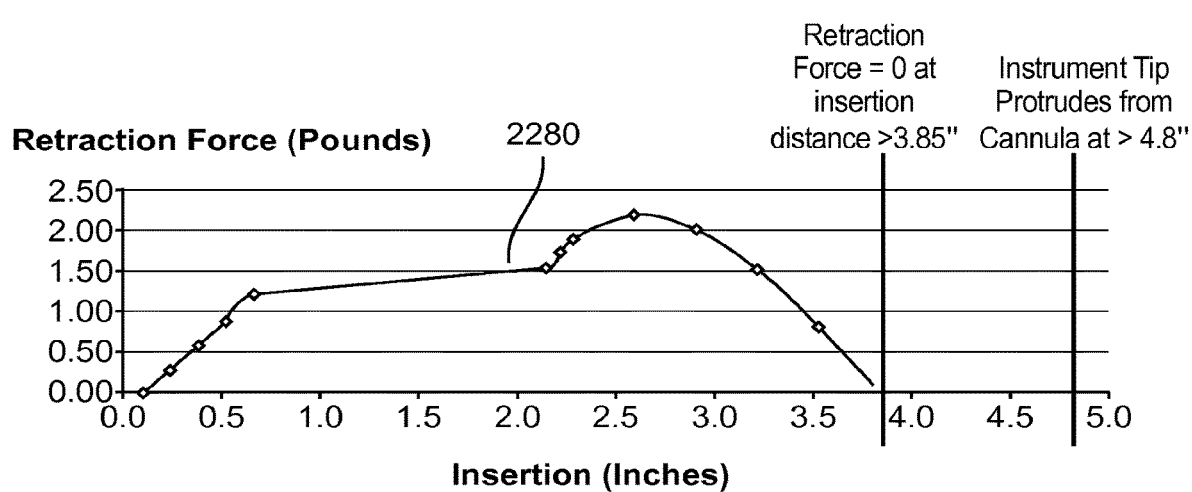
FIG. 22G is a graph of a retraction force versus insertion distance of a surgical instrument.

Preload track 2225 is configured to smoothly ramp the preload force from the first preload force to the second preload force. FIG. 22G is a graph of the retraction force as preload assembly 780 moves distally from the first location to the second location on preload track 2225. Curve 2280 gives the retraction force at each insertion distance. The retraction force acts on the instrument manipulator assembly housing 741 in the proximal direction.

In this example, the first position is an insertion distance of 0.0 inches and the second position is an insertion distance of 3.85 inches. The retraction force increases about linearly from 0.0 to about 0.6 inches, then continues to increase linearly at a reduced slope from about 0.6 to 2.2 inches. From about 2.2 to 2.6 inches, the force increases and peaks, then tapers to zero force at about 3.85 inches. At an insertion distance of 3.85 inches, the second preload force of 2.3 Lbf is reached. At an insertion distance of 3.85 inches, the second preload spring is compressed to its maximum value in this design, and so provides no additional resistance to distal motion. In this example, the instrument tip protrudes from the cannula at an insertion depth of 4.8 inches or larger. Thus, disk stack 1400 is fully preloaded and the backlash effectively reduced to zero before the instrument tip exits the cannula.

With curve 2280, a track is machined that provides this retraction force versus insertion profile. The machining creates a preload track profile that smoothly ramps the preload force according to curve 2280. Curve 2280 is illustrative only and is not intended to be limiting. In view of this disclosure, one knowledgeable in the field can create a retraction force versus insertion distance for a particular preload spring assembly and a particular cannula and surgical instrument.

Figure 23:
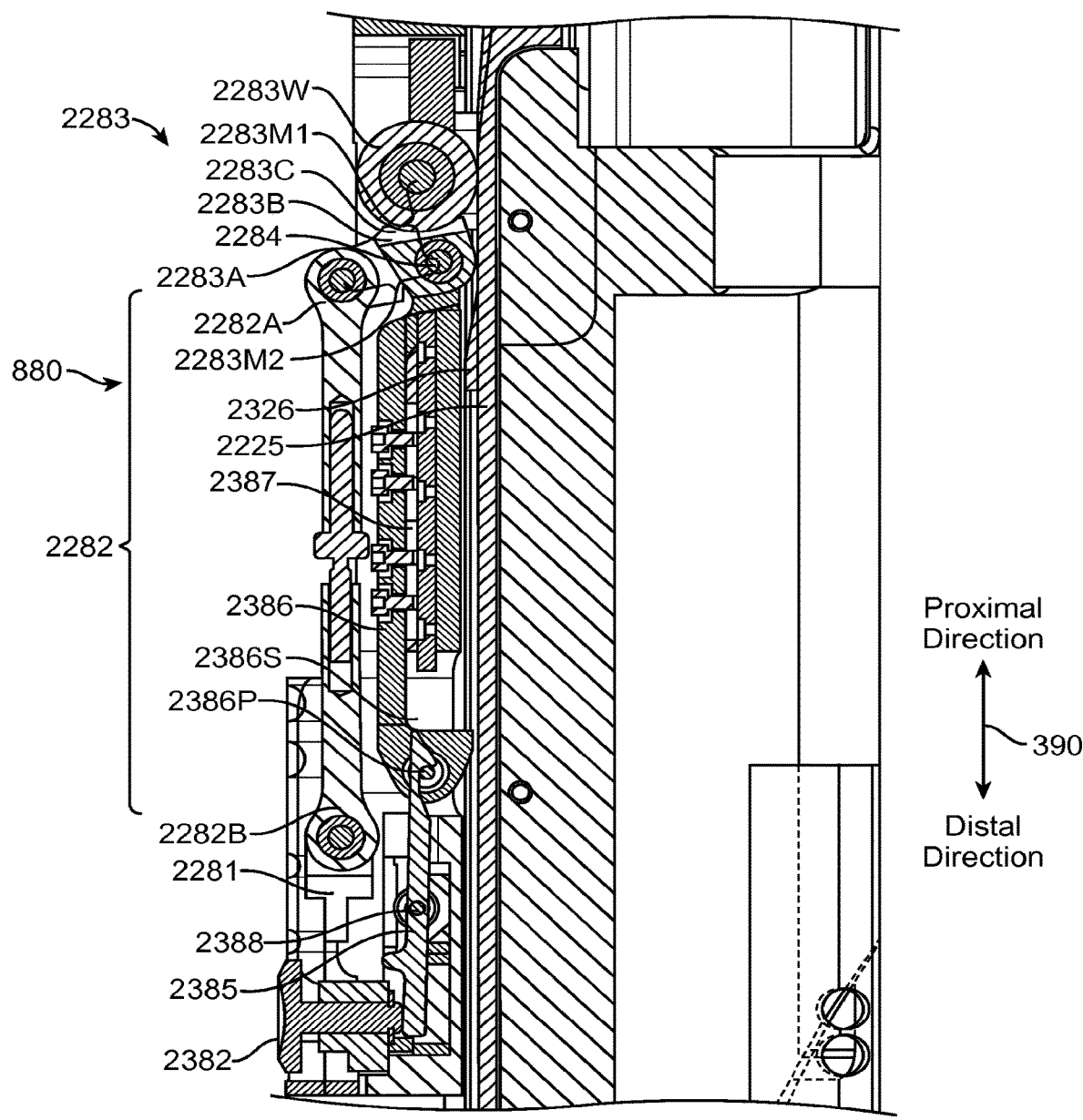
FIG. 23 is a more detailed illustration of the preload assembly.

FIG. 23 is a more detailed illustration of preload assembly 780. Arm 2282 has a first end 2882A rotatably connected to a first end 2283A of an L-shaped body 2283B of cam follower assembly 2283. A second end 2282B of arm 2282 is connected to motor pack bracket 2281. Motor pack bracket 2281 is affixed to motor pack 1541.

In this aspect, first moment arm 2283M1 is perpendicular to second moment arm 2283M2 at pivot pin 2284 and have a same length. Thus, in this aspect, longitudinal force F_long is applied to motor pack 1541 However, in other aspects, the two moment arms may not be perpendicular. If the moment arms are not perpendicular, or if the moment arms have different lengths, the force applied to motor pack 1541 is proportional to longitudinal force F_long. In each aspect, the shape of body 2283B is selected to accommodate the two moment arms and to provide the necessary strength to rotate and transfer the longitudinal force to the motor pack.

Second end 2283C of L-shaped body 2283B is rotatably connected to wheel 2283W. Wheel 2283W rides on preload track 2225. A vertex of L-shaped body 2283B is rotatably connected to pivot pin 2284. Pivot pin 2284 is fixedly attached to instrument manipulator assembly housing 741 of instrument manipulator assembly 240. First moment arm 2283M1 of preload assembly 740 extends from the center of rotation of wheel 2283W to a center of rotation of vertex of L-shaped body 2283B. Second moment arm 2283M2 of preload assembly 740 extends from the center of rotation of first end 2282A of arm 2282 to a center of rotation of vertex of L-shaped body 2283B. Since the distance between pivot pin 2284 and track 2225 is fixed, as wheel 2283W moves distally up the ramp, cam follower assembly 2283 rotates as indicated in FIG. 22B and so motor pack 1541 is displaced relative to instrument manipulator assembly housing 741 and consequently longitudinal force F_long is applied on spring assemblies in motor pack 1541.

In FIG. 23, preload assembly 780 also includes a preload release mechanism. The preload release mechanism includes a preload release button 2382, a preload release lever 2385, a preload engagement arm 2386, and a return spring (not shown, but see FIGS. 4A to 4H). Preload release button 2382 is an example of preload release button 482. Also not shown in FIG. 23 is a torsional spring, concentric with pin 2388, which exerts a clockwise torque on preload release lever 2385 (clockwise relative to FIG. 23). This is necessary to keep preload release lever 2385 and preload release button 2382 in the unreleased position (shown), unless release button 2382 is pressed.

A first end, a proximal end, of preload engagement arm 2386 is rotatably coupled to pivot pin 2284. A rolling pin 2386P is mounted in a second end, a distal end of preload engagement arm 2386. Proximal to rolling pin 2386P in the second end of preload engagement arm 2386 is a preload engagement surface 2386S. In this aspect, preload engagement surface 2386S is perpendicular to the flat portion of preload track 2225. Preload engagement arm 2386 is coupled to a linear rail.

A hook on a first end, a proximal end, of preload release lever 2385 is engaged with rolling pin 2386P in the second end of preload engagement arm 2386. Preload release button 2382 is coupled to, e.g., is in contact with, a second end, a distal end, of preload release lever 2385. Between the first and second ends of preload release lever 2385, preload release lever is rotatably mounted on another pivot pin 2388, which functions as a fulcrum for preload release lever 2385.

In this example, preload release lever 2385 is a Class 1 lever because the fulcrum is between the effort (the forces supplied by preload release button 2382) and the load (the coupling between the hook and rolling pin 2386P). While in this example, preload release lever 2385 is implemented as a Class 1 lever, this is illustrative only and is not intended to be limiting. In other aspects, a Class 2 lever or a Class 3 lever could be used. For a Class 2 lever, the load is between the fulcrum and the effort, and for a Class 3 lever, the effort is between the fulcrum and the load.

If insertion assembly 331 jams, the high preload force must be released so that surgical instrument 260 can be removed. To remove surgical instrument 260, a user pushes preload release button 2382 (FIG. 24A). In response to the force provided by the user, preload release button 2382 applies a force to the second end of preload release lever 2385. The force on the second end preload release lever 2385 causes preload release lever 2385 to rotate about pivot pin 2388 and disengage the hook on the second end of preload release lever 2385 from rolling pin 2386P that is mounted in the second end of preload engagement arm 2386.

Recall that the return spring is mounted between instrument manipulator assembly housing 741 and motor pack 1541 and is stretched when the high preload force is applied. Consequently, when preload release lever 2385 disengages from preload engagement arm 2386, the return spring retracts motor pack 1541 to a fully withdrawn position.

At the fully withdrawn position, there is no preload force, and drive output disk 545 is disengaged from intermediate disk 653. In addition, a release latch inhibit stop and a plurality of hard stops 2437 are withdrawn so that both instrument sterile adapter assembly 250 and surgical instrument 260 can be dismounted. If the distal end of surgical instrument 260 is not straight, as a person withdraws the surgical instrument, the cannula forces the distal end of surgical instrument 260 to straighten because the disk stack without the preload force and without drive output disk 545 engaged is back drivable.

Figure 24B:
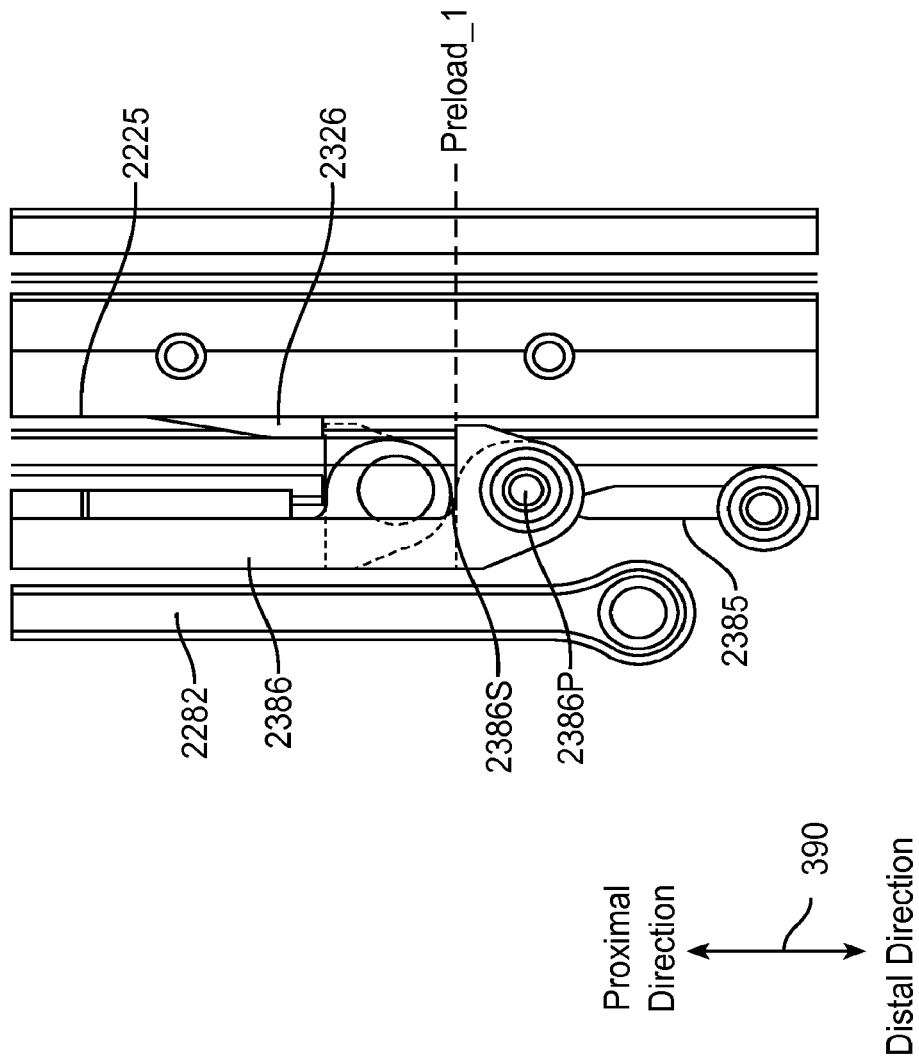
FIG. 24B illustrates an automatic preload reset mechanism of the preload assembly.
Figure 24A:
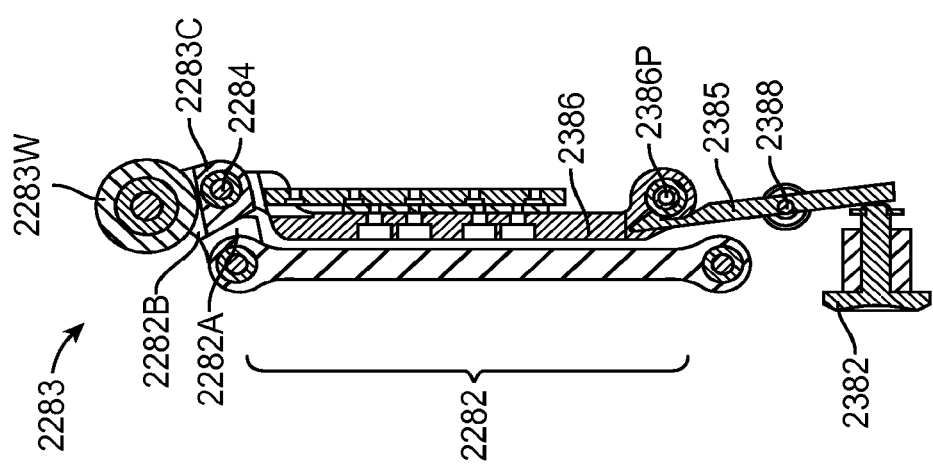
FIG. 24A illustrates release of the cam follower assembly.

FIG. 24B is an illustration of one implementation of the automatic preload reset mechanism in preload assembly 780. When sterile adapter assembly 250 is mounted on instrument manipulator assembly 240, instrument manipulator assembly 240 sends a signal to controller 290 indicating the presence of sterile adapter assembly 250. In response to the signal, controller 290 activates a motor that moves instrument manipulator assembly 240 proximally.

Instrument manipulator assembly housing 741 moves proximally twice as fast as preload engagement ridge 2326 on preload track 2225. This is because distal carriage 2130 moves twice as far as mid carriage 2120. In this aspect, preload engagement ridge 2326 extends from a distal portion of preload track 2225.

Thus, as instrument manipulator assembly housing 741 moves proximally, preload engagement ridge 2326 moves proximally at half the speed of preload engagement arm 2386 and instrument manipulator assembly housing 741. Thus, surface 2386S of preload engagement arm 2386 engages preload engagement ridge 2326 on preload track 2225 as instrument manipulator assembly housing 741 moves proximally. As instrument manipulator assembly housing 741 continues to move proximally, preload engagement ridge 2326 exerts a longitudinal force in the distal direction on surface 2386S of preload engagement arm 2386. This causes cam follower assembly 2283 to apply a longitudinal force on motor pack 1541 as described above. As motor pack 1541 is moved by the longitudinal force in the proximal direction beyond location Preload_1, the hook on preload release lever 2385 (not visible in FIG. 24B) engages rolling pin 2386P. After the engagement of the hook on preload release lever 2385 on rolling pin 2386P, instrument manipulator assembly housing 741 is moved distally so that motor pack 1541 is at location Preload_1. The application of the preload force is automatic upon mounting of sterile adapter assembly 250, in this aspect, and so a preload force is maintained on drive output disk 545 after mounting of sterile adapter assembly 250.

Note that in FIGS. 23, 24A, and 24B only the elements necessary to understand the release mechanism are illustrated. The actual configuration associated with FIGS. 23, 24A, and 24B includes all the elements shown and described with respect to FIG. 22A.

Figure 25:
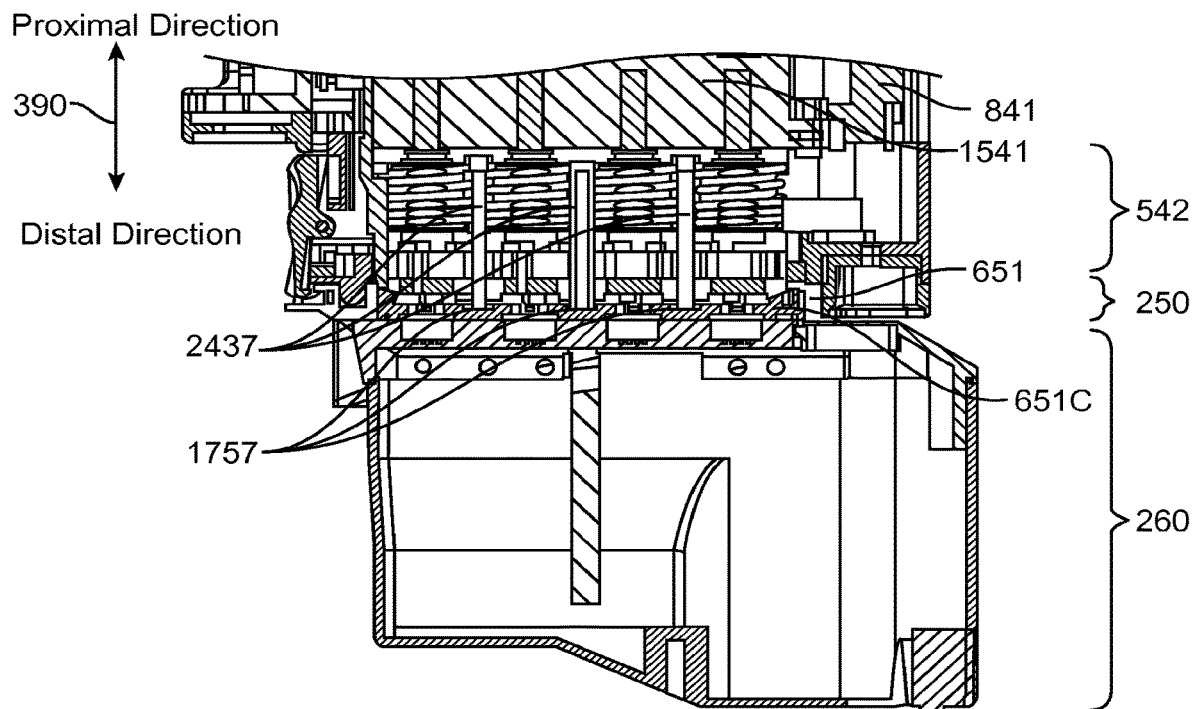
FIG. 25 is a cut-away view of a surgical instrument manipulator assembly, a sterile adapter assembly, and a surgical instrument, and the motor pack of the surgical instrument manipulator assembly includes a plurality of deployed hard stops.

FIG. 25 is a cut-away view of a portion of surgical device assembly 300 that illustrates a surgical instrument removal lockout apparatus. The surgical instrument removal lockout apparatus includes the preload mechanism that applies a preload force on disk stack 1400, a plurality of hard stops 2437, and a plurality of hard stop receptacles 1757. Plurality of hard stops 2437 are an example of plurality of hard stops 437.

Each of plurality of hard stops 2437 extends in a distal direction from a distal face of motor pack 1541. As illustrated in FIG. 17A, each of plurality of hard stop receptacles 1757 extends from a proximal face of moveable body 651C of sterile adapter assembly 250 in a distal direction into moveable body 651C.

When sterile adapter 250 is mounted on surgical instrument manipulator assembly 240 and the preload force is automatically engaged as described above, moveable body 251 is at the most distal position within sterile adapter frame 651 of sterile adapter assembly 250. In this position, plurality of hard stops 2437 is not in plurality of hard stop receptacles 1757, and movable body 651C is free to move within sterile adapter frame 651.

Hence, surgical instrument 260 can be mounted in sterile adapter assembly 250 as described above. However, when the second preload force is applied on output drive assemblies 543 and the spring assembly is fully compressed, plurality of hard stops 2437 extend into plurality of hard stop receptacles 1757, and plurality of hard stops 2437 prevents moveable body 651C from moving in the proximal direction. Removal of surgical instrument 260 moves movable body 651C in the proximal direction. Hence, if the second preload force is applied to motor pack 1541, plurality of hard stops 2437 prevents moveable body 651C from moving in the proximal direction, and consequently removal of surgical instrument 260 is inhibited.

The use of plurality of hard stop receptacles 1757 is illustrative only and is not intended to be limiting. In another aspect, plurality of hard stop receptacles 1757 is not used. Instead, plurality of hard stops 2437 contact a proximal surface of moveable body 651C and prevent movement of moveable body 651C in the proximal direction.

Hence, a surgical instrument manipulator assembly 240 includes an instrument manipulator assembly housing 741, sometimes referred to as housing 741, and a motor pack 1541. Motor pack 1541 is movably coupled to housing 741. A plurality of hard stops 2437 are mounted in a distal end of motor pack 1541. Plurality of hard stops 2437 can be positioned in at least a first position and a second position relative to housing 741 of the surgical instrument manipulator assembly 240. When plurality of hard stops 2437 is in the first position, a surgical instrument 260 can be coupled to and decoupled from instrument manipulator assembly 240. When plurality of hard stops 2437 is in the second position, surgical instrument 260 cannot be decoupled from instrument manipulator assembly 240.

Figures 26A, 26B:
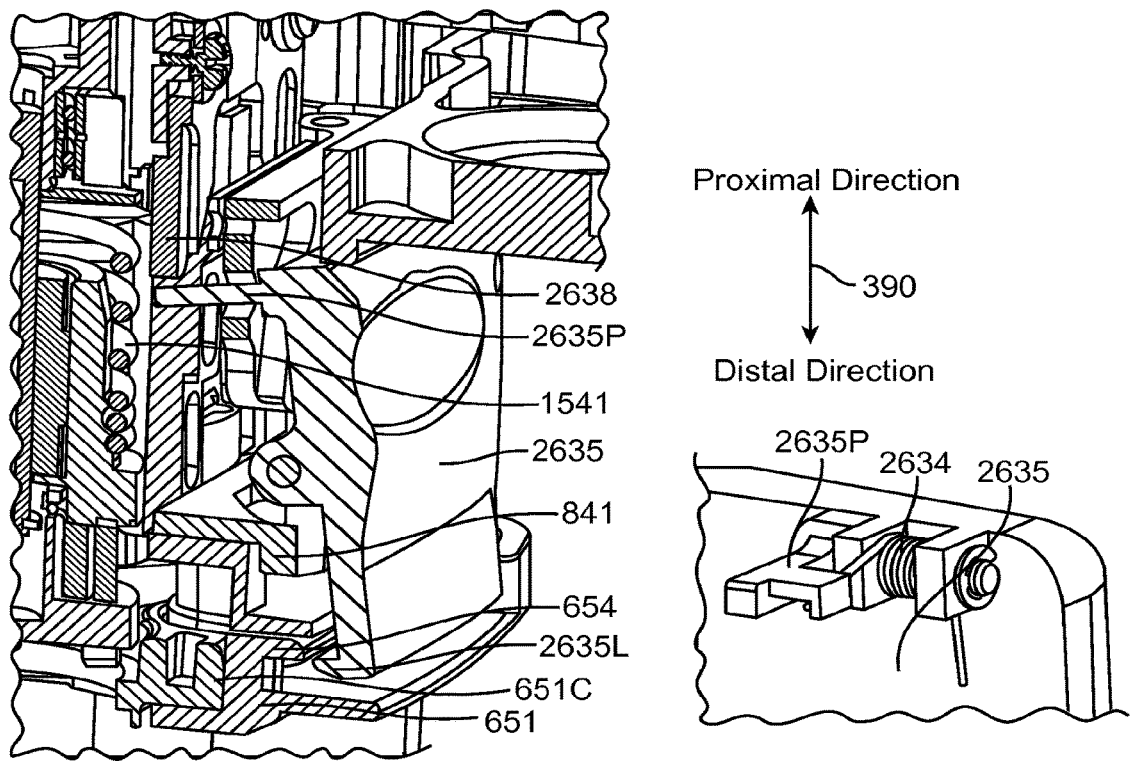
FIGS. 26A and 26B are illustrations of a release latch mechanism and a mechanism to inhibit operation of the release latch mechanism.

FIG. 26A is a more detailed cut-away illustration of sterile adapter release latch 2635. Sterile adapter release latch 2635 is an example of one aspect of release latch 435. Lip 654 on one end of sterile adapter frame 651 is engaged by a lip 2635L extending from a distal end of sterile adapter release latch 2635. Sterile adapter release latch 2635 is mounted in a wall of instrument manipulator assembly housing 741 so that sterile adapter release latch 2635 can pivot to engage with and disengage from sterile adapter frame 651 of sterile adapter assembly 250. In one aspect, the pivotal connection of sterile adapter release latch 2635 to the frame is spring loaded is so that the steady position of latch 2635 is in the engaged position. A latch pin 2635P is coupled to a proximal portion of sterile adapter release latch 2635. When motor pack 1541 is fully withdrawn at location Home, e.g., when no preload force is exerted on motor pack 1541, latch pin 2635P does not prevent sterile adapter release latch 2635 from pivoting to engage with and disengage from sterile adapter frame 651.

When sterile adapter assembly 250 is mounted on instrument manipulator assembly 240, the automatic preload reset mechanism, as described above, exerts a preload force, e.g., a light preload force, on motor pack 1541 when motor pack 1541 is moved to location Preload_1 by the preload engagement mechanism. When motor pack 1541 is moved to location Preload_1, release latch inhibit stop 2638 that is mounted to motor pack 1541 also is moved distally.

When motor pack 1541 is at location Preload_1, if the proximal end of sterile adapter release latch 2635 is pushed, latch pin 2635P contacts release latch inhibit stop 2638, which prevents sterile adapter release latch 2635 from pivoting to disengage from sterile adapter frame 651. Thus, when the light preload force is asserted on motor pack 1541, removal of sterile adapter assembly 250 is inhibited.

FIG. 26A illustrates a potential problem if the automatic preload reset mechanism is energized, while sterile adapter release latch 2635 is depressed. As release latch inhibit stop 2638 moves distally, release latch inhibit stop 2638 would hit latch pin 2635P if sterile adapter release latch 2635 were not released. This potentially could damage latch pin 2635P, e.g., bend latch pin 2635P, so that the sterile adapter removal inhibit mechanism would not work properly. Thus, in one aspect latch pin 2636P (FIG. 26B) is pivotally connected to a proximal portion of sterile adapter release latch 2635, and the connection is spring-loaded by spring 2634. Thus, if sterile adapter release latch 2635 is depressed and the automatic preload reset mechanism is energized, upon latch inhibit stop 2638 hitting latch pin 2635P, latch pin 2635P pivots and so is not damaged. When sterile adapter release latch 2635 is released, spring 2634 causes latch pin 2633P to return to its original position.

In some of the above examples, the terms "proximal" or "proximally" are used in a general way to describe an object or element which is closer to a manipulator arm base along a kinematic chain of system movement or farther away from a remote center of motion (or a surgical site) along the kinematic chain of system movement. Similarly, the terms "distal" or "distally" are used in a general way to describe an object or element which is farther away from the manipulator arm base along the kinematic chain of system movement or closer to the remote center of motion (or a surgical site) along the kinematic chain of system movement.

As used herein, "first," "second," "third," "fourth," etc. are adjectives used to distinguish between different components or elements. Thus, "first," "second," "third," "fourth," etc. are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. An apparatus comprising:
an intermediate disk comprising a proximal portion and a distal portion, the distal portion of the intermediate disk comprising a drive dog and an engagement structure; and
a driven disk comprising a driven interface configured to mate with the distal portion of the intermediate disk, the driven interface of the driven disk comprising an engagement receptacle, a drive dog receptacle, and a rotation disable element;
wherein engagement of the rotation disable element prevents rotation of the driven disk; and
wherein the engagement receptacle is configured to receive the engagement structure upon the engagement structure being aligned with the engagement receptacle.

2. The apparatus of claim 1, wherein:
the intermediate disk comprises a distal surface on the distal portion of the intermediate disk; and
the engagement structure comprises an open three-dimensional structure extending in a distal direction from the distal surface of the intermediate disk.

3. The apparatus of claim 2, wherein the open three-dimensional structure comprises a circular track.

4. The apparatus of claim 3, wherein:
the circular track comprises a first end and a second end;
a centerline is defined extending from a center of the circular track and through a point equidistant from the first and second ends of the circular track;
the open three-dimensional structure further comprises a wall;
the wall extends from the first end of the circular track laterally towards an outer edge of the distal surface of the intermediate disk in a direction substantially parallel to the centerline;
the wall extends away from the distal surface of the intermediate disk at a first height;
the circular track extends away from the distal surface of the intermediate disk at a second height; and
the first height of the wall is smaller than the second height of the circular track.

5. The apparatus of claim 2, wherein the open three-dimensional structure comprises:
a linear track portion extending away from the distal surface of the intermediate disk at a first height;
a curved track portion extending away from the distal surface of the intermediate disk at a second height; and
the first height of the linear track portion is smaller than the second height of the curved track portion.

6. The apparatus of claim 1, wherein the drive dog comprises:
a first portion comprising a three-dimensional structure; and
a second portion extending from the first portion, the second portion comprising two opposing second portion side surfaces, each of the two opposing second portion side surfaces comprising a curved surface.

7. The apparatus of claim 1, wherein:
the driven disk comprises a proximal surface;
the engagement receptacle further comprises a groove;
the groove extends from the proximal surface into the driven interface;
the groove extends along the proximal surface from a first end to a second end;
the first end of the groove is separated from the rotation disable element by a first gap; and
the second end of the groove is separated from the rotation disable element by a second gap.

8. The apparatus of claim 7, wherein:
the groove comprises a width and a depth; and
the width and the depth of the groove are sized to accept the engagement structure of the intermediate disk.

9. The apparatus of claim 1, wherein:
the driven disk comprises a proximal surface;
the engagement receptacle comprises a groove extending from the proximal surface into the driven interface;
the rotation disable element comprises a rotation locking mechanism;
the rotation locking mechanism is at least partially bounded by the groove; and
the rotation locking mechanism flexes relative to the proximal surface of the driven disk.

10. The apparatus of claim 9, wherein the groove comprises a curved groove segment and a linear groove segment.

11. The apparatus of claim 1, wherein the rotation disable element comprises a flexure.

12. The apparatus of claim 11, wherein the rotation disable element further comprises a rotation locking mechanism extending from the flexure.

13. The apparatus of claim 12, wherein the rotation locking mechanism comprises a tang.

14. The apparatus of claim 1, wherein:
the apparatus comprises a preload spring;
the preload spring is coupled to the intermediate disk;
the intermediate disk comprises an intermediate drive interface, the intermediate drive interface comprising the drive dog and the engagement structure;
on the condition that the preload spring is compressed, a preload force is applied from the intermediate disk on the driven disk via the intermediate drive interface and the driven interface; and
on the condition that the preload force is applied via the intermediate drive interface and the driven interface, a coupling of the intermediate drive interface and the driven interface has non-zero backlash.

15. The apparatus of claim 14, wherein:
the preload spring is a first preload spring and the preload force is a first preload force;
the apparatus further comprises a second preload spring coupled to the intermediate disk;
on the condition that the second preload spring and the first preload spring are compressed, a second preload force is applied from the intermediate disk on the driven disk via the intermediate drive interface and the driven interface; and
on the condition that the second preload force is applied via the intermediate drive interface and the driven interface, the coupling of the intermediate drive interface and the driven interface between the intermediate disk and the driven disk has zero backlash.

16. An apparatus comprising:
a first disk and a second disk aligned to rotate around a common axis, the first disk comprising an engagement structure oriented toward the second disk, and the second disk comprising an engagement receptacle and a rotation disable element both oriented toward the first disk;
wherein at a first relative orientation between the first and second disks around the common axis, the engagement structure of the first disk contacts the rotation disable element of the second disk, and the rotation disable element prevents the engagement structure from being received in the engagement receptacle of the second disk; and
wherein at a second relative orientation between the first and second disks about the common axis different from the first relative orientation, the engagement structure of the first disk bypasses the rotation disable element of the second disk, and the engagement structure of the first disk is received in the engagement receptacle of the second disk.

17. The apparatus of claim 16, wherein:
the first disk comprises a first surface oriented toward the second disk; and
the engagement structure comprises an open three-dimensional structure that extends from the first surface of the first disk toward the second disk.

18. The apparatus of claim 16, wherein:
the second disk comprises a second surface oriented toward the first disk;
the engagement receptacle comprises a groove in the second surface of the second disk; and
the groove comprises a curved groove segment and a linear groove segment.

19. The apparatus of claim 16, further comprising:
a body comprising one or more receptacles;
wherein at the first relative orientation between the first and second disks, the rotation disable element is engaged with a receptacle of the one or more receptacles of the body; and
wherein at the second relative orientation between the first and second disks, the second disk rotates within the body.

20. The apparatus of claim 16, wherein the rotation disable element comprises a flexure.

* * * * *